United States Patent
Kamm et al.

(10) Patent No.: US 12,398,355 B2
(45) Date of Patent: Aug. 26, 2025

(54) MICRO PHYSIOLOGICAL MODEL FOR NEURONAL AND MUSCULAR DISEASES AND DISORDERS

(71) Applicant: Massachusetts Institute of Technology, Cambridge, MA (US)

(72) Inventors: Roger Dale Kamm, Cambridge, MA (US); Tatsuya Osaki, Cambridge, MA (US); Sebastien Guy Marcel Uzel, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 952 days.

(21) Appl. No.: 17/602,655

(22) PCT Filed: Apr. 9, 2019

(86) PCT No.: PCT/US2019/026594
§ 371 (c)(1),
(2) Date: Oct. 8, 2021

(87) PCT Pub. No.: WO2020/209843
PCT Pub. Date: Oct. 15, 2020

(65) Prior Publication Data
US 2022/0169965 A1    Jun. 2, 2022

(51) Int. Cl.
*C12M 3/06* (2006.01)
*A61K 31/436* (2006.01)
(Continued)

(52) U.S. Cl.
CPC ........... *C12M 23/16* (2013.01); *A61K 31/436* (2013.01); *A61K 31/4706* (2013.01);
(Continued)

(58) Field of Classification Search
CPC ....... A61K 45/06; C12M 23/04; C12M 23/34; C12M 33/04; C12M 41/40; C12M 41/48;
(Continued)

(56) References Cited

U.S. PATENT DOCUMENTS 5,989,591 A   11/1999  Nagi
6,002,008 A   12/1999  Wissner
(Continued)

FOREIGN PATENT DOCUMENTS

WO    2013056019        4/2013
WO    2015013210        1/2015
WO    WO-2017218581 A1 * 12/2017 ............ C12M 21/08

OTHER PUBLICATIONS

"Human embryonic stem cell (hESC)", Cell Line, 1-16 (2017).
(Continued)

*Primary Examiner* — Michael L Hobbs
(74) *Attorney, Agent, or Firm* — Pabst Patent Group LLP

(57) ABSTRACT

Microfluidic devices with neuronal cells, muscle cells, and optionally other cell types co-cultured therein are provided. Typically one or more the cells has a mutation that contributes to or causes a neuronal or muscular disease or disorder. For example, in some embodiments, one or more of the cultured cells are derived from a subject with a neuronal or muscular disease or disorder. The microfluidic device can facilitate formation of a 3D motor unit and a neuromuscular junction in vitro, and be used to monitor the molecular, biochemical, cellular, and morphological differences in the formation of such structures by healthy and diseased cells, and for testing compounds, dosages of compounds, dosing regimes, and combinations thereof, that may improve or worsen their formation. An exemplary combination drug therapy identified in this way is also provided.

29 Claims, 24 Drawing Sheets

(51) Int. Cl.

| | |
|---|---|
| A61K 31/4706 | (2006.01) |
| A61K 31/496 | (2006.01) |
| A61K 45/06 | (2006.01) |
| C12M 1/00 | (2006.01) |
| C12M 1/12 | (2006.01) |
| C12M 1/26 | (2006.01) |
| C12M 1/34 | (2006.01) |
| C12M 1/36 | (2006.01) |
| C12N 5/0793 | (2010.01) |
| G01N 33/50 | (2006.01) |

(52) U.S. Cl.
CPC ............ *A61K 31/496* (2013.01); *A61K 45/06* (2013.01); *C12M 23/04* (2013.01); *C12M 23/34* (2013.01); *C12M 33/04* (2013.01); *C12M 41/40* (2013.01); *C12M 41/48* (2013.01); *C12N 5/0619* (2013.01); *G01N 33/5058* (2013.01)

(58) Field of Classification Search
CPC ................ C12N 5/0619; G01L 3/5085; G01L 3/502761; G01L 2200/0663; G01L 2300/0609; G01L 2300/0663; G01N 33/5058; G01N 33/5061
See application file for complete search history.

(56) References Cited

U.S. PATENT DOCUMENTS

| | | | |
|---|---|---|---|
| 7,417,148 | B2 | 8/2008 | Boschelli |
| 7,767,678 | B2 | 8/2010 | Tesconi |
| 7,919,625 | B2 | 4/2011 | Boschelli |
| RE42,376 | E | 5/2011 | Wissner |
| 9,261,496 | B2 | 2/2016 | Kamm |
| 9,523,672 | B2 | 12/2016 | Chung |
| 10,233,415 | B1 | 3/2019 | Mathur |
| 10,961,496 | B2 | 3/2021 | Levner |
| 2005/0003511 | A1 | 1/2005 | Bradshaw |
| 2008/0257735 | A1 | 10/2008 | Jeon |
| 2011/0159522 | A1* | 6/2011 | Kamm ............... G01N 33/5029 435/287.1 |
| 2011/0306041 | A1 | 12/2011 | Viovy |
| 2014/0141514 | A1 | 5/2014 | Yoon |
| 2014/0220555 | A1 | 8/2014 | Chen |
| 2015/0030595 | A1 | 1/2015 | Lee |
| 2015/0087006 | A1 | 3/2015 | Pak |
| 2016/0045641 | A1* | 2/2016 | Chou .................. A61L 27/3633 424/422 |
| 2016/0097027 | A1 | 4/2016 | Nikkhah |
| 2017/0355945 | A1* | 12/2017 | Kamm .................. C12M 21/08 |
| 2018/0267014 | A1 | 9/2018 | Perlson |
| 2018/0298317 | A1 | 10/2018 | Ingber |
| 2018/0346859 | A1 | 12/2018 | Varone |
| 2019/0316068 | A1 | 10/2019 | Chen |
| 2021/0031199 | A1 | 2/2021 | Troiano |

OTHER PUBLICATIONS

"Human induced pluripotent stem cell (hiPSC)", Cell Line, 1-11 (2017).
"Human iPS Cell Line (Amyotrophic Lateral Sclerosis)", iXCells Biotech., 1-3.
Abernathy, et al., "MicroRNAs Induce a Permissive Chromatin Environment that Enables Neuronal Subtype-Specific Reprogramming of Adult Human Fibroblasts", Cell Stem Cell, 21(3):332-348. e9 (2017).
Arai, et al., "TDP-43 is a component of ubiquitin-positive tau-negative inclusions in frontotemporal lobar degeneration and amyotrophic lateral sclerosis", Biochem. Biophys. Res. Commun., 351(3):602-611 (2006).
Blasco, et al., "The Glutamate Hypothesis in ALS: Pathophysiology and Drug Development", Curr. Med. Chem., 21(31):3551-3575 (2014).
Bodine, et al., "Akt/mTOR pathway is a crucial regulator of skeletal muscle hypertrophy and can prevent muscle atrophy in vivo", Nat. Cell Biol., 3:1014-1019 (2001).
Boyle, et al., "Association of Muscle Strength With the Risk of Alzheimer Disease and the Rate of Cognitive Decline in Community-Dwelling Older Persons", Arch. Neurol., 66(11):1339-1344 (2009).
Chen, et al., "Autophagy Dysregulation in Amyotrophic Lateral Sclerosis", Brain Pathol., 22(1):110-116 (2012).
Chen, et al., "Modeling ALS with iPSCs Reveals that Mutant SOD1 Misregulates Neurofilament Balance in Motor Neurons", Cell Stem Cell, 14(6):796-809 (2014).
Darabi, et al., "Human ES- and iPS-Derived Myogenic Progenitors Restore Dystrophin and Improve Contractility upon Transplantation in Dystrophic Mice", Cell Stem Cell, 10(5):610-619 (2012).
Dejesus-Hernandez, et al., "Expanded GGGGCC Hexanucleotide Repeat in Noncoding Region of C9ORF72 Causes Chromosome 9p-Linked FTD and ALS", Neuron., 72(2):245-256 (2011).
Devlin, et al., "Human iPSC-derived motoneurons harbouring TARDBP or C9ORF72 ALS mutations are dysfunctional despite maintaining viability", Nat. Commun., 6:5999 (2015).
Dimos, et al., "Induced Pluripotent Stem Cells Generated from Patients with ALS Can Be Differentiated into Motor Neurons", Science, 321(5893):1218-1221 (2008).
Donnelly, et al., "RNA Toxicity from the ALS/FTD C9ORF72 Expansion Is Mitigated by Antisense Intervention", Neuron, 80:415-428 (2013).
Dupont-Versteegden, "Apoptosis in skeletal muscle and its relevance to atrophy", World J. Gastroenterol., 12(46):7463-7466 (2006).
Egawa, et al., "Drug screening for ALS using patient-specific induced pluripotent stem cells", Sci. Transl. Med., 4(145):145ra104 (2012).
Fisher, et al., "A scalable, fully automated process for construction of sequence-ready human exome targeted capture libraries", Genome Biol., 12(1):R1 (2011).
Garbuzova-Davis, et al., "Impaired blood-brain/spinal cord barrier in ALS patients", Brain Res., 1469:114-128 (2012).
Groebe, et al., "On the relation between size of necrosis and diameter of tumor spheroids", Biol. Phys., 34(2):395-401 (1996).
Guo, et al., "SeqMule: automated pipeline for analysis of human exome/genome sequencing data", Sci. Rep., 5:14283 (2015).
Hardiman, et al., "Clinical diagnosis and management of amyotrophic lateral sclerosis", Nat. Rev. Neurol., 7:639-649 (2011).
Hiatt, et al., "Ciliary neurotrophic factor (CNTF) promotes skeletal muscle progenitor cell (MPC) viability via the phosphatidylinositol 3-kinase-Akt pathway", J. Tissue Eng. Regen. Med., 8:963-968 (2014).
Hounoum, et al., "NSC-34 Motor Neuron-Like Cells Are Unsuitable as Experimental Model for Glutamate-Mediated Excitotoxicity", Front. Cell. Neurosci., 10:118 (2016).
Imamura, et al., "The Src/c-Abl pathway is a potential therapeutic target in amyotrophic lateral sclerosis", Sci. Transl. Med., 9(391):eaaf3962 (2017).
Inoue, et al., "The use of induced pluripotent stem cells in drug development", Clin. Pharmacol. Ther., 89(5):655-661 (2011).
International Search Report for corresponding PCT application PCT/US2019/026594 dated Jan. 17, 2020.
Ionescu, et al., "Compartmental microfluidic system for studying muscle-neuron communication and neuromuscular junction maintenance", European Journal of Cell Biology, 95(2):69-88 (2015).
Ionescu, et al., "Patient-derived co-cultures for studying ALS", Nature Biomedical Engineering, 3(1):13-14 (2018). XP036668763 DOI: 10.1038/S41551-018-0333-8.
Jha, et al., "Motor neuron differentiation from pluripotent stem cells and other intermediate proliferative precursors that can be discriminated by lineage specific reporters", Stem Cell Rev., 11(1):194-204 (2015).
Kato-Negishi, et al., "Rod-Shaped Neural Units for Aligned 3D Neural Network Connection", Adv. Healthc. Mater., 6(1700143):1-7 (2017).

(56) References Cited

OTHER PUBLICATIONS

Kiskinis, et al., "Pathways disrupted in human ALS motor neurons identified through genetic correction of mutant SOD1", Cell Stem Cell, 14(6):781-795 (2014).
Ling, et al., "Converging mechanisms in ALS and FTD: disrupted RNA and protein homeostasis", Neuron, 79(3):416-438 (2013).
Lippmann, et al., "A retinoic acid-enhanced, multicellular human blood-brain barrier model derived from stem cell sources", Sci. Rep., 4:4160 (2014).
Mao, et al., "Long-range neuronal circuits underlying the interaction between sensory and motor cortex", Neuron, 72(1):111-123 (2011).
Maury, et al., "Combinatorial analysis of developmental cues efficiently converts human pluripotent stem cells into multiple neuronal subtypes", Nat. Biotechnol., 33(1):89-96 (2015).
Mehta, et al., "Prevalence of Amyotrophic Lateral Sclerosis—United States, 2012-2013", Surveill. Summ., 65(8):1-12 (2016).
Miller, et al., "Human iPSC-based modeling of late-onset disease via progerin-induced aging", Cell Stem Cell, 13(6):691-705 (2013).
Misgeld, et al., "Roles of neurotransmitter in synapse formation: development of neuromuscular junctions lacking choline acetyltransferase", Neuron, 36(4):635-648 (2002).
Morimoto, et al., "Three-dimensional neuron-muscle constructs with neuromuscular junctions", Biomaterials, 34(37):9413-9419 (2013).
Nageshwaran, et al., "Motor neurone disease", BMJ, 349:g4052 (2014).
Nakazawa, et al., "Linear ubiquitination is involved in the pathogenesis of optineurin-associated amyotrophic lateral sclerosis", Nat. Commun., 7:12547 (2016).
Novak, "Breaking down barriers", Nat. Rev. Cancer, 2:890 (2002).
Osaki, et al., "Microphysiological 3D model of amyotrophic lateral sclerosis (ALS) from human iPS-derived muscle cells and optogenetic motor neurons", Science Advanced, 4(10):1-15 (2018c).
Osaki, et al., "Engineered 3D vascular and neuronal networks in a microfluidic platform", Sci. Rep., 8(1):5168 (2018a).
Osaki, et al., "Microphysiological 3D model of amyotrophic lateral sclerosis (ALS) from human iPS-derived muscle cells and optogenetic motor neurons", Sci. Adv., 4:eaat5847 (2018b). Supplementary Materials.
Pearse, et al., "cAMP and Schwann cells promote axonal growth and functional recovery after spinal cord injury", Nat. Med., 10(6):610-616 (2004).
Pearse, et al., "Transplantation of Schwann cells and/or olfactory ensheathing glia into the contused spinal cord: Survival, migration, axon association, and functional recovery", Glia, 55(9):976-1000 (2007).
Plaitakis, "Glutamate dysfunction and selective motor neuron degeneration in amyotrophic lateral sclerosis: a hypothesis", Ann. Neurol., 28(1):3-8 (1990).
Raman, et al., "Optogenetic skeletal muscle-powered adaptive biological machines", PNAS, 113:3497-3502 (2016).
Redaelli, et al., "In vitro and in vivo identification of ABCB1 as an efflux transporter of bosutinib", J. Hematol. Oncol., 8:81 (2015).
Renton, et al., "A hexanucleotide repeat expansion in C9ORF72 is the cause of chromosome 9p21-linked ALS-FTD", Neuron, 72(2):257-268 (2011).
Renton, et al., "State of play in amyotrophic lateral sclerosis genetics", Nat. Neurosci., 17(1):17-23 (2014).
Sareen, et al., "Targeting RNA foci in iPSC-derived motor neurons from ALS patients with a C9ORF72 repeat expansion", Sci. Transl. Med., 5(208):208ra149 (2013).
Seifert, et al., "Astrocyte dysfunction in neurological disorders: a molecular perspective", Nat. Rev. Neurosci., 7(3):194-206 (2006).
Shefner, et al., "A clinical trial of creatine in ALS", Neurology, 63(9):1656-1661 (2004).
Siciliano, et al., "Clinical trials for neuroprotection in ALS", CNS Neurol. Drug Targets, 9(3):305-313 (2010).
Son, et al., "Conversion of mouse and human fibroblasts into functional spinal motor neurons", Cell Stem Cell, 9(3):205-218 (2011).
Southam, et al., "Microfluidic primary culture model of the lower motor neuron-neuromuscular junction circuit", Methods, 218(2):164-169 (2013).
Takahashi, et al., "Induction of pluripotent stem cells from adult human fibroblasts by defined factors", Cell, 131(5):861-872 (2007).
Trias, et al., "Post-paralysis tyrosine kinase inhibition with masitinib abrogates neuroinflammation and slows disease progression in inherited amyotrophic lateral sclerosis", Journal of Neuroinflammation, 13(1):177 (2016).
Tripathi, et al., "Reactive Astrocytes Promote ALS-like Degeneration and Intracellular Protein Aggregation in Human Motor Neurons by Disrupting Autophagy through TGF-β1", Stem Cell Rep., 9(2):667-680 (2017).
Uzel, et al., "Microfluidic device for the formation of optically excitable, three-dimensional, compartmentalized motor units", Sci. Adv., 2(8):e1501429 (2016).
Winkler, et al., "Blood-spinal cord barrier disruption contributes to early motor-neuron degeneration in ALS-model mice", PNAS, 111(11):E1035-E1042 (2014).
Yamanaka, et al., "Astrocytes as determinants of disease progression in inherited amyotrophic lateral sclerosis", Nat. Neurosci., 11(3):251-253 (2008).

\* cited by examiner

CROSS SECTION OF PILLAR

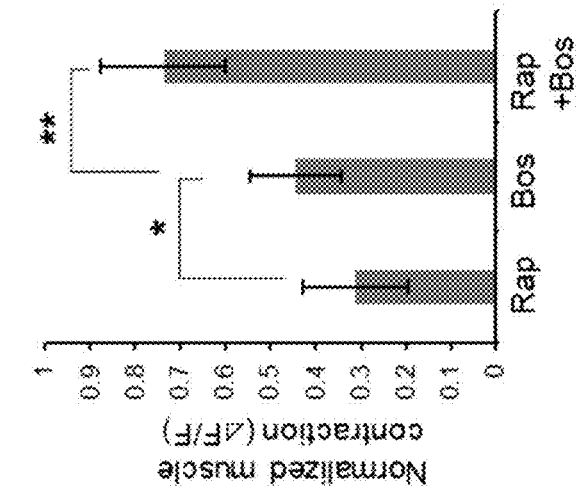
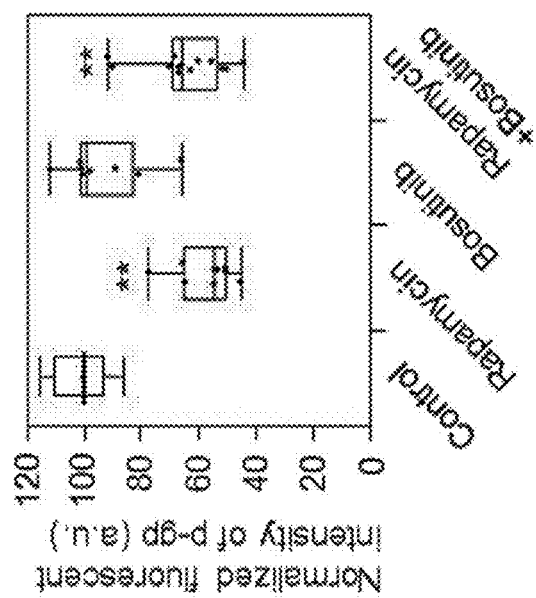
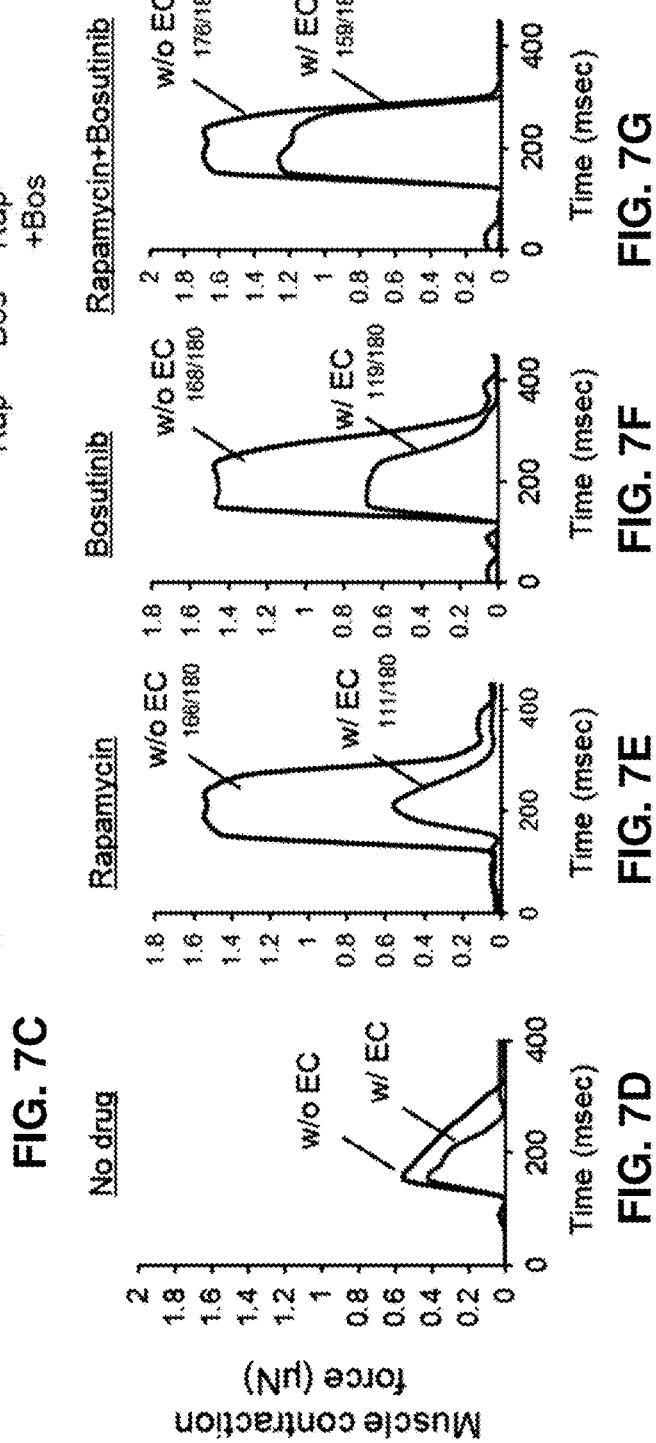

MICRO PHYSIOLOGICAL MODEL FOR NEURONAL AND MUSCULAR DISEASES AND DISORDERS

STATEMENT REGARDING FEDERALLY SPONSORED RESEARCH

This invention was made with government support under Grant CBET-0939511 awarded by the National Science Foundation. The government has certain rights in the invention.

CROSS-REFERENCE TO RELATED APPLICATIONS

This application is a National Phase application under 35 U.S.C. 371 of PCT/US2019/026594, filed Apr. 9, 2019, the disclosure of which is hereby incorporated herein by reference in its entirety.

FIELD OF THE INVENTION

The field of the invention generally relates to devices, systems, compositions, and methods for monitoring the development of heathy and diseased neuronal motor units and neuromuscular junctions, and testing the effects compounds thereon.

BACKGROUND OF THE INVENTION

Amyotrophic lateral sclerosis (ALS), also known as Lou Gehrig's disease, is a neurodegenerative disease in which motor neuron (MN) loss in both the spinal cord and motor cortex causes progressive paralysis, muscle atrophy, and death (Ling et al., *Neuron* 79, 416-438 (2013), Hardiman et al., *Nat. Rev. Neurol.* 7, 639-649 (2011)). The U.S. Centers for Disease Control and Prevention estimates that 12,000 to 15,000 people in the United States have ALS (Mehta et al., *Surveill. Summ.* 65, 1-12 (2016)). Familial ALS (10% of all patients with ALS) is typically associated with mutations in the gene encoding superoxide dismutase (SOD1). The pathogenesis of sporadic ALS (90% of all patients with ALS) remains unclear, but some evidence regarding the pathogenesis has been accumulating over the previous decade (Renton et al., *Nat. Neurosci.* 17, 17-23 (2014)). So far, only riluzole and edaravone have been approved (in 1995 and 2017, respectively) by the U.S. Food and Drug Administration as symptomatic therapy for ALS. However, existing drugs lack effectiveness and only a limited number of drug candidates have been evaluated for the treatment of ALS. Transgenic mice with SOD1 mutations (which exhibit ALS phenotypes) have been widely used for investigating the mechanism underlying ALS and for drug screening.

Clinical studies (Shefner et al., *Neurology* 63, 1656-1661 (2004), Siciliano et al., *Drug Targets* 9, 305-313 (2010)) and two-dimensional (2D) culture models (Takahashi et al., *Cell* 131, 861-872 (2007)) based on induced pluripotent stem cell (iPSC)-derived MNs with several mutations [SOD1, TAR DNA binding protein-43 (TDP-43), and chromosome 9 open reading frame 72 (C9orf72)] from patients with ALS (Dimos et al., *Science* 321, 1218-1221 (2008)) have contributed to the understanding of the mechanism underlying ALS. The 2D culture models have also been used for drug screening. Regarding TDP-43, accumulation of this protein in patients with ALS has been shown to cause neurotoxicity, triggering the development of ALS phenotypes both in vivo and in vitro (Egawa et al., *Sci. Transl. Med.* 4, 145ra104 (2012)).

Regarding SOD1, in vitro research has shown that iPSC-derived MNs with SODIA4V mutations have specific relevant phenotypes, i.e., significant loss of islet1-positive cells, reduced neuronal soma size, and increased apoptosis (Kiskinis et al., *Cell Stem Cell* 14, 781-795 (2014)). Moreover, regarding C9orf72, recent in vivo studies have shown that a mutation in this gene (involving an intronic hexanucleotide repeat expansion) is associated with the development of familial and sporadic ALS (DeJesus-Hernandez et al., *Neuron* 72, 245-256 (2011), Renton et al., *Neuron* 72, 257-268 (2011)). However, in contrast, the SOD1 mutation causes neurite swelling and degeneration, but it is not involved in neural cell death in vitro (Chen et al., *Cell Stem Cell* 14, 796-809 (2014)). Approximately 40% of patients with familial ALS and 8 to 10% of patients with sporadic ALS have a C9orf72 mutation (DeJesus-Hernandez et al., *Neuron* 72, 245-256 (2011), Renton et al., *Neuron* 72, 257-268 (2011)). However, no significant neurotoxins of human pluripotent stem cell-derived MNs with a C9orf72 mutation were identified using an in vitro model, despite the high susceptibility of the MNs to glutamate-mediated excitability (Sareen et al., *Sci. Transl. Med.* 5, 208ra149 (2013), Donnelly et al., *Neuron* 80,415-428 (2013)). These traditional in vitro culture methods have led to important findings related to the development of ALS, but the lack of an in vitro screening model that mimics in vivo function has severely limited the scope of drug development.

Organ-on-a-chip technology has recently been introduced to mimic physiological in vivo conditions in 2D (Southam et al., *Methods* 218, 164-169 (2013)) and 3D (Morimoto et al., *Biomaterials* 34, 9413-9419 (2013)) conditions by coculturing MNs with skeletal muscle cells, thereby producing a model of a motor unit with neuromuscular junctions (NMJs). In particular, these 3D culture platforms can be used to evaluate and quantify MN phenotypes such as MN cell death, synapse formation, and neurodegeneration, as well as muscle contraction and atrophy. These in vitro models have been important for investigating the physiopathological interactions between MNs and skeletal muscle cells in ALS.

Nonetheless, there remains a need for improved resources for studying ALS other neurodegenerative diseases.

Thus, it is an object of the invention to provide improved systems for modeling healthy and diseased neurons and muscle cells and neuromuscular junctions in vitro, and methods of use thereof for screening toxins and treatments.

It is another object of the invention to provide new methods of treating ALS.

SUMMARY OF THE INVENTION

Microfluidic devices with neuronal cells, muscle cells, and optionally other cell types co-cultured therein are provided which have been demonstrated to mimic a human neurological conditions such as ALS. The system is formed using one or more neural and muscle cells, wherein the cells have a mutation that contributes to or causes a neuronal or muscular disease or disorder. For example, in some embodiments, one or more of the cultured cells are derived from a subject with a neuronal or muscular disease or disorder. The microfluidic device facilitates formation of a three dimensional (3D) motor unit and a neuromuscular junction in vitro, which can be used to monitor the molecular, biochemical, cellular, and morphological differences in the formation of such structures by healthy and diseased cells, and to test compounds that may improve or worsen their formation. An exemplary combination drug therapy identified in this way is also provided. This is the first time one has shown formation of nerve-muscle cell motor units that substantially mimic disease and can be used instead of animal models to accurate analyze, evaluate and screen for therapies.

In some embodiments, a microfluidic device has a coculture chamber or a plurality of coculture chambers, each of the chambers including a first culture compartment including one or more retaining features and a healthy, diseased, dysfunctional, or defective neuronal cells; a second culture compartment including one or more compliant pillars and a muscle bundle formed from one or more healthy, diseased, dysfunctional, or defective muscle cells; and a buffer compartment separating the first compartment and the second compartment; wherein the compliant pillars are deflectable to measure force generated by the muscle bundle. Typically, the neuronal cells, the muscle cells, or the combination thereof are diseased, dysfunctional, or defective.

In preferred embodiments, the muscle bundle is innervated by the neuronal cell. Innervation can include one or more of (a) growth of neurites into contact with the external surface of the muscle bundle; (b) growth of neurites past the external surface and into the muscle bundle; and (c) formation of a neuromuscular junction between an axon and a muscle cell of the muscle bundle.

In some embodiments, an axon extends from the first culture compartment through the buffer compartment to the second culture compartment and forms a three-dimensional neuromuscular junction with the muscle bundle.

The device can further include, for example, one or more neuronal inlet injection ports for seeding the first culture compartment with neuronal cells; one or more muscle inlet injection ports for seeding the second culture compartment with muscle cells; a first medium reservoir adjacent the first culture compartment; and a second medium reservoir adjacent the second culture compartment, the first and second medium reservoirs enabling generation of gradients of growth factors and/or other additives to the medium.

Any of the compartments or reservoirs can contain a hydrogel.

In some embodiments, the first culture compartment, the second culture compartment, and/or the buffer compartment contains one or more additional cell types other than the neuronal cells or the muscle cell.

Additional cell types include, for example astrocytes, Schwann cells, endothelial cells, satellite cells, glial cells, or a combination thereof. Any of the additional cells can be healthy, diseased, dysfunctional, or defective.

In particular embodiments, the device includes endothelial cells in the first culture chamber, preferably wherein the endothelial cells form a tight monolayer above the neuronal cells. The endothelial cells can be, for example brain-specific, and mimic the blood-brain barrier.

In some embodiments, one or more of the neuronal cells, muscle cells, astrocytes, Schwann cells, endothelial cells, satellite cells, glial cells or a combination thereof is derived from a subject with a neurological disease or disorder, a muscular disease or disorder, or a combination thereof. Exemplary diseases and disorders include, but are not limited to, amyotrophic lateral sclerosis (ALS), Huntington's disease (HD), a muscular dystrophy, spina bifida, Parkinson's disease (PD) or a PD-related disorders, Alzheimer's disease (AD) or another dementias, a disease of the blood vessels that supply the brain, a seizure disorder, cancer, infection, a prion disease, corticobasal degeneration, frontotemporal dementia, cognitive impairment, a motor neuron disease (MND), spinocerebellar ataxia (SCA), spinal muscular atrophy (SMA), Friedreich's Ataxia, Lewy Body Disease, Alpers' Disease, Batten Disease, Cerebro-Oculo-Facio-Skeletal Syndrome, corticobasal degeneration, Gerstmann-Straussler-Scheinker Disease, Kuru, Leigh's Disease, monomelic amyotrophy, multiple system atrophy, multiple system atrophy with orthostatic hypotension (Shy-Drager Syndrome), Multiple Sclerosis (MS), neurodegeneration with brain iron accumulation, opsoclonus myoclonus, posterior cortical atrophy, primary progressive aphasia, progressive supranuclear palsy, vascular dementia, progressive multifocal leukoencephalopathy, dementia with Lewy Bodies, lacunar syndromes, hydrocephalus, Wernicke-Korsakoff's syndrome, post-encephalitic dementia, cancer and chemotherapy-associated cognitive impairment and dementia, depression-induced dementia, and pseudodementia.

One or more of the neuronal cell, muscle cells, astrocytes, Schwann cells, endothelial cells, satellite cells, glial cells or a combination thereof can be derived from an embryonic stem cell, an induced pluripotent stem cells, and patient-derived primary cells or a combination thereof.

In some embodiments, the first culture compartment has a width of at least 100 µm, the second culture compartment has a width of at least 100 µm, the first and second culture compartments are separated by a distance of at least about 200 µm, the one or more compliant pillars have a height of at least 50 µm, or a combination thereof.

Methods of identifying a compound, a dosage of a compound, a dosing regime, or combination thereof, that effects neuronal activity, muscular activity, or a combination thereof, are provided. The methods typically include (i) making a first measurement of a biochemical, cellular, molecular, or morphological characteristic of the neuronal cell, muscle bundle, or combination thereof of the microfluidic device, (ii) contacting the neuronal cell, muscle bundle, or combination thereof with a test compound, making a second measurement of the biochemical, cellular, molecular, or morphological characteristic of the neuronal cell, muscle bundle, or combination thereof, and (iv) selecting the compound as one that effects neuronal activity, muscular activity, or a combination thereof if the compound improves or worsens the biochemical, cellular, molecular, or morphological characteristic of the neuronal cell, muscle bundle, or combination thereof.

In some embodiments, the compound improves a biochemical, cellular, molecular, or morphological characteristic of the neuronal cells, muscle bundle, or combination thereof, and may be selected as a candidate drug for treatment of a neural or neurological or muscular disease or disorder, particularly when the characteristic that can be improved can alleviate one or more symptoms the neuro-, muscular, or neuromuscular disease.

In some embodiments, the compound worsens a biochemical, cellular, molecular, or morphological characteristic of the neuronal cells, muscle bundle, or combination thereof. Such compounds can be identified as toxins, particularly when worsening the characteristic in a subject would cause or aggravate a neuro-, muscular, or neuromuscular disease or disorder in the subject.

Characteristics include, for example, growth of the cell(s); morphology of the cell(s); analysis of expression of one or more marker proteins; $Ca^{2+}$ imaging; contractile force; neuronal soma size; apoptosis; autophagy; neurite elongation speed; neurite elongation distance; motor unit formation; neuromuscular junction formation; synaptic activity; secretion of ciliary neurotrophic factor (CNTF); inflammation; and combinations thereof.

The marker protein can be, for example, islet1, ChAT, SMI-32, Synapsin I, ATG5, ATG7, ATG16L2, BECN1, ULK1, ULK2, LC3, MYHI, MYHII, MYLII, or a combination thereof. Inflammation can be measured by, for example, determining the expression level of NF-κB, tumor necrosis factor-α (TNF-α), interleukin family proteins, cyclooxygenase-2, or a combination thereof.

Combination therapies based on the identification of candidate drugs are also provided. For example, a method of treating a subject with amyotrophic lateral sclerosis (ALS) can include administering to the subject an effective amount of mTOR inhibitor and/or P-gp inhibitor in combination with a Src/c-Abl pathway inhibitor. The mTOR inhibitor and/or P-gp inhibitor can be administered the subject separately from the Src/c-Abl pathway inhibitor. The mTOR inhibitor and/or P-gp inhibitor can be administered to the subject prior to, after, or a combination thereof relative to the Src/c-Abl pathway inhibitor. The Src/c-Abl pathway inhibitor can be administered to the subject prior to, after, or a combination thereof relative to the mTOR inhibitor and/or P-gp inhibitor.

In some embodiments, the mTOR inhibitor and/or P-gp inhibitor is administered to the subject at the same time as the Src/c-Abl pathway inhibitor. In such embodiments, the compounds can be part of the same or different pharmaceutical compositions.

In particular embodiments, the mTOR inhibitor and/or P-gp inhibitor is administered to the subject in an effective amount to decrease P-gp transporter in an effective amount to reduce transport of the Src/c-Abl pathway inhibitor out of the CNS. Preferably, the P-gp transporter is decreased in an effective amount to increase the concentration of the Src/c-Abl pathway inhibitor in the brain.

The result achieved by the combination therapy can be partially additive, completely additive, or more than additive of the result achieved by administering the mTOR inhibitor and/or P-gp inhibitor and the Src/c-Abl pathway inhibitor alone. In specific embodiments, the mTOR inhibitor and/or P-gp inhibitor is a rapamycin, the Src/c-Abl pathway inhibitor is bosutinib or masitinib, or combination thereof.

BRIEF DESCRIPTION OF THE DRAWINGS

FIG. 7C is a plot showing the immunostaining (Normalized Florescent Intensity (a.u.)) of P-gp without drugs and with rapamycin and cotreatment of rapamycin and bosutinib. FIGS. 7D-7G are bar graphs showing a comparison of muscle contraction force (pN) with and without iEC layer in the presence of no drug (7D), rapamycin (7E), and bosutinib (7F), and cotreatment with both (7G). FIG. 7H is a bar graph showing normalized muscle contraction by rapamycin (Rap), and bosutinib (Bos), and cotreatment with both (Rap+Bos) via iEC layer copared to without iEC layer. (n=4). *, $P<0.05$. **, $P<0.01$. one-way ANOVA. The bars of each column indicate range.

DETAILED DESCRIPTION OF THE INVENTION

I. Definitions

Figure 1A:
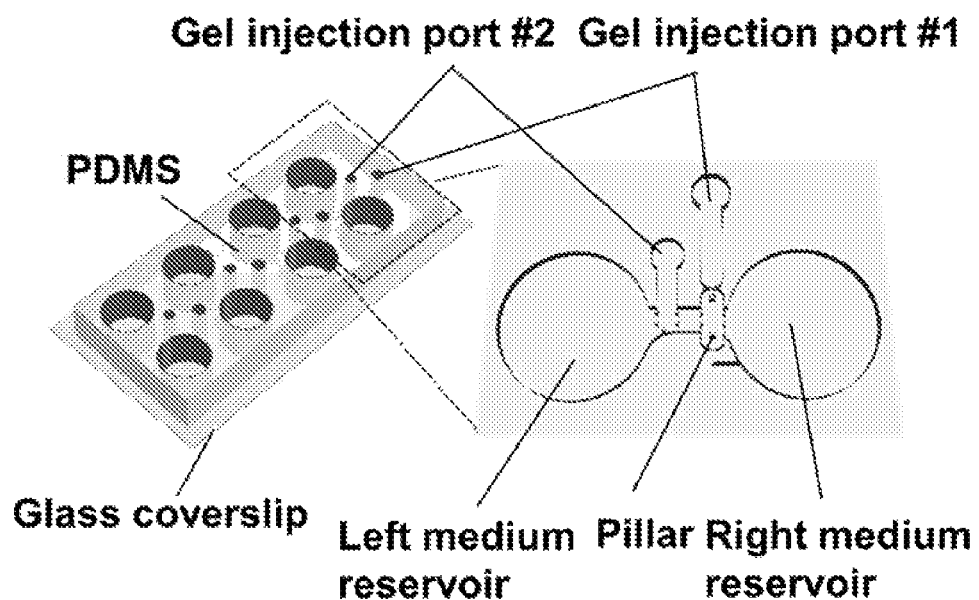
FIG. 1A is a diagram of a micro fabricated motor unit mimic device that uses polydimethylsiloxane (PDMS) microchannels to form four identical sites on a single chip, each composed of a muscle fiber bundle attaching pillar structures and culture MN spheroids. Each site has two medium reservoirs, two gel injection ports, and three compartments.

As used herein the term "small molecule," generally refers to an organic molecule that is less than about 2,000 g/mol in molecular weight, less than about 1,500 g/mol, less than about 1,000 g/mol, less than about 800 g/mol, or less than about 500 g/mol. Small molecules are non-polymeric and/or non-oligomeric.

As used herein, the term "carrier" refers to an organic or inorganic ingredient, natural or synthetic, with which the active ingredient is combined to facilitate the application.

As used herein, the term "pharmaceutically acceptable" describes a material that is not biologically or otherwise undesirable. The term refers to those compounds, materials, compositions, and/or dosage forms which are, within the scope of sound medical judgment, suitable for use in contact with the tissues, organs, and/or bodily fluids of a subject without excessive toxicity, irritation, allergic response, or other problems or complications commensurate with a reasonable benefit/risk ratio. Such materials can be administered to a subject along with the selected compound without causing any undesirable biological effects or interacting in a deleterious manner with any of the other components of the pharmaceutical composition in which it is contained.

As used herein, the term "pharmaceutically-acceptable carrier" means one or more compatible solid or liquid fillers, diluents or encapsulating substances which are suitable for administration to a human or other vertebrate animal.

As used herein, "treatment" or "treating" means to administer a composition to a subject or a system with an undesired condition (e.g., an infectious disease, cancer). The condition can include one or more symptoms of a disease, pathological state, or disorder. Treatment includes medical management of a subject with the intent to cure, ameliorate, stabilize, or prevent a disease, pathological condition, or disorder. This includes active treatment, that is, treatment directed specifically toward the improvement of a disease, pathological state, or disorder, and also includes causal treatment, that is, treatment directed toward removal of the cause of the associated disease, pathological state, or disorder. In addition, this term includes palliative treatment, that is, treatment designed for the relief of symptoms rather than the curing of the disease, pathological state, or disorder; preventative treatment, that is, treatment directed to minimizing or partially or completely inhibiting the development of the associated disease, pathological state, or disorder; and supportive treatment, that is, treatment employed to supplement another specific therapy directed toward the improvement of the associated disease, pathological state, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

As used herein, the terms "effective amount" or "therapeutically effective amount" are used interchangeably and mean a quantity sufficient to alleviate or ameliorate one or more symptoms of a disorder, disease, or condition being treated or to otherwise provide a desired pharmacologic and/or physiologic effect. Such amelioration only requires a reduction or alteration, not necessarily elimination. The precise quantity will vary according to a variety of factors such as subject-dependent variables (e.g., age, immune system health, weight, etc.), the disease or disorder being treated, the disease stage, as well as the route of administration, and the pharmacokinetics and pharmacodynamics of the agent being administered.

Recitation of ranges of values herein are merely intended to serve as a shorthand method of referring individually to each separate value falling within the range, unless otherwise indicated herein, and each separate value is incorporated into the specification as if it were individually recited herein.

II. Microfluidic Device

The compositions and methods typically utilize or otherwise incorporate a microfluidic device (also referred to herein as a system) that enables coculture of neurospheres and muscle bundles and allows for the formation of three-dimensional neuromuscular junctions in a microenvironment that mimics that of an in vivo counterpart. Such devices are described below and in, for example, U.S. Published Application No. 2017/0355945.

The microfluidic devices enable the precise and repeatable three-dimensional and compartmentalized coculture of muscle cells and neuronal cells. The muscle cells form muscle bundles in the device, and the muscle bundles are innervated with axons. The neuronal cells may be, e.g., within one or more neurospheres. When cultured on adherent substrates or in a three-dimensional extracellular matrix (ECM), and under appropriate conditions, neurites spontaneously extend out of the neurospheres. One neurite eventually becomes an axon, and when the motile tip of the axon, the growth cone, comes in contact with a muscle cell, a synapse, called neuromuscular junction, can form.

The microfluidic device can include a plurality, e.g, a series, of coculture chambers, each coculture chamber having a neuronal culture compartment including one or more retaining features that keep the neuronal cells (e.g., in a neurosphere) within the neuronal culture compartment. Non-limiting examples of retaining features include compartment walls with openings for an axon to pass through, pillars, a net (e.g., a rigid netting or mesh of plastic or other material), or plates. In some embodiments, the retaining features are arranged so as to form a concave portion or boundary of the neuronal culture compartment. In some embodiments, the retaining feature is a pillar cap. The coculture chamber may further include a muscle cell culture compartment including one or more compliant pillars. For example, in some embodiments, the device includes 1, 2, 3, 4, 5, 6, 7, 8, 9, or 10 compliant pillars.

In some embodiments a muscle bundle is attached to each of the one or more compliant pillars. For example, in some embodiments, a portion of the muscle bundle is wrapped around each of the one or more compliant pillars.

In various embodiments, the coculture chamber also includes a buffer compartment separating the neuronal cell compartment and the muscle cell compartment. In some embodiments, the device includes a series of coculture chambers, which include a neuron chamber featuring retaining pillars acting as a cup for the neurospheres, a muscle cell culture compartment including one or more compliant anchor pillars for muscular tissue to wrap around, and a buffer compartment separating the neuronal cell compartment and the muscle cell compartment. In certain embodiments, two large reservoirs flank the tissue culture chambers (e.g., the neuronal cell compartment and the muscle cell compartment) and allow for the supply of medium and chemical cues.

When the device is seeded with muscle cells and appropriate conditions are applied, a muscle bundle may form in the muscle cell culture compartment and wrap around the compliant pillars. For example, the muscle bundle may wrap around two compliant pillars, and completely span the distance between the compliant pillars. The compliant pillars may, e.g., comprise a cap structure (e.g., in the shape of a square, sphere, slab, or an extension of the pillar bent away from the opposite pillar) or may be continuous from the floor to the ceiling of the chamber so as to prevent the muscle bundle from slipping off the compliant pillars. Likewise, when the device is seeded with neuronal cells, such as neuro spheres, and appropriate conditions applied, neurites may extend out of the neurospheres, navigate through the extracellular matrix across the buffer compartment and reach the muscle bundle, where they form three-dimensional neuromuscular junctions. Upon stimulation of the neuronal cells, the muscle bundle may contract, demonstrating the presence of functional neuromuscular junctions.

A. Culture Compartments and Buffer Chambers

The first culture compartment can have a width of, for example, at least 100 µm. In some embodiments, the width of the first culture compartment is about 100 µm, 500 µm, 1.25 mm, 1.5 mm, 1.75 mm, 2 mm, 2.5 mm, 3 mm, 4 mm, or 5 mm. In some embodiments, the width of the first culture compartment is less than about 500 µm, 1.25 mm, 1.5 mm, 1.75 mm, 2 mm, 2.5 mm, 3 mm, 4 mm, or 5 mm.

The second culture compartment can have a width of, for example, at least 100 µm. In some embodiments, the width of the second culture compartment can be about 100 µm, 500 µm, 1.25 mm, 1.5 mm, 1.75 mm, 2 mm, 2.5 mm, 3 mm, 4 mm, or 5 mm. In some embodiments, the width of the second culture compartment is less than about 500 µm, 1.25 mm, 1.5 mm, 1.75 mm, 2 mm, 2.5 mm, 3 mm, 4 mm, or 5 mm.

In some embodiments, the first culture compartment, the second culture compartment, or the buffer compartment includes a volume of at least 650 $\mu m^3$. In some embodiments, the first culture compartment, the second culture compartment, or the buffer compartment includes a volume of about 650 $\mu m^3$, 700 $\mu m^3$, 750 $\mu m^3$, 800 $\mu m^3$, 850 $\mu m^3$, 900 $\mu m^3$, 950 $\mu m^3$, 1600 $\mu m^3$, or 2100 $\mu m^3$.

An escape channel can be included between an end of the second chamber and a reservoir, the escape channel allowing passage of gas or excess gel solution during a hydrogel injection process.

Unlike conventional two-dimensional cell monolayer systems, the microfluidic device described herein enables coculture of neurospheres and muscle bundles and allows for the formation of three-dimensional neuromuscular junctions in a microenvironment that mimics that of an in vivo counterpart. The microfluidic device or platform provides three dimensional and compartmentalized coculture. Spatial segregation of the two cell types provides a unique opportunity to visualize the three-dimensional axon outgrowth towards the muscle. In various embodiments, the three dimensional coculture of cells comprises one or more hydrogels. In addition, the microfluidic device enables quantitative measurement of force generated by muscle tissues. The presence of several identical coculture chambers per microfluidic device and the geometrical configuration matching the dimensions of multichannel pipettors facilitates formation of multiple parallel cultures in order to increase throughput while maintaining a user friendly seeding procedure. Further, the microfluidic device allows for the generation of chemical cues in the form of concentration gradients, capable of emulating a distribution of factors as found in the body.

The microfluidic devices permit repeatable and precise positioning of the motor neuron containing neurospheres with respect to the muscle bundle, which reduces experimental sample-to-sample variation. For example, the integrated compliant pillar technology can be a means to non-invasively and passively measure the force generated by the muscle bundle. The presence of the hydrogel all around the neurospheres and muscle bundles not only provides a physical bridge to allow for axon outgrowth towards their muscle target, but it recapitulates the compliant and extracellular matrix (ECM) rich microenvironment encountered in vivo.

In some embodiments, the device includes a plurality of co-culture chambers that are separate from one another. Thus, each chamber can be manipulated (e.g., filled with different materials) independently. Moreover, the design and manufacture of the device is simplified. The separate nature of the muscle chamber along with an entry necking region results in individual untethered and freely moving muscle tissues.

In some embodiments, the device includes a muscle chamber shaped so that hydrogel injected (in its liquid state) can be pushed to the limit of the muscle chamber, and not further. An escape channel, which may be formed as small L-shaped channel, evacuates any air bubble that might form during the hydrogel injection process. The dead-end nature of the muscle chamber along with a constriction feature or entry necking region results in individual untethered and freely moving muscle tissues.

The microfluidic device provides an ability to provide cell-specific media or generate gradients of growth factors, in order to mimic the chemical microenvironment found in vivo. Moreover, the composition of the hydrogel (mimicking an extracellular matrix) can be tuned to include some ligands of interest or to vary the mechanical properties, so long as axon formation is not prevented. Finally, the use of microfluidic devices of the present subject matter for such cell culture allows cell maintenance, treatment, and image acquisition to be automated.

Microfluidic devices can be used for coculture of muscle cells and neuronal cells for innervating a muscle bundle with an axon. The microfluidic device includes a coculture chamber including a first culture compartment, a second culture compartment, and a buffer compartment. The first culture compartment includes one or more retaining features. The second culture compartment includes one or more compliant pillars. The buffer compartment separates the first compartment and the second compartment. The compliant pillars are deflectable to measure force generated by the muscle bundle.

In various embodiments, a "buffer compartment" refers to a compartment between a compartment that contains neuronal cells and a compartment that contains muscle cells. The buffer compartment need not contain a different hydrogel or buffer (pH-balanced solution) than any other compartment. For example, the buffer compartment may be a region that is filled with the same hydrogel that is used to culture/surround the neurons and the muscle cells. Thus, in various embodiments, the purpose of the "buffer compartment" is to physically segregate the neurons from the muscle and offer a window/region for visualizing axonal outgrowth. Without the buffer compartment, the muscle chamber would be directly adjacent to the neuron chamber, and natural tissue spreading could result in direct contact between the neuronal cells and muscle cells.

One or more of the features can be included in a device in any feasible combination. For example, in some embodiments, retaining features can include rigid pillars positioned in a substantially concave arrangement, the first culture compartment can contain a neuronal cell culture, the second culture compartment can contain a muscle cell culture, and the buffer compartment can contain a hydrogel but no cells, or cells other than the muscle and neuronal cells. An axon can extend from the first culture compartment through the buffer compartment to the second culture compartment and form a neuromuscular junction with the muscle cells. The first culture compartment, the second culture compartment, and/or the buffer compartment can contain a hydrogel.

In some embodiments, the microfluidic device includes one or more neuronal inlet injection ports for seeding the first culture compartment with neuronal cells. One or more muscle inlet injection ports can be included for seeding the second culture compartment with muscle cells.

In various embodiments, a microfluidic device can include a plurality of coculture chambers, the coculture chambers being separated from each other by the minimal tip distance between the individual pipettes of a multichannel pipettor. The use of a multichannel pipettor facilitates multiplexing cell culture maintenance and treatment administration. In some embodiments, the plurality of coculture chambers includes six or more coculture chambers.

In certain embodiments, the microfluidic device includes a first medium reservoir adjacent the first culture compartment, and a second medium reservoir adjacent the second culture compartment. When filled with culture medium, these reservoirs allow for, e.g., the supply of nutrients, the removal of waste and the administration of chemical cues. If two distinct conditions are supplied to the first and second reservoirs, chemical concentration gradients will form by diffusion within the hydrogel and expose each compartment to a specific condition.

The second culture compartment can be seeded with muscle cells to enable growth of the muscle bundle. The muscle bundle can wrap around the compliant pillars. The first culture compartment can be seeded with neuronal cells to enable growth of the neurites from the first culture compartment through the buffer compartment to the second culture compartment and form neuromuscular junctions with the muscle bundle. The neuronal cells can be stimulated. When functional neuromuscular junctions are present, the stimulation of the neuronal cells can elicit the contraction of the muscle bundle. The contraction of the muscle bundle causes deflection of the compliant pillars around which it is wrapped. The amount of deflection can be converted into a level of force generated by the muscle bundle, providing that the mechanical stiffness of the pillars is known.

Other means of measuring forces generated by the muscle bundles can also be substituted for, or combined with, the pillars. For example, pressure, tension, strain or deflection sensors, devices or structures for measuring changes in the force can be incorporated into the pillars or support structure that are activated by movement of the pillars, support structure or sides of the device, as a result of movement of the muscle bundles. Instead of pillars, one could have rings anchored to the substrate through which the muscle bundles migrate, and then move in response to movement of the muscle bundles. Other structures would be apparent to those skilled in the art.

In some embodiments, a microfluidic device for coculture of muscle cells and neuronal cells includes a coculture chamber including a first culture compartment including one or more retaining features; a second culture compartment including one or more compliant pillars; and a buffer compartment separating the first compartment and the second compartment; wherein the compliant pillars are deflectable to measure force. In various embodiments, the device is for innervating a muscle bundle formed by muscle cells and measuring force generated by the muscle bundle alone or at the time of or after exposure to an agent such as a drug or diagnostic agent, or mechanical or electrical stimuli.

In some embodiments, the muscle bundle is innervated by one or more of (a) growth of neurites into contact with the external surface of the muscle bundle; (b) growth of neurites past the external surface and into the muscle bundle; and/or (c) formation of a neuromuscular junction between an axon and a muscle cell of the muscle bundle.

In some embodiments, the one or more retaining features includes a rigid substantially concave barrier.

In some embodiments, the barrier includes (a) about 1, 2, 3, 4, 5, 6, 7, 8, 9, 10 or more are pillars or plates positioned in a substantially concave arrangement; or (b) a substantially concave wall with slits, holes, or openings too small for a neuron or neurosphere to pass through but large enough for an axon to pass through.

In some embodiments, the first culture compartment contains at least one neuronal cell, the second culture compartment contains at least one muscle cell, and the buffer compartment contains a hydrogel. In some embodiments, the first culture compartment, the second culture compartment, and the buffer compartment contain a hydrogel. In some embodiments, the first culture compartment, the second culture compartment, and the buffer compartment contain the same hydrogel. In some embodiments, the hydrogel in the first culture compartment, the second culture compartment, and/or the buffer compartment contains a cell other than the neuronal cell or the muscle cell. In some embodiments, the cell is a Schwann cell, a satellite cell, an endothelial cell, and/or a glial cell.

In some embodiments, the device includes one or more neuronal inlet injection ports for seeding the first culture compartment with neuronal cells. In some embodiments, the device includes one or more muscle inlet injection ports for seeding the second culture compartment with muscle cells.

In some embodiments, the device includes a plurality of coculture chambers. For example, in some embodiments, the plurality of coculture chambers includes about 5, 6, 7, 8, 9, 10, 15, 20, 25 or more coculture chambers.

In some embodiments, each coculture chamber includes a neuronal inlet injection port for seeding the first culture compartment with neuronal cells, and the distance between each neuronal inlet injection port is the distance between the pipettes of a multichannel pipettor.

In some embodiments, each coculture chamber includes a muscle inlet injection port for seeding the second culture compartment with muscle cells, and the distance between each muscle inlet injection port is the distance between the pipettes of a multichannel pipettor.

In some embodiments, the device includes a first medium reservoir adjacent the first culture compartment; and a second medium reservoir adjacent the second culture compartment, the first and second medium reservoirs enabling generation of gradients of growth factors.

In some embodiments, the first culture compartment, the second culture compartment, and/or the buffer compartment include a hydrogel.

B. Cells

Cells for use in the systems are also provided. For example, the device can be used to form innervated muscle bundles (referred to herein as 3D motor units). The 3D motor units typically include at least nerve cells and muscle cells, but may also include additional cells including, but not limited to, astrocytes, Schwann cells, endothelial cells, etc. as discussed in more detail below.

Cells are optionally enriched for a particular cell type. For example, a neuronal cell or a muscle cell, or a complex of neuronal cell and a muscle cell together can be enriched. In some embodiments, a cell or population of cells are purified or isolated. An isolated cell, population of cells, other entity or substance is produced, prepared, purified, and/or manufactured by intervention by a human being (the hand of man). For example, isolated cells can be separated from at least about 10%, about 20%, about 30%, about 40%, about 50%, about 60%, about 70%, about 80%, about 90%, about 95%, about 96%, about 97%, about 98%, about 99% or more of the other components with which they were initially associated in a natural state (e.g., by weight, such as dry weight).

In some embodiments, an isolated cell or a population of isolated cells are more than about 80%, about 85%, about 90%, about 91%, about 92%, about 93%, about 94%, about 95%, about 96%, about 97%, about 98%, about 99%, or more than about 99% pure (e.g., by weight, such as dry weight). As used herein, a substance is "pure" if it is substantially free of other components. In the case of a purified cell or population of purified cells of a particular type (e.g., phenotype or genotype), the cell or population is substantially pure of cells of another type (e.g., phenotype or genotype). A co-culture includes at least 2 different cell types, e.g., a co-culture may include both a neuronal cell and a muscle cell, e.g. a neuromuscular junction formed in the hydrogel of the device.

Any of the cells can harbor one or more mutations. Particularly preferred mutations are associated with the diseases and disorders discussed herein. Neural cells derived from induced pluripotent stem cells isolated from a patient with ALS are exemplified below. However, cells can also be isolated from individuals with other disease or disorders. For example, because Alzheimer's disease, Parkinson's disease, and epilepsy have been associated with muscle strength (Boyle et al., *Arch. Neurol.* 66, 1339-1344 (2009), Cano-de-la-Cuerda et al., *Am. J. Phys. Med. Rehabil.* 89, 70-76 (2010)) coculture with iPSC-derived cortical neurons from these patients would facilitate investigations of the relationship between these pathologies and muscle strength.

When patient-derived skeletal muscle cells (Darabi et al., *Cell Stem Cell* 10, 610-619 (2012)) and/or are used it is believed that the model can be applied not only to neuropathy (such as that associated with ALS and spinal muscular atrophy) but also to myopathy (such as that associated with Duchenne muscular dystrophy and myasthenia gravis) by forming patient-derived muscle fiber bundles to investigate interactions between muscle atrophy and MN activity and drug testing.

Other exemplary diseases and disorders are discussed elsewhere herein and in more detail below.

Any of the cells can be transfected with gene expression constructs or gene editing technology. For example, in the experiments below, optogenetics technology based on transfection of a light-sensitive ion channel gene, channelrhodopsin-2[H134R], into iALS-MNs and control cells [embryonic stem (ES) derived] facilitated spatiotemporal control of neural activity and muscle contractions. Thus, in some embodiments, the neuronal cells are transfected with channelrhodopsin-2 making the neuronal cells photosensitive.

In some embodiments the cells are transfected with gene editing technology, such as CRISPR/Cas9, to induce mutations (including SNP, insertion or deletion of gene sequences) in healthy cells, or correct or otherwise rescue a mutation in diseased cells. Particularly preferred mutations are associated with the diseases and disorders discussed herein.

1. Neurospheres and Neurons

The systems typically include one or more neural cells. In some embodiments, the neural cell is a patient-derived neural cell. In some embodiments, the patient-derived neural cell is from a patient who has been diagnosed with amyotrophic lateral sclerosis (ALS), spinal muscular atrophy (SMA), or one of the other diseases or disorders discussed herein, or another unmentioned neural or muscular or neurodegenerative disease or disorder. The neural cell can be a neuronal cell or induced or otherwise differentiated to form a neuronal cell.

For example, in some embodiments, the neuronal cell (a) is within a neurosphere; (b) is a neural stem cell; (c) is a neural progenitor cell; (d) is a neural precursor cell (NPCs); (e) is a neuron; (f) is an interneuron; (g) is a sensory neuron; and/or (h) is a motor neuron.

In various embodiments, a neurosphere can range between 100 µm to 2 mm in diameter. In some embodiments, a neurosphere contains about 1,000 to 1,000,000 or more cells. Neuronal cells and muscle cells may be cultured, e.g., in a hydrogel. The hydrogel material may be the same throughout each coculture chamber (e.g., in the first, second, and buffer compartments). In some embodiments, when the muscle chamber is seeded, the hydrogel contains between 2,000,000 to 10,000,000 cells/ml of hydrogel. In certain embodiments in which the muscle chamber has a volume of about one microliter, the chamber may initially contain, e.g., about 2,000 to 10,000 cells.

Non-limiting examples of neurons that may be include cells forming neuromuscular junctions with muscle cells in primary tissue; spinal cord explants; and autonomic ganglia.

In some embodiments, the neurons start as heathy or diseased embryonic or induced pluripotent stem cells. Methods for isolating, differentiating, and culturing neural stem cells, including from embryonic and induced pluripotent stem cells are known in the art and discussed in, for example, Lee, et al., "Mini-Review: Neural Stem Cells," STEMCELL™ Technologies, DOCUMENT #29019 VERSION 5.0.0 April 2015.

Motor neurons can also be genetically manipulated to express progerin to simulate premature aging (Miller et al., Cell Stem Cell 13, 691-705 (2013)).

Additionally or alternatively, direct differentiation into MNs from patient-derived somatic cells is possible by ensuring transgenic expression of transcription factors that induce MN differentiation (Son et al., Cell Stem Cell 9, 205-218 (2011)) and by inducing microRNAs (Abernathy et al., Cell Stem Cell 21, 332-348.e9 (2017)). In addition, inhibition of the Notch pathway has been shown to accelerate MN differentiation by delaying the cell cycle transition from G1 to S phase (Maury et al., Nat. Biotechnol. 33, 89-96 (2015)). These technologies can create a more mature 3D ALS model.

Axons can grow to be several millimeters long in vitro, including in devices of the present subject matter (and up to about a meter in vivo). Axons have been observed extending at a maximum rate of about 10 micron/hour. Axons may extend in all directions.

In some embodiments, a device or chamber of a device includes one or more factors that attracts and/or repels axons. For example, Netrin and nerve growth factor (NGF) are examples of soluble chemoattractants, and Slit or semaphorins are known chemorepellants. Glial cell-derived neurotrophic factor (GDNF) was found to increase the rate of axon outgrowth. In addition, one or more factors that attracts and/or repels axons can be applied in a gradient using the two medium reservoirs.

In preferred embodiments, neural cells begin as embryonic or induced pluripotent neural stem cells originally isolated from a diseased subject. The cells are induced to form neural stem spheroids, motor neuron progenitor spheroids, and motor neuron spheroids before seeding on the devices as a neurosphere. See, e.g., FIG. 1G.

In some embodiments, the neurosphere (a) includes about 1 to 1000, 100,000 to 10,000,000, 1000 to 1,000,000, or more than 1,000,000 neurons; (b) includes a dimension of about 50-2000 microns at its widest diameter; (c) includes embryonic neural stem cells; (d) includes induced pluripotent neural stem cells; and/or (e) includes a neuron, an astrocyte, and/or an oligodendrocyte.

2. Muscle Cells

The system typically includes one or more muscle cells. In some embodiments, the muscle cell is a patient-derived muscle cell. In some embodiments, the patient-derived muscle cell is from a patient who has been diagnosed with muscular dystrophy, or other neural, muscular or neurodegenerative disease or disorder. In some embodiments, the muscle cell (a) is within a muscle bundle; (b) includes a myoblast; and/or (c) includes a cardiac, skeletal, or smooth muscle cell.

In some embodiments, the muscle bundle (a) includes about 1 to 1000, 1000 to 10,000, 1 to 20,000, or at least about 1000, 5000, or 10,000 muscle cells; (b) is about 0.5, 1, 2, 3, 4, 5, 2 to 3 or 0.05-5 mm long; and/or (c) includes a cardiac, skeletal, and/or smooth muscle cell.

Non-limiting examples of muscle cells that may be used in various embodiments include cells dissociated from organs constituting the muscular system, such as from the heart (cardiac cells), limb or body wall muscles (skeletal muscle cells), and visceral muscle (smooth muscle cells).

In some embodiments, cells that have been differentiated from pluripotent cells (e.g., muscle cells derived from embryonic stem cells or induced pluripotent stem cells).

In some embodiments, the axon extends from the first culture compartment through the buffer compartment to the second culture compartment and forms a three-dimensional neuromuscular junction with the muscle cells.

3. Additional Cells

In addition to neurons and muscle cells, any of the culture systems can further include one or more additional cell types. Any of the additional cell types can be healthy or diseased patient-derived cells. In some embodiments, the patient-derived cells are from a patient who has been diagnosed with one of the neural or muscular or neurodegenerative disease or disorder described herein.

a. Endothelial Cells

In some embodiments, particularly those in which the system is utilized for drug testing or screening, the system further includes endothelial cells, and preferably includes an endothelial barrier formed from the endothelial cells.

Non-limiting examples of endothelial cells that may be used in various embodiments include cells dissociated from human umbilical vein (human umbilical vein endothelial cells (HUVECs)) as well as large and microvascular vessels in the human body. Cells can be harvested from large vessels, such as the aorta or saphenous vein, capillaries (e.g., human brain microvascular ECs (HMVEC)). HMVECs differ in morphology and properties according to the tissues supplied by the capillaries and can be isolated from dermal, lung, cardiac, uterine, brain, and spinal cord tissues, among others.

In some embodiments, cells that have been differentiated from pluripotent cells (e.g., endothelial cells derived from embryonic stem cells or induced pluripotent stem cells) can be used.

In preferred embodiments, the cells begin as embryonic or induced pluripotent endothelial cells originally isolated from a heathy or diseased subject. In the experiments below, iPSC-derived ECs (iECs) created a barrier layer as they differentiated toward a brain-specific EC phenotype following the addition of retinoic acid (RA). See, e.g., (Lippmann et al., *Sci. Rep.* 4, 4160 (2014)).

b. Other Cell Types Although excess glutamic acid-induced MN excitotoxicity was observed in the motor unit model, when astrocytes were cocultured with MNs and skeletal muscle cells, the glutamate concentration threshold increased. This indicates that the addition of glial cells might be helpful in some culture models. Thus, in some embodiments, the system further includes astrocytes, glial cells, or a combination thereof.

In addition to the improvement of MN characterization and differentiation, it is believed that the inclusion of other types of cells such as Schwann cells and microvascular networks can be utilized to obtain an even more robust motor unit. During the developmental process and to maintain homeostasis, Schwann cells regulate MN nerve fiber myelination, improve axonal outgrowth, and have therapeutic potential for spinal cord injury.

Moreover, perfusable microvascular networks involving ECs in the microfluidic device would be advantageous for long-term maintenance of the ALS, and other similar motor unit disease models. They would improve the supply of oxygen and nutrients to the tissues and better mimic the delivery of drug to the CNS. A previously described coculture model with MN spheroids and perfusable vascular networks in microfluidic devices resulted in improved neural networks and culture medium perfusion to improve MN activity (Osaki et al., *Sci. Rep.* 8, 5168 (2018)). Furthermore, vascular networks not only are physiologically relevant but also play an important role in the pathogenesis of ALS, which is accompanied by vascular dysfunction and impaired blood-tissue barrier function (Garbuzova-Davis et al., *Brain Res.* 1469, 114-128 (2012), Winkler et al., *Proc. Natl. Acad. Sci. U.S.A.* 111, E1035-E1042(2014)).

C. Pillars

Compliant pillars can be made in different forms, with different cap structures (plates, spheres, extensions), as well as by using different methods (casting from a 3D printed mold, bending of a longer pillar, deformation of the top of the pillar).

The compliant pillars are deflectable and when wrapped by the muscle bundle will deflect when the muscle bundle contracts. Deflection of the compliant pillars allows for measurement of the force generated by the muscle bundle when the muscle bundle contracts. These integrated compliant pillars are a means to non-invasively and passively measure the force generated by the muscle bundle.

The compliant pillars are deflectable/deformable. For example, the stiffness of exemplary posts was found to be approximately $0.36 \pm 0.08$ $\mu N \mu m^{-1}$. Stiffness of the pillar(s) can vary. As a non-limiting example, the stiffness can vary between about $0.20$ $\mu N \mu m^{-1}$ and about $0.50$ $\mu N \mu m^{-1}$, and more preferably between about $0.28$ $\mu N \mu m^{-1}$ and about $0.45$ $\mu N \mu Z^{-1}$. The Young's modulus of material(s) of the pillar(s) can also vary, as well. For example, the Young's modulus can vary between about 500 kPa to about 1.5 MPa, and more preferably about 580 kPa to about 1 MPa. Deflection(s) of the pillar(s) can be measured between a variety of values. As a non-limiting example, deflection can be measured between about 0.1 μm and about 200 μm, and more preferably between about 0.1 μm and about 50 μm.

In some embodiments, the one or more compliant pillars have a height of at least 50 μm. In some embodiments, the height is about 50 μm, 100 μm, 150 μm, 250 μm, 260 μm, 270 μm, 280 μm, 290 μm, 300 μm, 310 μm, 320 μm, 330 μm, 340 μm, 350 μm, 1 mm, or 1.5 mm. In some embodiments, the height is less than 100 μm, 150 μm, 250 μm, 260 μm, 270 μm, 280 μm, 290 μm, 300 μm, 310 μm, 320 μm, 330 μm, 340 μm, 350 μm, 1 mm, or 1.5 mm.

D. Valves

In certain embodiments, the device comprises a system of valves. The valves may, e.g., allow for a desired coculture chamber or chamber compartment (or a plurality thereof) to be modified individually. The system of valves allows for the formation of several (for example, six, seven, eight, nine, ten, or more) mechanically decoupled individual muscle bundles. In various embodiments, the microfluidic device can include a first layer including the coculture chamber and a control layer including a valve system. In some embodiments, a microfluidic device can include a plurality of coculture chambers, a channel connecting the plurality of coculture chambers, and a valve system separating the plurality of coculture chambers. An evacuation channel can be included that, when a vacuum is applied to the evacuation channel, aspirates tissue remaining in the channel connecting the plurality of cocultures.

In some embodiments, a channel on the first layer may connect multiple coculture chambers and enable simultaneous seeding of muscle cell culture compartments. In certain embodiments, the valve system serves to selectively separate the coculture chambers. The first layer may include an evacuation channel for aspirating tissue (e.g., by applying a vacuum) remaining in the channel after seeding the muscle cell culture compartments.

In various embodiments, in order to seed a muscle cell and hydrogel mix into the muscle cell compartments of the microfluidic device in one single procedure, while allowing for mechanical isolation of each to-be-formed muscle bundle, the system of closed-at-rest valves can lift ceiling membranes above each muscle compartment wall. When a vacuum is applied to the microfluidic device, the ceiling raises above the walls, letting a liquid mix of hydrogel and muscle cells to flow along channel, filling all 6 muscle cell culture compartments at once. When vacuum is released, the ceilings come down and isolate each coculture chamber from its neighbors before the hydrogel is allowed to polymerize. The evacuation channel enables for the aspiration of the tissue remaining in any intermediate chambers in between muscle culture chambers.

E. Hydrogel Compositions

In some embodiments, the first culture compartment, the second culture compartment, the buffer compartment, and/or other compartments or surfaces of the device include a hydrogel.

Hydrogel compositions encompass a group of polymeric materials, the hydrophilic structure of which renders them capable of holding large amounts of water in their three-dimensional networks. Polymers from which hydrogels are made may be naturally-occurring, e.g., purified from a natural source, or synthetic, e.g., chemically-synthesized. The polymers may be water soluble or water insoluble. The ability of hydrogels to absorb water arises from hydrophilic functional groups attached to the polymeric backbone, while their resistance to dissolution arises from cross-links between network chains.

Thus, in some embodiments, the hydrogel is crosslinked. In some embodiments, the hydrogel has been crosslinked or may be crosslinked by temperature-induced crosslinking, photocrosslinking, or enzymatic crosslinking. The cross-links may be chemical or physical; polymer crosslinks include covalent crosslinks, ionic crosslinks, hydrogen bonds, and/or hydrophobic interactions. Hydrogel-forming natural polymers include purified proteins such as collagen and gelatin and purified polysaccharides such as starch, alginate, and agarose. Synthetic polymers that form hydrogels are prepared using chemical polymerization/synthesis methods. Hydrogels may be one, two- or multi-component systems consisting of a three-dimensional network of polymer chains and water that fills the space between polymer macromolecules.

In some embodiments, hydrogel can include a network of polymer chains that are water-insoluble. Hydrogel can include a water-swollen and cross-linked polymeric network produced by a reaction of one or more monomers. Hydrogel can include polymeric material that exhibits the ability to swell and retain a significant fraction of water within its structure, but will not dissolve in water. Hydrogel can include a colloidal gel in which water is the dispersion medium. Their hydrophilic structure renders them capable of holding large amounts of water in their three-dimensional networks (e.g., hydrogels can be super absorbent and can contain 50%, 75%, 90%, 95% and over 99% water). Hydrogels can include natural and/or synthetic polymers. Hydrogels can possess a degree of flexibility very similar to natural tissue, due to their significant water content.

In a non-limiting example, a hydrogel includes collagen. Various concentrations of collagen may be used. For example, a concentration of about 1, 2, 3, 4, 5, 6, 7, 8, 9, 10, or 1-10 mg/ml or more of collagen in an aqueous solution (such as cell culture medium, saline, or water) may be used. The collagen-containing hydrogel optionally also includes one or more of the following proteins: laminin, entactin, heparan sulfate proteoglycans, which are characterized by adhesive properties, as well as growth factors such as TGF-beta and EGF. An example of such a collagen-containing hydrogel includes MATRIGEL. Thus in some embodiments, the hydrogel includes MATRIGEL (gelatinous protein mixture derived from mouse tumor cells) or an equivalent thereof. MATRIGEL is the trade name for a gelatinous protein mixture secreted by Engelbreth-Holm-Swarm (EHS) mouse sarcoma cells that is produced and marketed by Corning Life Sciences. Thus "MATRIGEL" may be substituted with a gelatinous protein mixture from another natural, synthetic, or commercial source. MATRIGEL or a substitute of MATRIGEL may be used, e.g., in a 1:1, 1:2, 1:3, 1:4, 1:5, 1:6, 1:7, 1:8, 1:9, 1:10 MATRIGEL: collagen or collagen:MATRIGEL ratio.

In some embodiments, the hydrogel includes an alginate or a derivative thereof, gelatin, collagen, agarose, a natural or synthetic polysaccharide, polylactic acid, polyglycolic acid, poly(lysine), a polyanhydride; a poly(lactide-co-glycolide) (PLGA) polymer, a polyamino acid, a poly(alkylene oxide), a poly(ethylene oxide), a poly(allylamine)(PAM), a poly(acrylate), a polyester, polyhydroxybutyrate and poly-epsilon-caprolactone, a polyphosphazine, a poly(vinyl alcohol), a modified styrene polymer, poly(4-aminomethylstyrene), a pluronic polyol, a polyoxamer, a poly(uronic acid), a poly(vinylpyrrolidone), and/or a copolymer including one or more of an alginate or a derivative thereof, gelatin, collagen, agarose, a natural or synthetic polysaccharide, polylactic acid, polyglycolic acid, poly(lysine), a polyanhydride; a poly(lactide-co-glycolide) (PLGA) polymer, a polyamino acid, a poly(alkylene oxide), a poly(ethylene oxide), a poly(allylamine)(PAM), a poly(acrylate), a polyester, polyhydroxybutyrate and poly-epsilon-caprolactone, a polyphosphazine, a poly(vinyl alcohol), a modified styrene polymer, poly(4-aminomethylstyrene), a pluronic polyol, a polyoxamer, a poly(uronic acid), and a poly(vinylpyrrolidone).

III. Methods of Use

Methods of using microfluidic devices are also provided. The methods can include seeding the second culture compartment with muscle cells to enable growth of the muscle bundle, the muscle bundle wrapping around the compliant pillars; and seeding the first culture compartment with neuronal cells to enable growth of the axon to extend from the first culture compartment through the buffer compartment to the second culture compartment and form a neuromuscular junction with the muscle bundle.

In some embodiments, the method includes stimulating the neuronal cells and measuring deflection of the compliant pillars that result from contraction of the muscle bundle, the contraction caused by the stimulation of the neuronal cells.

In some embodiments, the muscle cells include myoblasts. Myoblasts can be stimulated with media comprising about 1, 1.5, 2, 2.5, 3, 3.5, 4, 4.5, or 5% horse serum to induce myoblast fusion and skeletal muscle differentiation.

Methods of assessing muscle or motor neuron function, including providing a microfluidic device, and stimulating the neuronal cells, are also provided.

In some embodiments, the microfluidic device includes a test compound.

In some embodiments, the test compound includes a drug candidate.

The test compound can be a small molecule, for example an organic compound having a molecular weight less than 1000 or 2000 daltons, an RNA interference molecule, a protein, a peptide, an antibody, an antibody fragment, or an aptamer.

The medium can have a first concentration added to a first medium reservoir adjacent to the first culture compartment to generate a gradient medium within the coculture chamber.

In some embodiments, a second medium having a second concentration is added to a second medium reservoir adjacent the second culture compartment.

A. Physiological Model of Human Motor Unit

The materials can be used to generate a physiological model of the human motor unit. For example, the human motor unit can be formed of disease or non-disease derived neurons in combination with disease or non-disease derived muscle cells alone or in further combination with disease or no disease derived endothelial cells optionally additional disease or non-disease derived cell such as astrocytes, glial cells, Schwann cell, vascular endothelium, etc.

The system can be used to study neuronal and/or muscular diseases and test treatments for diseases and disorders including, but not limited to, diseases caused by faulty genes, such as amyotrophic lateral sclerosis (ALS), Huntington's disease (HD), and muscular dystrophies, problems with the way the nervous system develops, such as spina bifida, degenerative diseases, where nerve cells are damaged or die, such as Parkinson's disease (PD) and PD-related disorders and Alzheimer's disease (AD) and other dementias, diseases of the blood vessels that supply the brain, such as stroke, injuries to nerves or muscle, seizure disorders, such as epilepsy, as well as the cancer and infections, such as meningitis. In some embodiments, some or all of the cells in the model are derived from one of the foregoing diseases.

Other exemplary diseases that can be investigated (including drug testing) using the model, and from which some or all of the cells used in the model may be derived include other neurodegenerative diseases including, but not limited to, prion diseases such as Creutzfeldt-Jakob Disease, corticobasal degeneration, frontotemporal dementia, cognitive impairment including mild cognitive impairment and HIV-related cognitive impairment, motor neuron diseases (MND), spinocerebellar ataxia (SCA), spinal muscular atrophy (SMA), Friedreich's Ataxia, Lewy Body Disease, Alpers' Disease, Batten Disease, Cerebro-Oculo-Facio-Skeletal Syndrome, Corticobasal Degeneration, Gerstmann-Straussler-Scheinker Disease, Kuru, Leigh's Disease, monomelic amyotrophy, multiple system atrophy, multiple system atrophy with orthostatic hypotension (Shy-Drager Syndrome), Multiple Sclerosis (MS), neurodegeneration (e.g., with brain iron accumulation), opsoclonus myoclonus, posterior cortical atrophy, primary progressive aphasia, progressive supranuclear palsy, vascular dementia, progressive multifocal leukoencephalopathy, dementia with Lewy Bodies, lacunar syndromes, hydrocephalus, Wernicke-Korsakoff's syndrome, post-encephalitic dementia, cancer and chemotherapy-associated cognitive impairment and dementia, and depression-induced dementia, Guillain-Barré syndrome, and pseudodementia.

The system is particularly advantageous for investigating simulation of human physiological and pathological conditions associated with motor units and neuromuscular junctions. Thus, in particularly preferred embodiments, the disease is a neuromuscular disorder such as ALS, a muscular dystrophy, myasthenia gravis, or spinal or bulbar muscular atrophy. Muscular dystrophy is a group of diseases that cause progressive weakness and loss of muscle mass. In muscular dystrophy, mutations typically interfere with the production of proteins needed to form healthy muscle. There are many different kinds of muscular dystrophy, including, for example, Duchenne type muscular dystrophy and Becker muscular dystrophy.

In some embodiments, the neurons, muscle cells, and/or other cells in the model in any combination thereof are derived from patients suffering from a neurological disease, a muscular disease, or most preferably a neuromuscular disease. In particular embodiments, the patient has one or more mutations that effect the function of neurons or muscle cells in the subject. Particularly preferred examples are ALS, a muscular dystrophy, myasthenia gravis, or spinal muscular atrophy.

Figure 1B:
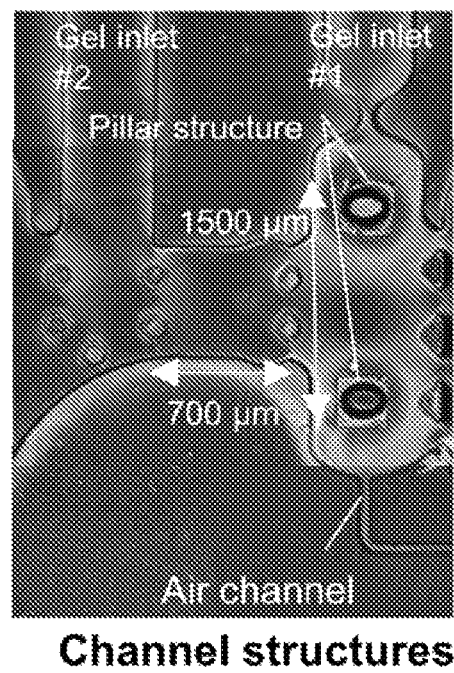
FIG. 1B is an image of the microfluidic device of FIG. 1A. Each device has three distinct culture regions: for MN spheroids (left), muscle tissues (right), and neurite elongation (middle). The distance between two pillars is 1500 μm.

The Examples below illustrate how the materials can be used to generate a physiological model of the human motor unit exemplified using ALS and non-ALS patient-derived MNs and iPSC-derived skeletal muscle cells. The flow chart in FIG. 1G illustrates an exemplary embodiment wherein human induced pluripotent stem cells are used as a source of skeletal muscle cells, and human embryonic stem cells (e.g., healthy or wild-type) or human induced pluripotent stem cells (e.g., derived from a patient with ALS) are used a source for motor neuron spheroids. In the most preferred embodiments, the cells are human cells derived from patients with confirmed disease.

The examples below demonstrate the model's robustness as an accurate physiological model that can generate neuromuscular junctions (NMJs), wherein muscle contraction force and the synchronicity of Ca2+ transients and muscle contraction after chemically induced stimulation of the MN can be measured.

In the experiments below, an ALS motor unit model was established by using iALS-MN spheroids and iPSC-derived skeletal muscle cells. MN viability and muscle contraction was tested using optical stimulation.

B. Mimicking Diseased Conditions with Health Cells

The system can be used to screen or test for compounds that induce a disease or disordered state (e.g. neuro- or muscular-toxins), as well as which may have a therapeutic or prophylactic effect.

The system can be used to monitor the physiological, phenotypic, morphological, or molecular condition of the cells over time, including during induction of the diseased state and recovery therefrom. Examples of features of the 3D motor unit model and/or neuromuscular junction that can be monitored include, but are not limited to, growth, morphology, marker expression (e.g., islet1, ChAT, SMI-32, Synapsin I, ATG5, ATG7, ATG16L2, BECN1, ULK1, ULK2, LC3, MYHI, MYHII, MYLII, etc.), contractile force, neuronal soma size, apoptosis (e.g., caspase3/7), autophagy, neurite elongation speed and distance, motor unit and NMJ formation, synaptic activity, secretion of ciliary neurotrophic factor (CNTF), and inflammation (such as by monitoring expression levels of NF-κB, tumor necrosis factor-α (TNF-α), interleukin family proteins, and cyclooxygenase-2. Monitoring techniques include RT-PCR, Western blotting, immunofluorescence; $Ca^{2+}$ imaging;

In some embodiments, a known neurotoxin and/or muscular toxin is added to the system and its effect(s) on the cells is monitored. The experiments below show that excess glutamic acid induced excitotoxicity that mimicked the pathological conditions of ALS. The treatment caused regression of thick neurite fibers, resulting in a weak muscle contraction force, and long-term MN excitotoxicity (after exposure to glutamic acid for 14 days) also causes muscle atrophy due to continuous muscle contraction and muscle fatigue. Tetrodotoxin (TTX) treatment can be used for temporal inhibition of neural activity and muscle contraction. Other neurotoxins that can be used include other nAChR inhibitors, such as curare. These studies show that the 3D motor unit model can be used not only for investigating excitotoxicity (such as that associated with ALS and other MN diseases) but also for carrying out exogenous neurotoxicity studies using various chemical compounds. Such chemically induced models can be used for testing, for example, motor unit neurotoxins and induced disease models such as acquired neuromyotonia.

C. Drug Screening

The system is useful to investigate the activity or applicability of one or more test compounds to treat or alleviate one or more symptoms of a neurological and/or neuromusclular disease or disorder.

In a typical embodiment, cells are cultured under conditions suitable to form a 3D motor unit model and neuromuscular junction. Typically, the cells are isolated from a diseased subject, healthy cells are treated with a disease-inducing compound, to form a diseased, dysfunctional, or defective 3D motor unit model and/or neuromuscular junction.

One or more test compounds can be applied to the culture system and evaluated for the ability to treat one or more symptoms of the diseased, dysfunctional, or defective 3D motor unit model and/or neuromuscular junction. The symptom or symptoms can be specific to the disease state being studied, or can be of a generally nature. Physiological, phenotypic, morphological, or molecular symptoms of the cells can be monitored over time, as discussed above Drug penetration via endothelial cell (EC) barriers (such as the blood-brain barrier and blood-spinal cord barrier) is a consideration when investigating drugs to treat central nervous system (CNS) diseases. Thus, in some embodiments, the system further includes an endothelial cell (EC) layer to generate an EC barrier that mimics the blood-brain barrier and/or blood-spinal cord barrier. For example, in the experiments below, type I collagen gel was poured into the left medium reservoir after injection of motor neuron spheroids. iPS cell-derived endothelial cells (iCell endothelial cells) were then seeded into the left well on the collagen gel. Retinoic acid (RA) was added to accelerate differentiation into brain-specific ECs. The formation of a tight barrier can be confirmed by expression of ZO-1, occludin, and/or P-glycoprotein (P-gp) in the EC monolayer. Low permeability can by confirmed by adding a test agent, e.g., 40-kDa dextran into the reservoir above the EC.

In some embodiments, the culture conditions are modified when endothelial cells are added to the system. See, e.g., FIG. 7A.

After the EC layer is formed, drug can be applied to the reservoir (e.g., the left medium reservoir), to see if it penetrates the EC layer to reach the underlying 3D motor unit model and/or neuromuscular junction. See, e.g., FIG. 7B.

IV. Method of Treatment

Methods of treatment are also provided. Any of the drug candidates identified using the screening methods can be used in a method of treating the symptom(s) or condition(s) for which the drug showed effectiveness in a subject in need thereof. In some embodiments, the subject has a neuronal and/or muscular disease such as ALS, HD, a muscular dystrophy, spina bifida, PD, AD, a disease of the blood vessels that supply the brain, such as stroke, injuries to nerves or muscle, seizure disorders, such as epilepsy, cancer (e.g., brain cancer) an infection, such as meningitis, or a neurodegenerative disorder such as those mentioned above and elsewhere herein. The methods typically include administering a subject in need thereof an effective amount of one or more compounds.

A. Exemplary Co-therapy

The experiments below exemplify how the system can be used for drug screening and/or drug validation, and identify a specific preferred combination therapy for treatment of ALS. Variables that must be considered include dosage, timing of administration, and selection of drugs. Therapies including an mTOR inhibitor and/or a P-gp inhibitor, in combination with a Src/c-Abl pathway inhibitor, and optionally in further combination with one or more additional active agents, were shown to be effective in this model of ALS.

The treatment can include administering to a subject in need thereof an effective amount of mTOR inhibitor and/or P-gp inhibitor, in combination with a Src/c-Abl pathway inhibitor, and optionally in further combination with one or more additional therapeutic, prophylactic or diagnostic agents.

Combination therapy is involved in upregulation of autophagy and/or, p-gp inhibitor. Autophagy upregulation may help reduce or prevent other abnormal aggregation of protein such as amyloid-beta in Alzheimer's disease and α-synuclein in Parkinson's disease. Dosage is important. As shown in studies with using over 1uM in rapamycin and over 800 uM in bosutinib, high concentrations can cause side effects in in vitro co-culture condition. For example, if drug administration is begun before NMJ formation, the drugs also influenced axonal outgrowth negatively in some case. This may be explained by axonal outgrowth need much protein synthesis, but autophagy upregulation prevent new protein synthesis to some extent. Accordingly, timing of administration is important. In this case, drug administration should be initiated after NMJ formation.

Rapamycin is an exemplary mTOR inhibitor and/or P-gp inhibitor. Rapamycin is an mTOR inhibitor with potent immunosuppressive and antiproliferative properties. Rapamycin also decreases the expression of the P-gp transporter, the efflux pump that transports bosutinib and some other drugs out of the CNS. Rapamycin is sold under the tradename RAPAMUNE (sirolimus) in 1 mg/ml liquid formulation as well as 0.5 mg, 1 mg, and 2 mg tablet formulations for oral administration and is FDA approved for prevention of organ transplant rejection and for the treatment of lymphangioleiomyomatosis. See also, for example, U.S. Pat. No. 5,989,591.

In some embodiments, the Src/c-Abl pathway inhibitor is bosutinib. Bosutinib is an ATP-competitive Bcr-Abl tyrosine-kinase inhibitor with an additional inhibitory effect on SRc family kinases (including Src, Lyn and Hck). It has also shown activity against the receptors for platelet derived growth factor and vascular endothelial growth factor. Bosutinib is sold under the tradename BOSULIF and is available in 500-mg and 100-mg tablets for oral administration, and is FDA approved for the treatment of adult patients with Philadelphia chromosome-positive (Ph+) chronic myelogenous leukemia (CML) with resistance, or intolerance to prior therapy. See also, for example, U.S. Pat. Nos. 6,002,008, 7,417,148, 7,767,678, 7,919,625, and RE42,376, which are specifically incorporated herein in their entireties.

In some embodiments, the Src/c-Abl pathway inhibitor is masitinib. Masitinib is a member of the class of benzamides that is the carboxamide resulting from the formal condensation of the carboxy group of 4-[(4-methylpiperazin-1-yl) methyl]benzoic acid with the primary amino group of 4-methyl-N(3)-[4-(pyridin-3-yl)-1,3-thiazol-2-yl]benzene-1,3-diamine. It is a highly selective oral tyrosine kinase inhibitor. It is a N-alkylpiperazine, a member of 1,3-thiazoles, a member of pyridines and a member of benzamides.

Masitinib has been approved for the treatment of mast cell tumors in animals, specifically dogs, and has been distributed under the commercial names MASIVET and KINAVET. The drug was evaluated in a Phase 2/3 clinical trial (NCT02588677) that compared the safety and efficacy of masitinib combined with the approved ALS drug called Rilutek (riluzole). The study included 394 ALS patients treated with either 4.5 mg/kg/day of masitinib and Rilutek, a 3 mg/kg/day of masitinib and Rilutek, or placebo and Rilutek, for up to 48 weeks. Phase 2/3 trial data and data from preclinical studies support the neuroprotective effects of masitinib in ALS are through the targeting of microglial cells. The trial results were published in the Trias, et al., *Journal of Neuroinflammation,* 13:177 (2016) doi: 10.1186/s12974-016-0620-9.

In the experiments below, cotreatment with rapamycin and bosutinib significantly increased muscle contraction force and synchronicity compared with either single agent treatment. Thus, in particularly preferred embodiments, the mTOR inhibitor and/or P-gp inhibitor is rapamycin and the Src/c-Abl pathway inhibitor is bosutinib.

B. Methods of Administration and Dosage Regimes

The combination therapies and treatment regimens include administering to a human in need thereof, an effective amount of an mTOR inhibitor and/or a P-gp inhibitor, in combination with an Src/c-Abl pathway inhibitor, to treat the disease or symptom(s) thereof, or to produce a physiological change, wherein the therapeutic agents are administered together, as part of the same composition, or administered separately and independently at the same time or at different times (i.e., administration of the mTOR inhibitor and/or P-gp inhibitor and Src/c-Abl pathway inhibitor is separated by a finite period of time from each other) and/or different routes. The term "combination" or "combined" is used to refer to either concomitant, simultaneous, or sequential administration of the mTOR inhibitor and/or a P-gp inhibitor and Src/c-Abl pathway inhibitor. The combinations can be administered either concomitantly (e.g., as an admixture), separately but simultaneously (e.g., via separate intravenous lines into the same subject; one agent is given orally while the other agent is given by infusion or injection, etc.,), or sequentially (e.g., one agent is given first followed by the second using the same or different routes of administration).

When administered to treat a neuro- and/or muscular disease such as ALS, the amount of mTOR inhibitor and/or P-gp inhibitor can be the amount effective to improve neuronal survival, increase muscle contraction force, reduce cytoplasmic TDP-43 aggregation, NF-κB expression, and/or skeletal muscle cell apoptosis in muscle fiber bundles, improve motor neuron protection, up-regulate muscle contraction, reduce miscommunication between motor neurons and muscle tissue, induce autophagy, avoid abnormal aggregation of proteins such as TDP-43, or a combination thereof.

The amount of a Src/c-Abl pathway inhibitor can be the amount effective to improve neuronal survival, increase muscle contraction force, reduce cytoplasmic TDP-43 aggregation, NF-κB expression, and/or skeletal muscle cell apoptosis in muscle fiber bundles, improve motor neuron neuroprotection, up-regulate muscle contraction, reduce miscommunication between motor neurons and muscle tissue, induce autophagy, avoid abnormal aggregation of proteins such as TDP-43, or a combination thereof.

In a particular embodiment, a P-gp inhibitor is administered in an effective amount to decrease P-gp transporter in an effective amount to reduce transport of the Src/c-Abl pathway inhibitor out of the CNS, and thus increase the concentration of the Src/c-Abl pathway inhibitor in the brain.

In preferred embodiments, an mTOR inhibitor and/or a P-gp inhibitor, administered in combination with an Src/c-Abl pathway inhibitor, achieves a result greater than when the the mTOR inhibitor and/or a P-gp inhibitor and the Src/c-Abl pathway inhibitor are administered alone. For example, the result achieved by the combination may be partially or completely additive of the results achieved by the individual components alone. In the most preferred embodiments, the result achieved by the combination is more than additive of the results achieved by the individual components alone. In some embodiments, the effective amount of one or both agents used in combination is lower than the effective amount of each agent when administered separately. In some embodiments, the amount of one or both agents when used in the combination therapy is sub-therapeutic when used alone.

A treatment regimen of the combination therapy can include one or multiple administrations of one or more of the compounds. A treatment regimen of the combination therapy can include one or multiple administrations of an mTOR inhibitor and/or a P-gp inhibitor and one or multiple administrations of a Src/c-Abl pathway inhibitor. In certain embodiments, an mTOR inhibitor and/or a P-gp inhibitor and a Src/c-Abl pathway inhibitor are administered to a subject simultaneously. Where an mTOR inhibitor and/or a P-gp inhibitor and a Src/c-Abl pathway inhibitor are administered at the same time, they can be in the same pharmaceutical composition or separate pharmaceutical compositions.

In some embodiments the mTOR inhibitor and/or P-gp inhibitor and Src/c-Abl pathway inhibitor are administered sequentially, for example, in two or more different pharmaceutical compositions. In certain embodiments, the mTOR inhibitor and/or P-gp inhibitor is administered prior to the first administration of the Src/c-Abl pathway inhibitor. In other embodiments, the Src/c-Abl pathway inhibitor is administered prior to the first administration of the mTOR inhibitor and/or P-gp inhibitor. For example, the mTOR inhibitor and/or P-gp inhibitor and an Src/c-Abl pathway inhibitor can be administered to a subject on the same day. Alternatively, the mTOR inhibitor and/or P-gp inhibitor and Src/c-Abl pathway inhibitor are administered to the subject on different days.

The mTOR inhibitor and/or P-gp inhibitor can be administered at least 1, 2, 3, 5, 10, 15, 20, 24 or 30 hours or days prior to or after administering of the Src/c-Abl pathway inhibitor. Alternatively, the Src/c-Abl pathway inhibitor can be administered at least 1, 2, 3, 5, 10, 15, 20, 24 or 30 hours or days prior to or after administering of the mTOR inhibitor and/or P-gp inhibitor. In certain embodiments, additive or more than additive effects of the administration of mTOR inhibitor and/or P-gp inhibitor in combination with Src/c-Abl pathway inhibitor is evident after one day, two days, three days, four days, five days, six days, one week, or more than one week following administration. In a preferred embodiment, the interval between treatment is 24 h and maximum treatment duration is D4 to day 14 (10 days).

Dosage regimens or cycles of the agents can be completely or partially overlapping, or can be sequential. For example, in some embodiments, all such administration(s) of the mTOR inhibitor and/or P-gp inhibitor occur before or after administration of the Src/c-Abl pathway inhibitor. Alternatively, administration of one or more doses of the mTOR inhibitor and/or P-gp inhibitor can be temporally staggered with the administration of Src/c-Abl pathway inhibitor to form a uniform or non-uniform course of treatment whereby one or more doses of mTOR inhibitor and/or P-gp inhibitor are administered, followed by one or more doses of Src/c-Abl pathway inhibitor, followed by one or more doses of mTOR inhibitor and/or P-gp inhibitor; or one or more doses of Src/c-Abl pathway inhibitor are administered, followed by one or more doses of mTOR inhibitor and/or P-gp inhibitor, followed by one or more doses of Src/c-Abl pathway inhibitor; etc., all according to whatever schedule is selected or desired by the researcher or clinician administering the therapy.

An effective amount of each of the agents can be administered as a single unit dosage (e.g., as dosage unit), or sub-therapeutic doses that are administered over a finite time interval. Such unit doses may be administered on a daily basis for a finite time period, such as up to 3 days, or up to 5 days, or up to 7 days, or up to 10 days, or up to 15 days or up to 20 days or up to 25 days, are all specifically contemplated.

C. Formulations

The compositions are most typically administered systemically.

Pharmaceutical compositions can be for administration by parenteral (intramuscular, intraperitoneal, intravenous (IV) or subcutaneous injection), enteral, or transmucosal (nasal, pulmonary, vaginal, rectal, or sublingual) routes of administration or using bioerodible inserts and can be formulated in dosage forms appropriate for each route of administration.

Drugs can be formulated for immediate release, extended release, or modified release. A delayed release dosage form is one that releases a drug (or drugs) at a time other than promptly after administration. An extended release dosage form is one that allows at least a twofold reduction in dosing frequency as compared to that drug presented as a conventional dosage form (e.g. as a solution or prompt drug-releasing, conventional solid dosage form). A modified release dosage form is one for which the drug release characteristics of time course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

Transdermal formulations may also be prepared. These will typically be gels, ointments, lotions, sprays, patches or microneedle devices. Transdermal formulations can include penetration enhancers.

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, desintegrators, fillers, and coating compositions.

The compound can be administered to a subject with or without the aid of a delivery vehicle. Appropriate delivery vehicles for the compounds are known in the art and can be selected to suit the particular active agent. For example, in some embodiments, the active agent(s) is incorporated into or encapsulated by a nanoparticle, microparticle, micelle, synthetic lipoprotein particle, or carbon nanotube. For example, the compositions can be incorporated into a vehicle such as polymeric microparticles which provide controlled release of the active agent(s). In some embodiments, release of the drug(s) is controlled by diffusion of the active agent(s) out of the microparticles and/or degradation of the polymeric particles by hydrolysis and/or enzymatic degradation.

EXAMPLES

The present invention will be further understood by reference to the following non-limiting examples.

An objective of the experiments below was to create a robust ALS motor unit in a microfluidic device for drug screening. Coculture with motor neuron (MN) spheroids from ESC and ALS patient-derived iPSC and 3D skeletal muscle tissues demonstrated the formation of neuromuscular junctions (NMJs) and can provide quantitative data (muscle contraction force) by automated image analysis using Python to test neural activity indirectly via muscle contraction for drug screening. The use of human iPSC-derived NSCs from a patient with ALS was approved by the respective departments at Massachusetts Institute of Technology. All methods with human primate materials, cells, hESCs and iPSCs, and toxin were performed in accordance with National Academy of Sciences Guidelines for Human Embryonic Stem Cell Research with the Massachusetts Institute of Technology Committee on Assessment of Biohazards and Embryonic Stem Cell Research Oversight.

Statistical Analysis

The reported values correspond to the means of a minimum of three independent experiments. Data are presented as means±SD. Comparisons were performed using one-way ANOVA with post hoc pairwise comparisons using the Tukey-Kramer method. P values $<0.05$ and $<0.01$ were taken to represent statistically significant results and highly statistically significant results, respectively. The tests were performed using JMP Pro software (SAS Institute, Cary, NC, USA).

Example 1: Muscle Performance and Characterization of MN Spheroids in Microfluidic Devices Materials and Methods Microfluidic Device Fabrication The mold fabrication process was similar to that previously reported (Uzel et al., *Sci. Adv.* 2, e1501429 (2016)). Briefly, device structures were designed using Solidworks (Dassault Systemes SolidWorks Corporation), and the patterns were transferred onto a transparency mask using high-resolution printing (FineLine Imaging). Silicon wafers were then fabricated by photolithography using typical SU-8 photoresist techniques. All the mold surfaces were treated with (tridecafluoro-1,1,2,2-tetrahydrooctyl)-1-trichlorosilane for at least 2 hours. For the main microfluidic section, PDMS and curing reagents (Ellsworth Adhesives) were mixed in a 10:1 ratio, poured into the SU-8 mold, and cured at 80° C. for at least 6 hours. The pillar head was then attached to the base of the pillar. The pillar head consisted of 250 µm by 250 µm squares of 25-µm-thin PDMS (obtained by spin coating onto a 10-cm petri dish lid for 30 s at 5000 rpm). The pillar heads were manually positioned over the pillar and glued with uncured PDMS. Using this PDMS mold, a negative mold was fabricated using Smooth-Cast 300, and PDMS was then poured into the mold and cured for 6 hours. Devices were then cut off the mold and trimmed to the appropriate size, and gel filling ports, a vacuum port, and medium ports/reservoirs were formed with 1-, 2-, and 6-mm-diameter biopsy punches, respectively. The devices were then sterilized by wet autoclaving, followed by dry autoclaving. After drying completely, no. 1 glass was bonded using oxygen plasma.

Motor Neurons hESC (H9, WA09)-derived NSCs (Gibco) and ALS-iPSC-derived NSCs (from the peripheral blood of a 55-year-old Caucasian woman with sporadic ALS, iXCells Biotechnologies) were maintained on Geltrex LDEV-Free Reduced Growth Factor Basement Membrane Matrix (Thermo Fisher Scientific) in StemPro NSC SFM medium supplemented with 2 mM GlutaMAX-I supplement (Gibco), human recombinant bFGF (20 ng/ml), epidermal growth factor (20 ng/ml), and 2% StemPro neural supplement. Neuro spheroids were formed using a spindle-shaped bottom 96-well plate (PrimeSurface 96M) for 24 hours by seeding the hESC-derived NSCs and ALS-iPSC-derived NSCs at a density of $1.0 \times 10^4$ cells per well. The differentiation protocol was previously described in the literature (Jha et al., Stem Cell Rev. 11, 194-204 (2015)). Briefly, after 24 hours of seeding, the culture medium was replaced with 100 µl per well of StemPro hESC medium supplemented with RA (50 µM), sonic hedgehog (200 ng/ml), bFGF (8 ng/ml), and activin A (10 ng/ml) for cell fate determination via caudalization and ventralization (MN differentiation medium). Then, culture medium was changed to 100 µl per well of MN differentiation medium excluding activin A. After culturing for 20 days, the culture medium was replaced again using 100 µl per well of StemPro hESC medium supplemented with RA (50 µM), BDNF (10 ng/ml), and GDNF (10 ng/ml) for maturation of MNs and cultured for 7 to 8 more days (MN medium). To remove the neural progenitor cells and NSCs from the spheroids, CultureOne Supplement (Thermo Fisher Scientific) was treated before 24 hours of injection into the devices. The culture medium was then switched to MN medium without RA for an additional 14 days in the left medium reservoir of the microfluidic devices. Karyotype, donor, and reprogramming information of iPSCs used in this study is available at the hPSCreg website: parental iPSCs of iCell skeletal myoblast and iCell ECs=hPSCreg Name: CDIi001-A (Alternative Name: 01279); parental ES cells of NSC=hPSCreg Name: WAe009-A (Alternative Names: WA09, H9), and parental iPSCs of ALS-NSCs=iXCells Biotechnologies Catalog Number 30HU-004. G-band karyotyping analysis of parental ALS-iPSCs was performed by Cell Line Genetics. ALS iPS-derived MNs are heterozygous for G298S and homozygous for M337V and Q343R, whereas ES-derived MN has no mutation related to these three SNP mutations. No SOD1 mutation of A4V and G93A in either type of MN cells.

Ipsc-Derived Skeletal Muscle Cells

Human iPSC-derived skeletal myoblasts (iCell Skeletal Myoblasts, Cellular Dynamics Technology) were maintained on fibronectin coating (10 µg/ml) in minimum essential medium-α (MEM-α) supplemented with 8-bromo-cyclic AMP (1 mM), CHIR99021 (2 µM), dorsomorphin (1 µM), and 5% knockout serum replacement (SkMM). For differentiation into mature myocytes in the microfluidic devices, 24 hours after cell seeding with SkMM, 200 µl of culture medium was injected into the right medium reservoir with Dulbecco's modified Eagle's medium (DMEM) supplemented with 2% horse serum, human recombinant IGF-1 (50 ng/ml), and 1% penicillin/streptomycin (SkDM). After several days, the injected culture medium invaded the left medium reservoir owing to the formation of muscle fiber bundle and capillary action. Then, SkDM was also injected to both the right and left medium reservoir (200 µl of each) up to 14 days of culture.

Mouse Myoblasts

Mouse C2C12 myoblasts (American Type Culture Collection) were cultured to <70% confluency in growth medium consisting of DMEM with 10% fetal bovine serum (Invitrogen) and 1% penicillin/streptomycin. None of the cells were used beyond a passage number of 20. All cells were kept in incubators at 37° C. and 5% CO2.

Electrical and Chemical Stimulation

Electrical stimulation was delivered via platinum electrodes positioned 3 mm away from each other across the neuromuscular tissue. They were controlled by an Arduino circuit delivering 12-V square inputs. To activate the MNs, they were stimulated by adding glutamic acid (0.1 mM) to the culture medium. For the excitotoxicity experiment, excess glutamic acid (5 mM) was added to the culture medium for 7 days. Before the measurement of the muscle contraction force, this high concentration of glutamic acid was rinsed away with phosphate-buffered saline (PBS) and then replaced with a low concentration of glutamic acid (0.1 mM). For simulation of a neurotoxin added to a human NMJ model, TTX (final concentration, 1 µM) was added to the culture medium and the muscle contraction force was measured. Then, the TTX was rinsed away with PBS and replaced with a low concentration of glutamic acid (0.1 mM).

Image Acquisition and Analysis

Epifluorescence and confocal images were acquired using a Zeiss Axiovert 200 microscope and an Olympus FV-1000 confocal microscope, respectively. 3D reconstruction and analysis of confocal images were performed with IMARIS software (Bitplane). Muscle contraction measurement was performed in a stage-top incubator (INUBG2TF-WSKM-SET, Tokai Hit) on Axiovert 200, and image sequences were captured using AxioVision. Automated tracking of the local deformation of the skeletal muscle cells and deflection of the pillars upon light excitation were carried out using ImageJ and Python script with an OpenCV package. Formulas for calculating muscle contraction force from pillar displacements include:

$$\text{Displacement of pillar edge } (\delta) = \frac{|S_1' - S_1|/L + |S_2' - S_2|/L}{2}$$

$$I : \text{Second moment of area} = \frac{\pi a b^3}{4}$$

$$\therefore a = 1.2 \times 10^{-4} m$$

$$b = 7.0 \times 10^{-5} m$$

Figure 1C:
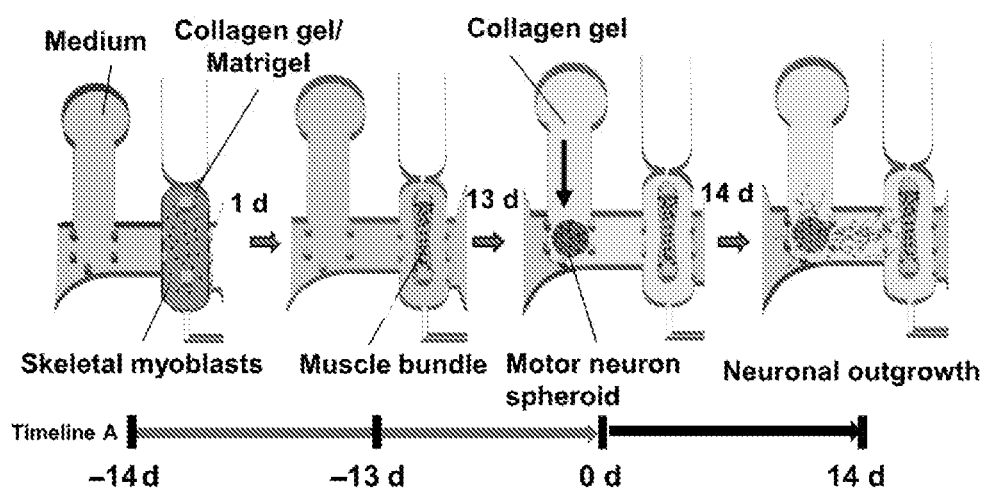
FIG. 1C is a cartoon illustration showing timeline of human motor unit developments in the microfluidic device. iPS-derived skeletal myoblasts were injected into the right compartment with the collagen/MATRIGEL® mixture from gel injection port 1. Within 1 day, a skeletal muscle fiber bundle was formed on pillar structures. After 13 days of differentiation, an MN spheroid with collagen gel was injected into the left compartment from gel injection port 2. Neural outgrowth occurs by 14 days, resulting in the formation of a human motor unit along with NMJ.
Figures 1D, 1E, 1F:
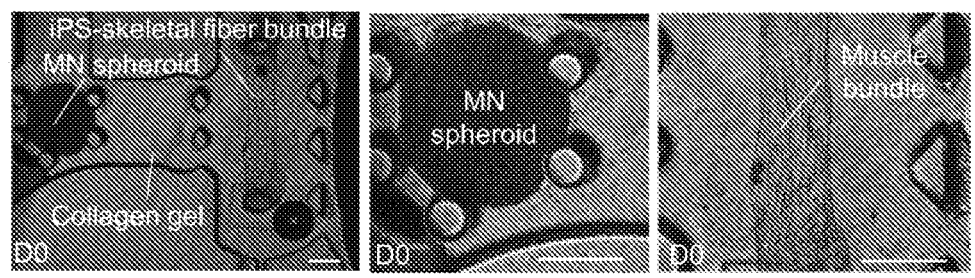
FIGS. 1D-1F are images of an MN spheroid (1D, 1E) and a skeletal muscle fiber bundle (1D, 1F) in a microfluidic chip on day 0 (D0). A differentiated MN spheroid and a muscle fiber bundle were embedded in collagen gel. Scale bars, 200 μm.
Figure 1G:
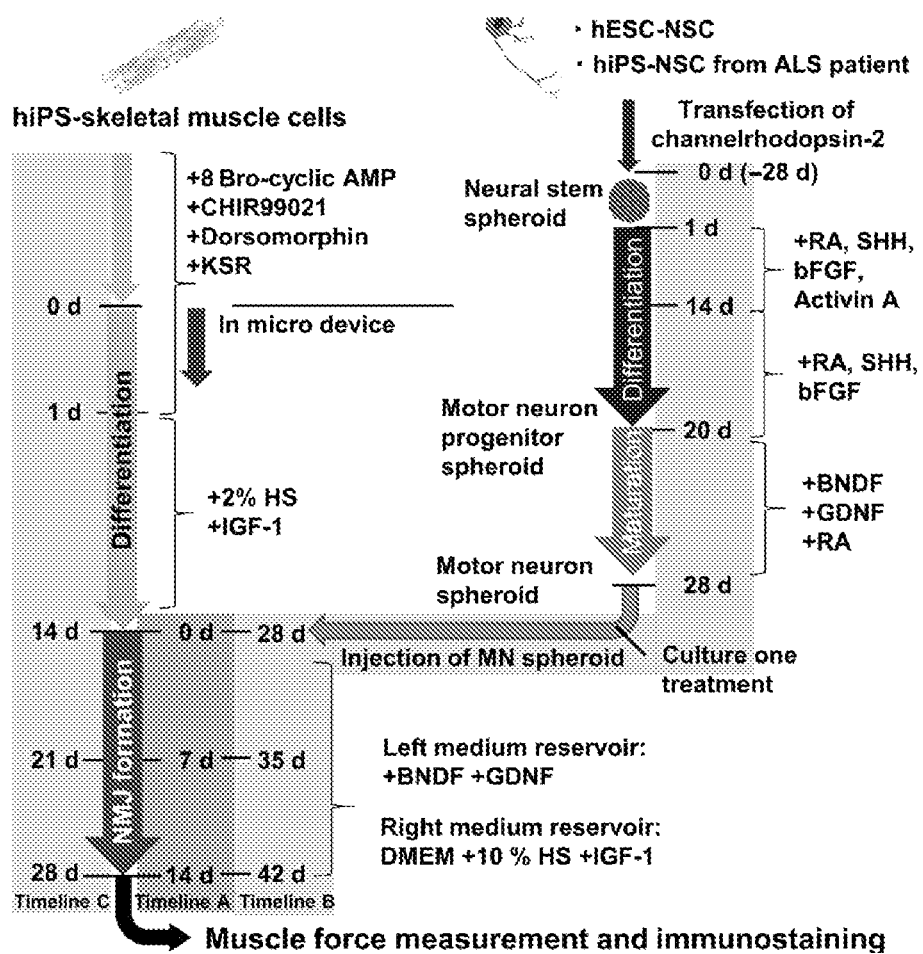
FIG. 1G is a flow diagram showing preparation and differentiation of skeletal muscle cell and MN cells. hESC-derived NSC spheroids were formed and differentiated into mature MNs by treatment with appropriate growth factors. Meanwhile, hiPS-derived skeletal muscle fiber bundles were formed in the microfluidic device and differentiated into mature myotubes. Then, an MN spheroid was injected for coculture of the two tissues. Timeline A indicates 0 d=initial day of coculture; timeline B indicates 0 d=initial day of generating neurospheorid; and timeline C indicates 0 d=initial day of seeding skeletal muscle cells into the device. KSR, knockout serum replacement; IGF-1, insulin-like growth factor 1; SHH, sonic hedgehog; bFGF, basic fibroblast growth factor; BDNF, brain-derived neurotrophic factor; GDNF, glial cell-derived neurotrophic factor.
Figure 1H:
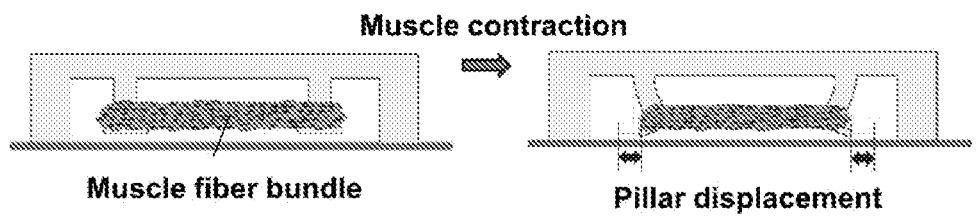
FIG. 1H is a cartoon illustrating how muscle contraction force driven by electrical stimulation and chemical stimulation via MN is estimated by pillar displacement.
Figure 1I:
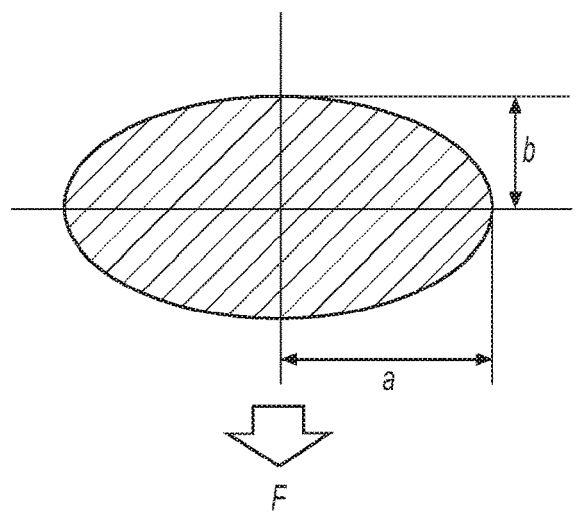
FIG. 1I is a diagram of the a pillar cross section illustrating variables used in estimating muscle contraction through automated detection of pillar displacement.

(See also FIG. 1I);

$$\delta = \frac{FL^3}{3EI} \therefore L = 3 \times 10^{-4} m$$

$$E = 1.84 Mpa$$

Muscle contraction force $$F = \frac{3EI \cdot \delta}{L^3}$$

Figure 1J:
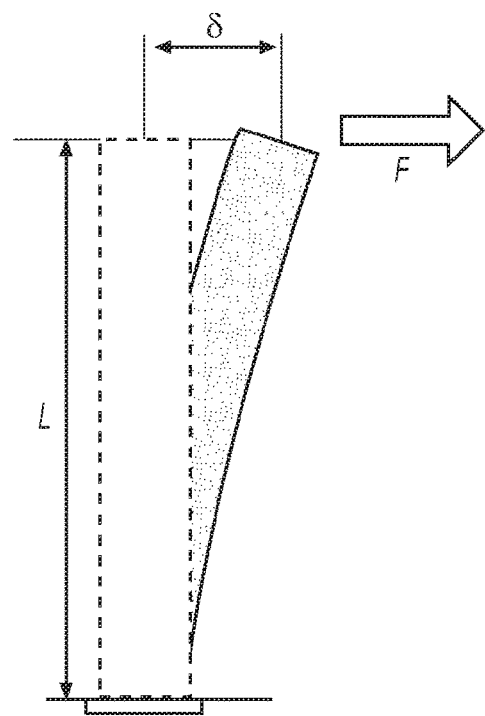
FIG. 1J is a diagram of a pillar profile illustrating variables used in estimating muscle contraction through automated detection of pillar displacement.

(See also FIG. 1J).

The presence of gel did not affect the calculation of muscle contraction force as shown by Uzel et al., Sci. Adv. 2, e1501429 (2016). Image analysis regarding the muscle width and axon outgrowth was conducted using ImageJ. Fusion index for skeletal muscle cells is defined as the number of myogenin-expressing myotubes with greater than two nuclei divided by the total number of nuclei. To quantify nAChR clusters, quantitative fluorescence imaging was performed using an open-source software package in CellProfiler (Broad Institute). The automated image cytometry system identifies and measures objects' size, shape, pixel intensity, and topology, and the resulting data are corrected using a background-subtraction algorithm. nAChR clusters in CellProfiler were defined using agrin-treated myotubes [Alexa 488-conjugated anti-agrin antibody (ab85174), Abcam]. Before the measurement, skeletal myotubes were prestained by Alexa 488-conjugated anti-agrin antibody in culture medium (1:100) for 1 hour at 37° C. in the device. Agrin, normally secreted by MNs, stabilizes and aggregates nAChRs into distinguishable cluster regions (>65% intensity), whereas outside these regions, nAChRs largely exist in dispersed microclusters (<65% intensity) denoted by lower-intensity pixels. In this manner, nAChR area was calculated for individual muscle fiber bundles. It is understood that other methods of monitoring could be used.

Western Blotting

For immunoblotting, cells were lysed in Cell Lysis Buffer (Cell Signaling Technology), and 10 µg of protein was subjected to SDS-polyacrylamide gel electrophoresis [using 4 to 12% (w/v) gradient gels (Life Technologies, NuPAGE Novex, Bis-Tris)], transferred to nitrocellulose membranes, and assayed by immunoblotting. The primary antibodies were mouse anti-actin (Thermo Fisher Scientific, β-actin loading control, 1:5000) and mouse anti-myosin heavy chain (R&D Systems, 1:2000). The secondary antibody was horseradish peroxidase (HRP)-conjugated anti-mouse IgG antibody (Cell Signaling Technology, Danvers, MA, USA). An HRP substrate was used for chemiluminescent analysis (Bio-Rad, Hercules, CA, USA).

Results

Figures 2A, 2B, 2C:
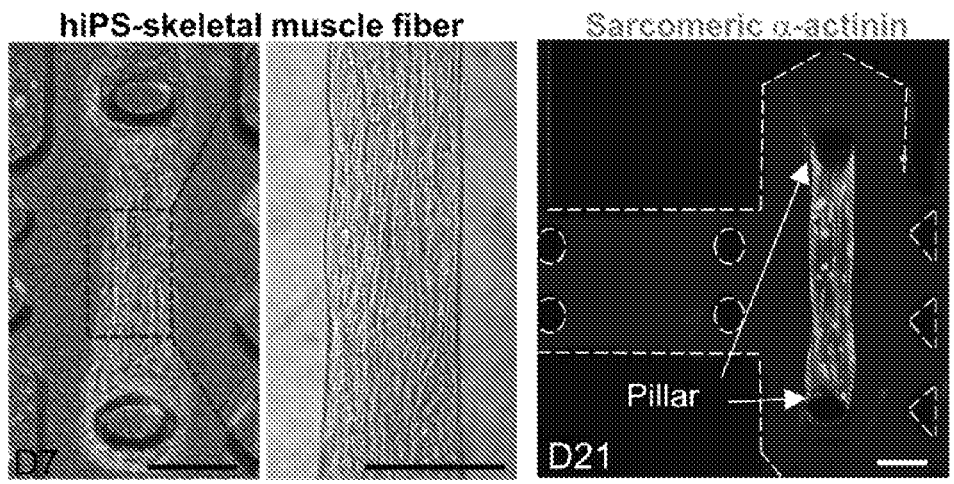
FIGS. 2A-2C are images illustrating a fabricated skeletal muscle fiber bundle approximately 1500 μm in length attaching the pillars at D7 and D21. Scale bars, 200 μm.
Figure 2D:
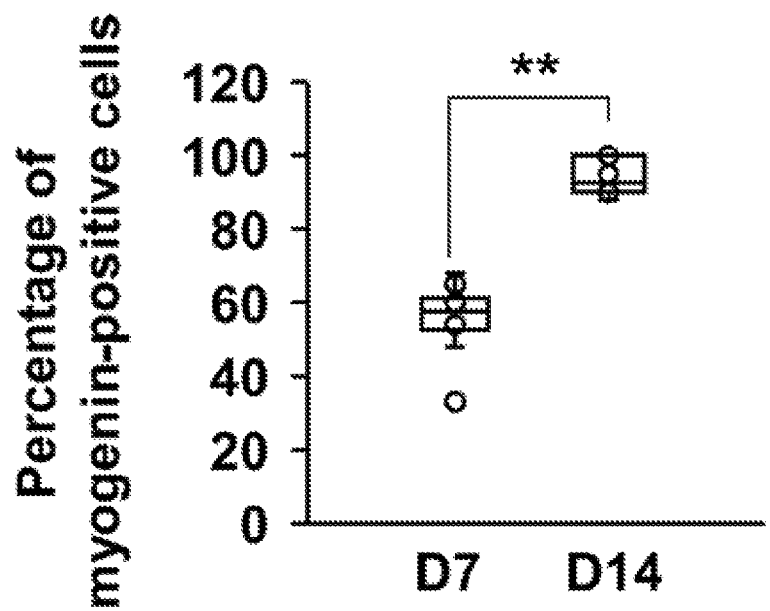
FIG. 2D is a dot plot showing the population of myogenin-positive cells on muscle fiber bundle. n=5.
Figure 2E:
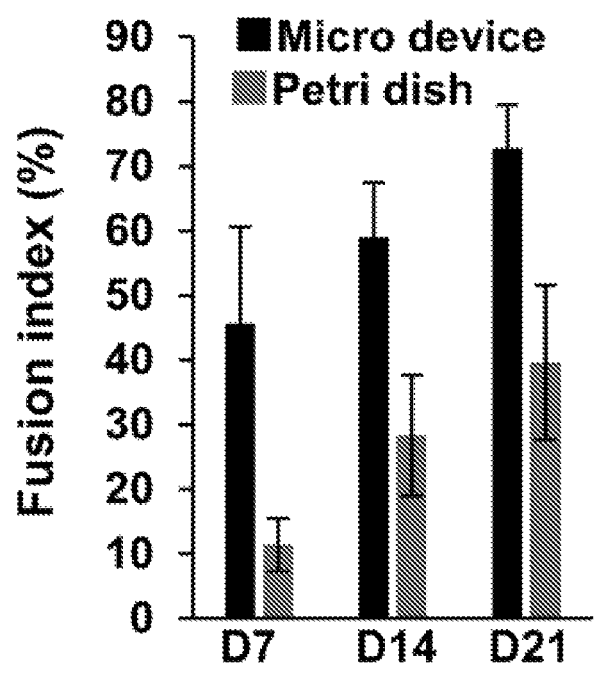
FIG. 2E is a bar graphs showing the fusion index for skeletal muscle cells in a 3D micro device and a 2D monolayer (petri dish). n=8.
Figure 2F:
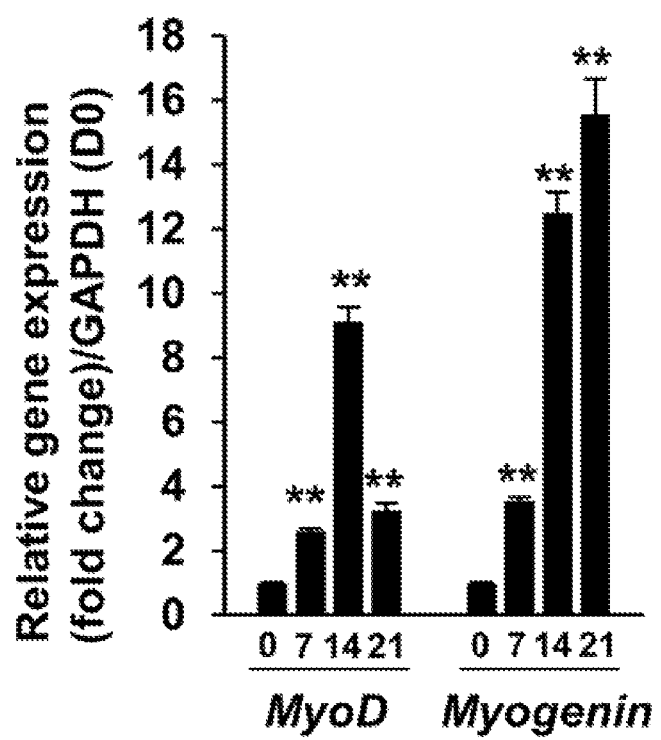
FIGS. 2F-2G are bar graphs showing gene expression change of MyoD and myogenin, (2F) and GAPDH (2G) at D7, D14, and D21 against D0 or D7. n=5. GAPDH, glyceraldehyde 3-phosphate dehydrogenase. N.D., not determined.
Figure 2G:
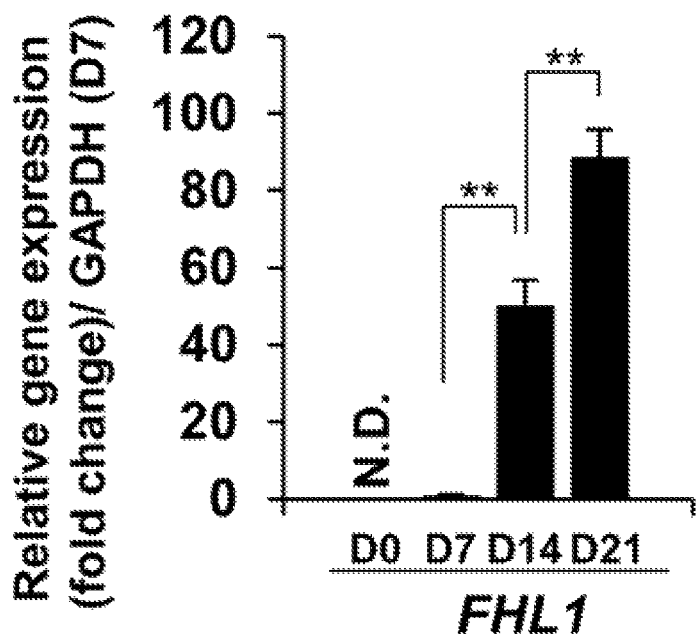

A 3D muscle fiber bundle was fabricated in a microfluidic device (FIGS. 1A and 1B) by injecting iPSC-derived skeletal myoblasts into one compartment of the device with a collagen/Matrigel mixture (FIG. 1C). The cells spontaneously formed muscle fiber bundles around the pillar structures (FIGS. 1D-1F and 2A-2C) that were close to the glass bottom, but not attached (FIG. 1H). Pillar structures help free muscle movement and improve image quality, and muscle contraction forces can be measured by the pillar movement. By day 14, most cells expressed myogenin, which is a muscle-specific basic-helix-loop-helix transcription factor and a mature myocyte marker (FIG. 2D). The fusion index showed that differentiation in the 3D condition in the microfluidic device accelerated compared with a 2D monolayer culture (FIG. 2E). After around day 21, the skeletal muscle exhibited regular well-patterned sarcomeric structures along with mature myotube differentiation. Differentiation into a mature myotube was characterized in a petri dish by immunostaining of MyoD and myogenin. After D7 of differentiation, skeletal myoblasts partially expressed myogenin which is mature myocyte marker although almost all myoblasts expressed MyoD. After D14 of differentiation, myogenin expression can be seen in almost all myoblasts. Furthermore, the mRNA expression levels of myogenin and four and a half LIM domain protein 1 (FHL1), also increased by day 21, but MyoD mRNA decreased, indicating that the 3D muscle fiber bundles became mature muscle strips by day 21 (FIGS. 2F and 2G).

Figure 2H:
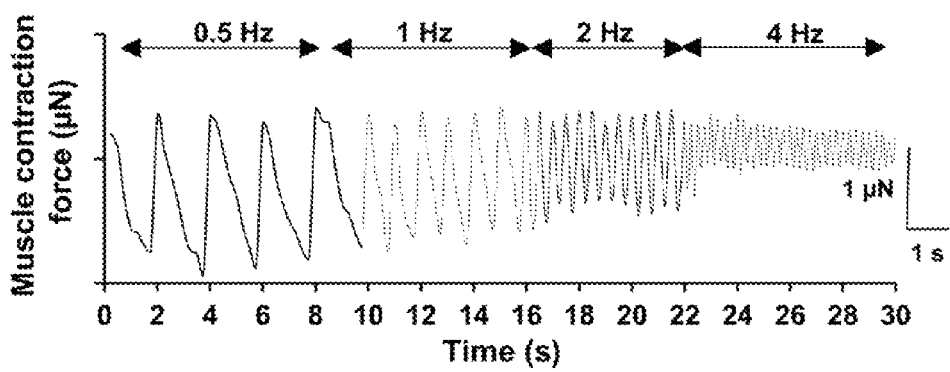
FIG. 2H is a plot showing muscle contraction powered by electrical stimulation at different frequencies (0.5 to 4 Hz).

To test the functionality of the 3D muscle fiber bundle, muscle contractile force was measured after electrical stimulation at different frequencies (0.5, 1, 2, and 4 Hz) (FIG. 2H). Active muscle contraction was readily observed, with a maximum muscle force at 0.5 Hz of approximately 2 µN (0.25 mN/mm2). Muscle formation and contraction (based on iPSC-derived skeletal muscle cells) were compared to those results from mouse myoblast C2C12 cells, which are often used for the in vitro study of muscle fibers (Uzel et al., Sci. Adv. 2, e1501429 (2016), Raman et al., Proc. Natd. Acad. Sci. U.S.A. 113, 3497-3502 (2016)). The C2C12 cells also formed thin 3D muscle fiber bundles, attaching to the pillar structures by day 14. However, after 28 days of culture, the C2C12 muscle structures collapsed and detached from the pillar structures. In contrast, the muscle fiber based on the iPSC-derived skeletal muscle cells maintained their structure and remained attached. In addition, the muscle force generated by contraction of electrically stimulated iPSC-derived muscle fiber bundles was higher than that associated with the C2C12 cells.

Figure 2I:
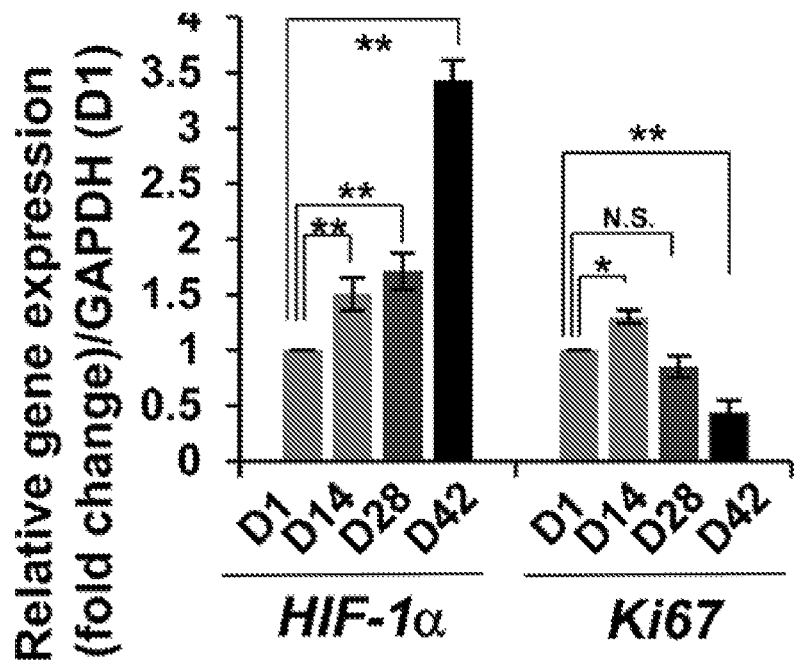
FIG. 2I is a bar graph showing necrotic cell death and cell cycle determined by HIF-1α expression and Ki67. N.S., not significant.

Meanwhile, MN spheroids were generated to accelerate MN differentiation from human embryonic stem cell (hESC)-derived neural stem cells (NSCs). The formation of NSC spheroids and the differentiation protocol have been described by Osaki et al., Sci. Rep. 8, 5168 (2018) (FIG. 1G). After 14 days of differentiation, the HB9 gene (a typical MN marker) was expressed in the MN spheroids and increased by day 28. A heat map of mRNA expression showed that Nestin, E-cadherin, SOX1, and PAX6 (an NSC marker) decreased, while OLIG2, neurogenin2 (NGN2), NeuroDl (an MN progenitor marker), HB9, islet1, ChAT (an MN marker), neurofilament heavy chain (SMI-32), Synapsin I, and vesicular acetylcholine transporter (VAChT) (a mature MN marker) increased over time up to day 42. In addition, glial fibrillary acidic protein (GFAP, a glial cell marker) also slightly increased, whereas oligodendrocyte-specific protein (OSP) and SOX10 (an oligodendrocyte marker) did not change significantly. HIF-1α (a hypoxia marker) slightly increased and Ki67 (a cell cycle marker) decreased by day 42 (FIG. 2I). These results indicate that MN spheroid culturing induced hypoxia to some extent, especially in the core because the diameter of MN spheroids is >400 µm, in excess of the diffusion distance of oxygen (Groebe et al., Biol. Phys. 34, 395-401 (1996)). However, the outer layer of the spheroids remains healthy and can differentiate into mature MNs. In support of this, when NSC-MN spheroids were reseeded to a laminin-coated dish, well-connected neuronal networks can be established on days 25 and 45.

Example 2: Fabrication of a 3D Motor Unit Model and NMJs in Microfluidic Devices Materials and Methods
Formation of 3D Motor Units To avoid single-cell attachment to the glass bottom, the microfluidic device was incubated with 4% Pluronic F-127 (Sigma) in the incubator for 1 hour, rinsed with distilled water, and dried. Human iPSC-skeletal muscle cells were injected into the right compartment of the microfluidic device with a mixture of porcine skin type I collagen gel (Nitta Gelatin, 2.4 mg/ml) and 10% MATRIGEL® (BD Biosciences) via gel injection port no. 1 (FIGS. 1A and 1B). A 3D muscle fiber bundle was formed within 24 hours, with both sides of the muscle attached to the pillar structures. The muscle fiber bundle was then cultured and differentiated using 2% horse serum and IGF-1. After 13 days of differentiation, predifferentiated MN spheroids (normal and ALS) were injected into the left compartment (FIG. 1B) via gel injection port no. 2 with collagen without MATRIGEL®. For the cocultured MN spheroids and skeletal muscle fiber bundles in microfluidic devices, StemPro hESC medium supplemented with RA (50 µM), BDNF (10 ng/ml), and GDNF (10 ng/ml) was poured into the left medium reservoir (close to the MN spheroids), and DMEM, 10% horse serum, human recombinant IGF-1 (50 ng/ml), and 1% penicillin/streptomycin were poured into the right medium reservoir (close to the skeletal muscle fiber bundles). Two types of culture medium maintained segregating at least for 6 hours. To study the effects of drug application, bosutinib (100 µM)

and rapamycin (200 nM) were applied to recover the ALS-derived motor unit muscle contraction force at day 4 with MN medium, and then muscle contraction was tested at day 7. The muscle apoptosis assay, PCR, and immunostaining of TDP-43 were performed at day 14.

Immunocytochemistry

Cells were fixed with 4% paraformaldehyde (PFA) for 20 min and then permeabilized with 0.2% Triton X-100 for 5 min. After blocking with 1% bovine serum albumin (BSA) for 2 hours, the cells were incubated for 2 hours at room temperature with a primary antibody. A secondary antibody was then administered for 2 hours at room temperature. The primary antibodies were mouse anti-neuron-specific βIII tubulin (Tuj1, 1:100), mouse anti-human ChAT (1:200), rabbit anti-human islet1 (1:100), rat anti-human α-actinin (1:500), rat anti-human GFAP (1:200), rabbit anti-human P-gp (1:500), mouse anti-human ZO-1, and mouse anti-human occludin (1:500). The secondary antibodies were Alexa Fluor 555 anti-rabbit immunoglobulin G (IgG) (H+L) (1:500), Alexa Fluor 405 anti-rabbit IgG (H+L) (1:500), Alexa Fluor 488 goat anti-mouse IgG (H+L) (1:500), Alexa Fluor 488 goat anti-rabbit IgG (H+L) (1:500), and Alexa Fluor 647 goat anti-rat IgG (H+L). F-actin was stained with Alexa Fluor 488 or 647 phalloidin (Cytoskeleton Inc., Denver, CO, USA) and DAPI for 20 min at room temperature, followed by three rinses with Dulbecco's phosphate-buffered saline with Ca2+ and Mg2+(DPBS++). To stain the nAChR clusters, the neuromuscular motor units were incubated with aBTX-conjugated Alexa Fluor 647 (2 mg/ml, Molecular Probes) for 1 hour at 37° C. in a 5% CO2 incubator. The constructs were then rinsed with PBS, fixed for 1 hour with 4% PFA in PBS, permeabilized with 0.1% Triton X-100 in PBS for 15 min, and blocked with 2% BSA in PBS overnight. To detect cells in an apoptosis stage (caspase activity) in the muscle fiber bundles, they were incubated with CellEvent Caspase-3/7 Green Detection Reagent (Thermo Fisher Scientific, Waltham, MA, USA) for 30 min. All cells and samples were observed using a phase-contrast microscope (Axiovert 200, Zeiss, Germany) and a confocal laser scanning microscope (FV-1000, Olympus, Japan).

Measurement of MN Activity with Ca2+ Oscillation Imaging

To capture neural activity and synapse formation, both types of cells in the microfluidic devices were rinsed three times with PBS (without Ca2+ and Mg2+), recording medium [20 mM 4-(2-hydroxyethyl)-1-piperazineethanesulfonic acid (Hepes), 115 mM NaCl, 5.4 mM KCl, 0.8 mM MgCl$_2$, 1.8 mM CaCl2), and 13.8 mM glucose] was added with Fluo-8 AM (5 μM, 488 nm), and the mixture was incubated for 1 hour at 37° C. After loading Fluo-8 AM, the loading medium was replaced with the recording medium. Time-lapse movies were acquired for 10 min (resolution, 680×512 pixels; exposure time, 10 ms) using a fluorescent microscope (Axiovert 200, Zeiss).

Real-Time Reverse Transcription PCR

To measure the biological activity of the MN spheroids and muscle differentiation, total RNA was isolated from tissues with TRIzol reagent (Life Science, Waltham, MA, USA). Reverse transcription (RT) was performed using a SuperScript VILO cDNA Synthesis Kit (Invitrogen, Waltham, MA, USA). RT-PCR was performed with a 7900HT Fast Real-Time PCR System (Applied Biosystems, Waltham, MA, USA) using SYBR Premix Ex Taq (Takara, Kusatsu, Japan). The mRNA level of GAPDH (a housekeeping gene) was set to 100% and used as the internal standard in all experiments. The RT-PCR experiment was repeated at least three times for cDNA prepared from at least three batches.

Results

After formation of the 3D muscle fiber and differentiation to produce a mature myotube, predifferentiated MN spheroids were injected into the left compartment of the microfluidic devices with collagen gel (FIGS. 1B and 1D-1F). For coculturing of the two types of tissues (MN spheroids and muscle fibers), MN maintenance medium was kept in the left medium reservoir (close to the MN spheroids) and skeletal myocyte differentiation medium (SkDM) was kept in the right medium reservoir (close to the muscle fibers).

Figure 3A:
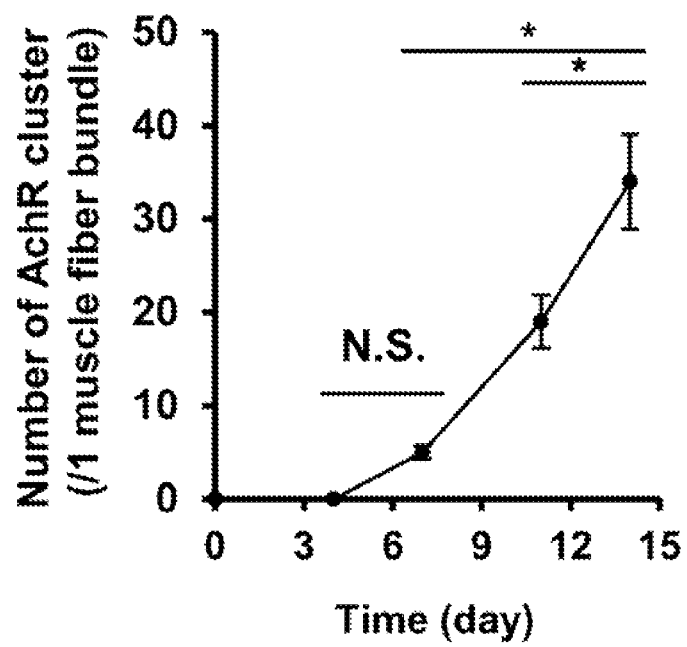
FIG. 3A is a line graph of the number of clusters of nAChRs on single muscle fiber bundles increased over time. n=4.
Figure 3B:
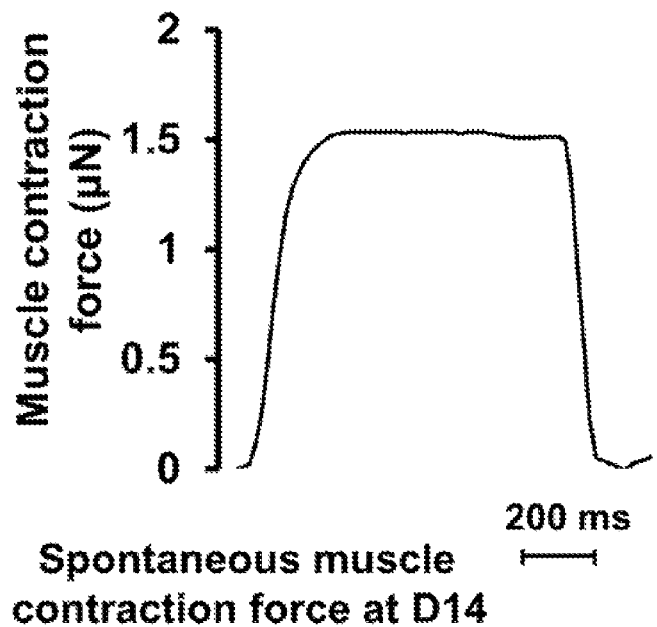
FIG. 3B is a plot illustrating muscle contraction force estimation by pillar displacement on D14 of coculture.
Figure 3C:
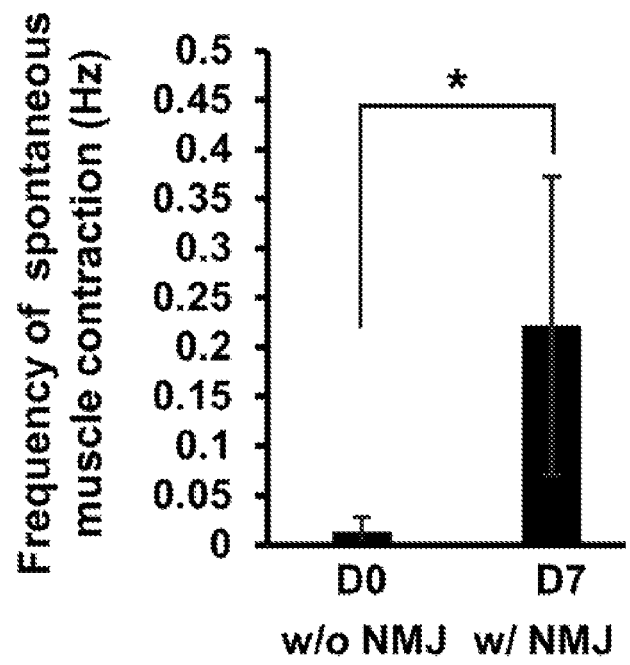
FIGS. 3C-3D are bar graphs showing the frequency of spontaneous muscle contraction and spontaneous muscle contraction force on D0 (before NMJ formation, without NMJ) (3C) and D7 (after NMJ formation, with NMJ) (3D) without glutamic acid stimulation. n=6.
Figure 3D:
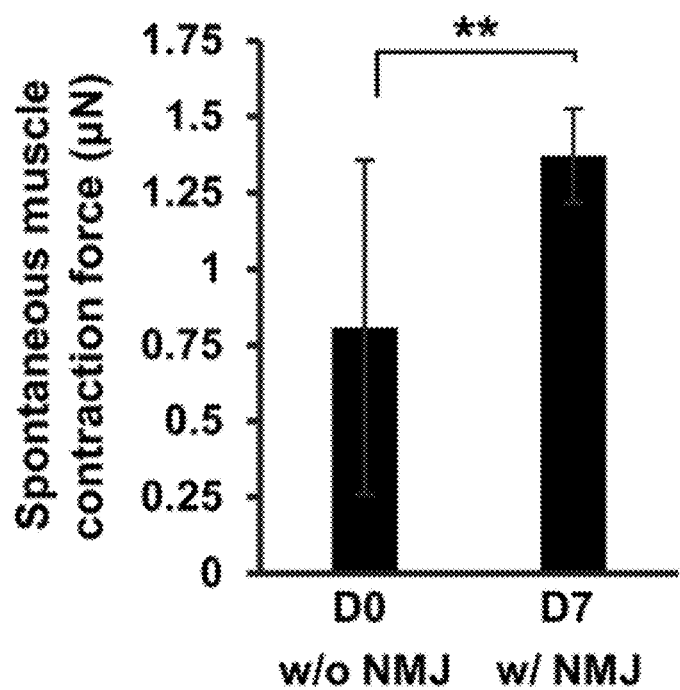

Motor neurite elongation in collagen gel (toward the muscle fiber bundle) was observed by day 4. By day 7, many neurites had reached the 3D muscle fiber bundle. Thick neural fiber bundles were observed close to the muscle fiber bundle by 14 days in culture. Immunostaining of choline acetyltransferase (ChAT), islet1, and α-actinin indicated the maturation of the elongated MNs and mature 3D muscle fibers in the coculture condition. Cells expressing GFAP (astrocytes) were identified, consistent with the polymerase chain reaction (PCR) results, confocal imaging revealed neurite terminal attachment and NMJ formation by day 4. Thick MN fibers reached close to the muscle bundle and thin neurites then spread out and attached to various myotubes by day 14. Immunostaining of nicotinic acetylcholine receptors (nAChRs) indicated NMJ formation where the muscle fiber and neurite terminals overlapped, as early as day 7, and the number of nAChR clusters increased through day 14 (FIG. 3A). Before formation of the NMJ (day 0), spontaneous muscle contraction occurs infrequently (less than 0.05 Hz) with high variation. After NMJ formation (day 7), the frequency of spontaneous muscle contraction increased (0.1 to 0.3 Hz) (FIG. 3C). Muscle contraction force slightly increased compared with that before formation of the NMJ (day 0, FIG. 3D).

Figure 3E:
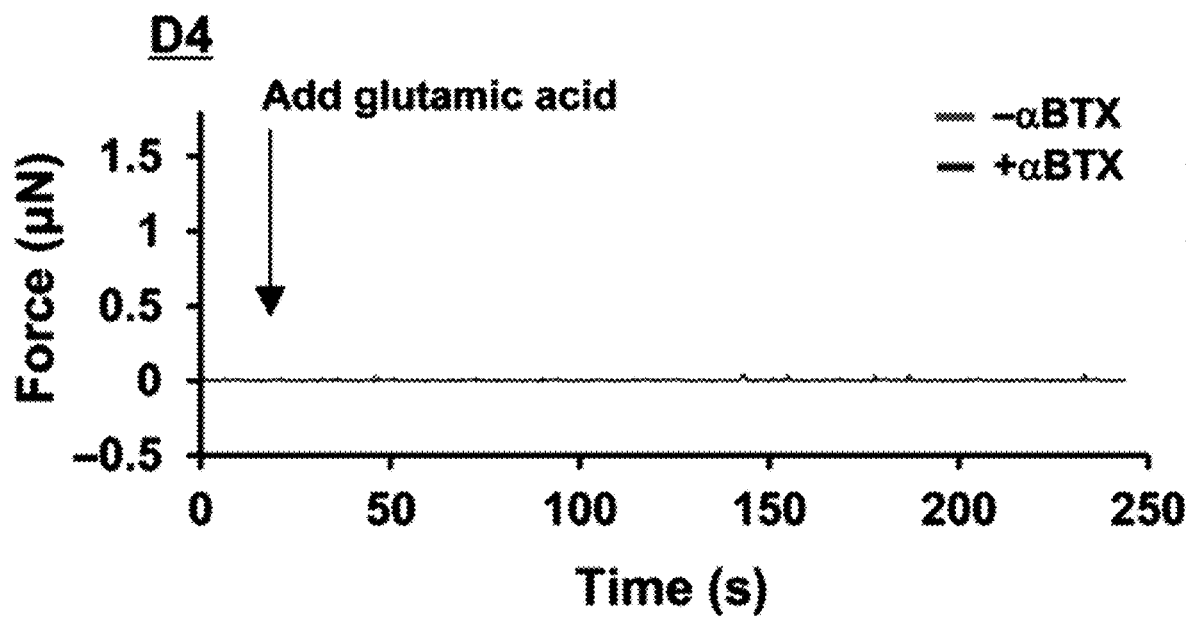
FIG. 3E-3G are plots showing the measurement of muscle contraction force by adding glutamic acid on D4, D7, and D14. **$P<0.05$; *$P<0.01$, Student's t test and one-way ANOVA. Error bars±SD.
Figure 3F:
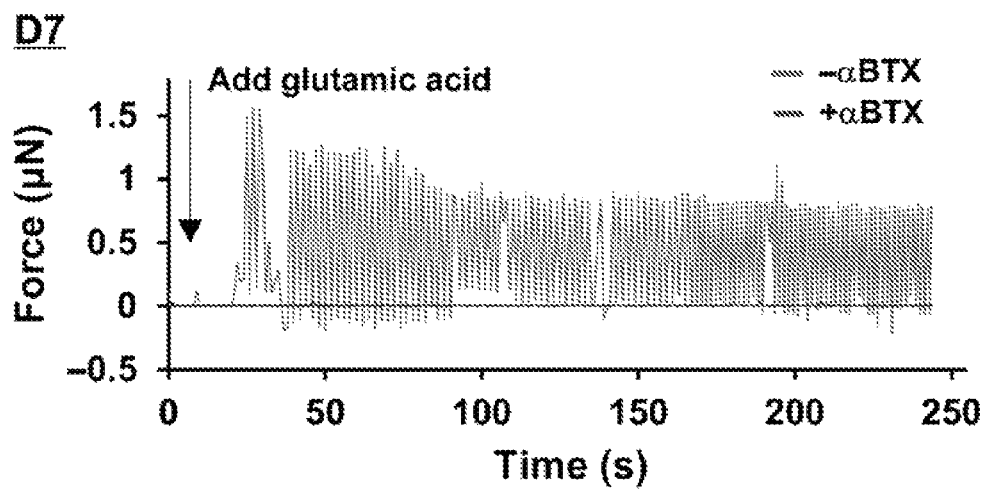
Figure 3G:
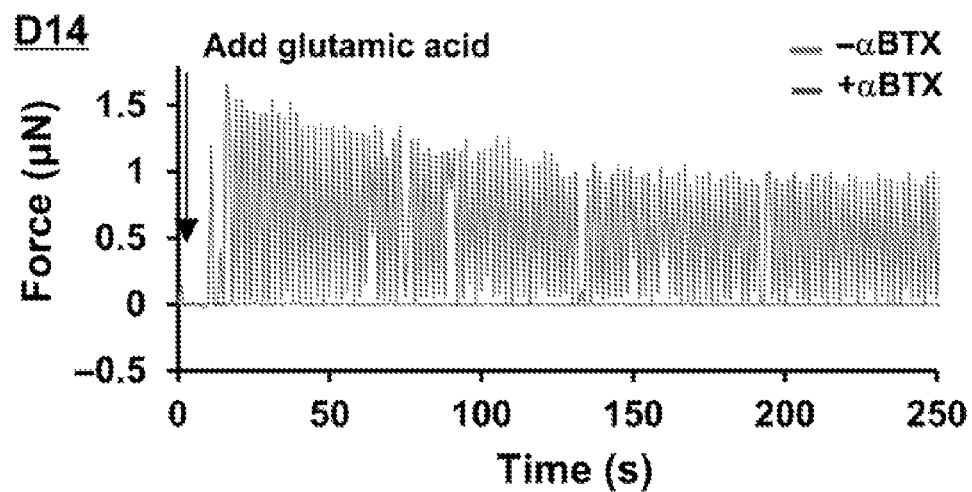

To test whether muscle contraction could be triggered by MN activity, glutamic acid with or without α-bungarotoxin (aBTX), an nAChR antagonist was used (FIGS. 3E-3G). No muscle contraction was observed on day 4, but muscle contraction was observed on day 7 and muscle force increased by day 14 (FIGS. 3E-3G). In the presence of αBTX, muscle contraction was completely inhibited on days 7 and 14. This inhibition indicated that muscle contraction was triggered by MN activity, not by spontaneous muscle fiber movement.

To define the relationship between activity of Ca2+ and muscle contraction, Ca2+ imaging of the muscle fiber was conducted, while displacement maps indicated the spatial distribution of muscle contraction. Ca2+ imaging showed the spatial synchronicity of the calcium transients and local muscle contraction. Muscle contractions occurred at regular intervals, approximately every 0.5 s. In contrast, the time between calcium transients in the muscle fiber was more random. The mean frequency of muscle contraction was slightly lower than the mean Ca2+ oscillation. Almost all the muscle contractions were synchronized to Ca2+ activity in the muscle fiber bundle.

Example 3: Excitotoxicity Induced by Excess Glutamic Acid Treatment Mimics ALS Pathogenesis Glutamate (glutamic acid) is widely recognized as one of the major factors contributing to ALS pathogenesis (Blasco et al., *Curr. Med. Chem.* 21, 3551-3575 (2014)). Prolonged excitation caused by excess glutamate is known to harm neurons (Plaitakis, *Ann. Neurol.* 28, 3-8 (1990)). Normally, glutamic acid is cleared from neurons via several pathways [e.g., neuron-neuron and neuron-astrocyte junctions (Seifert et al., *Nat. Rev. Neurosci.* 7, 194-206 (2006))]; however, patients with ALS are unable to remove glutamate and therefore suffer from MN excitotoxicity because of their low threshold of activation, resulting in neuron death. The prevention of MN excitotoxicity is thought to be the mechanism of action of riluzole, one of the symptomatic ALS treatments.

Figure 4A:
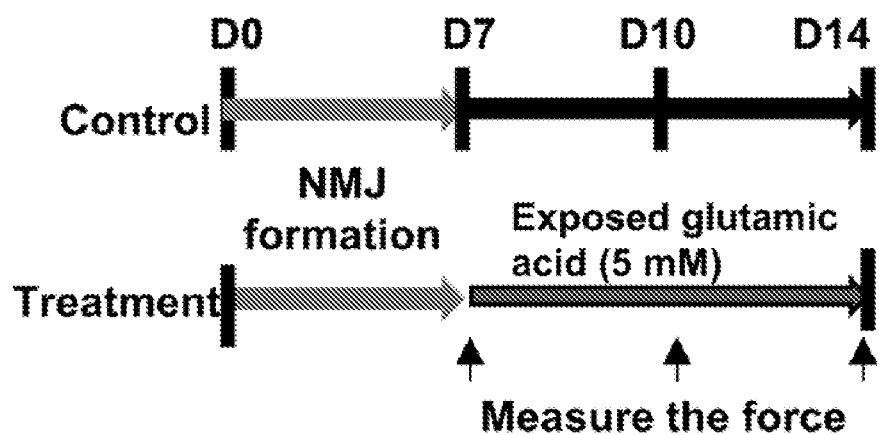
FIG. 4A is a diagram showing the time scale of glutamic acid treatment. After formation of the motor unit with NMJ by D7, glutamic acid (5 mM) treatment was started alongside the control. Muscle contraction was measured on D7, D10, and D14 by applying glutamic acid (0.1 mM).
Figure 4B:
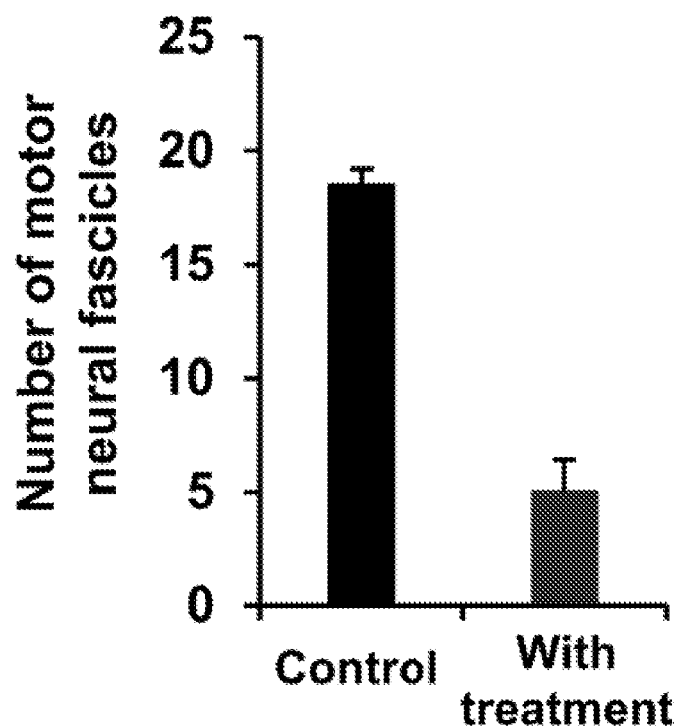
FIG. 4B is a bar graph showing the number of motor neural fascicles with glutamic acid treatment at D14 is less than that of control. n=2.
Figure 4C:
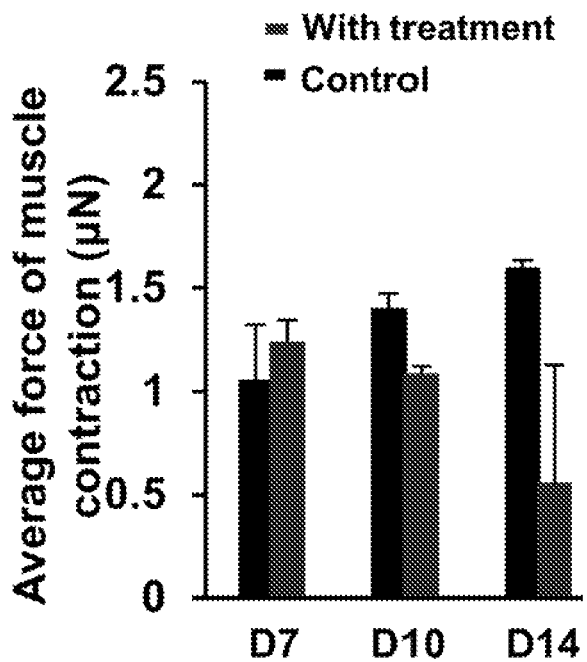
FIG. 4C is a bar graph showing the average force of muscle contraction with treatment over time. n=2.
Figure 4D:
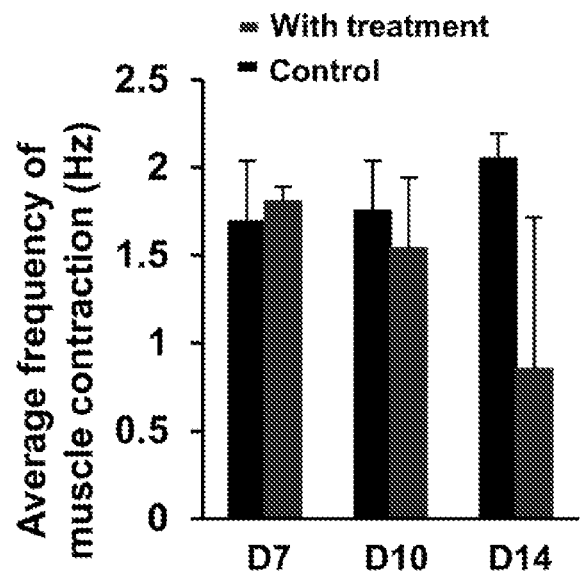
FIG. 4D is a bar graph showing the average frequency of muscle contractions with treatment over time. Average contraction force fell from ~1.3 to 0.5 pN, and frequency was also reduced from 1.8 to 0.7 Hz. n=2.

To mimic this, a high concentration of glutamic acid was added to an established 3D motor unit model. After 7 days of coculture, glutamic acid was added to the motor unit model culture for an additional 7 days, and muscle contraction force was observed (FIG. 4A). As described above, robust NMJs were formed and thick MN fibers were observed by day 14. In contrast, in the presence of excess glutamic acid, no thick MN fibers (MN fascicles) were formed (FIG. 4B); only thin MN fibers and neurite segmentation were observed. Quantitative measurement of muscle contraction revealed that, in the absence of excess glutamic acid, muscle contraction forces increased over time (FIG. 4C). In contrast, muscle contraction forces relatively decreased in the presence of excess glutamic acid. Furthermore, the muscle contraction frequency also dropped in the presence of excess glutamic acid compared with control (FIG. 4D). The mean contraction force and frequency were different in the two groups, especially on day 14 (FIGS. 4C and 4D).

Figure 4E:
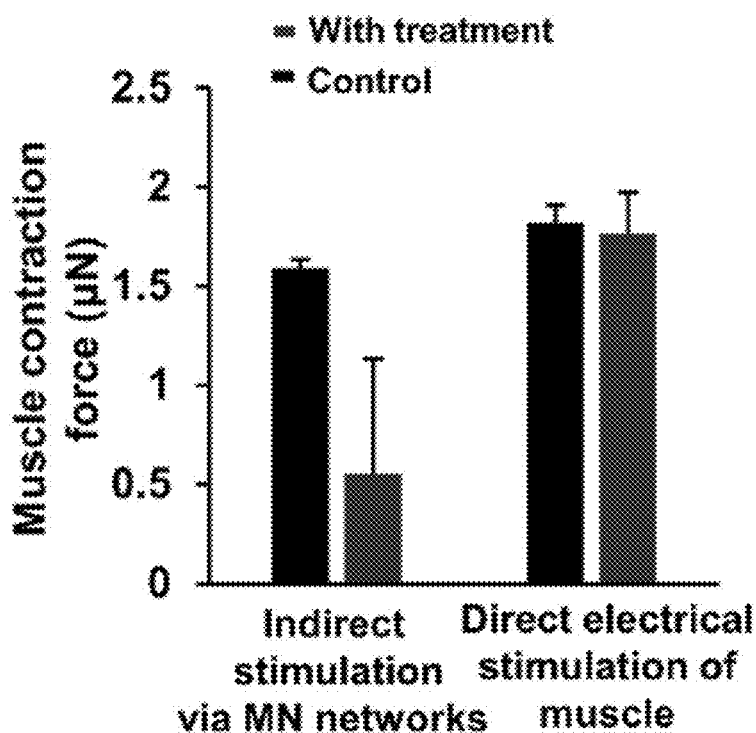
FIG. 4E is a bar graph showing the difference of muscle contraction force between chemical and electrical stimulation. Electrical stimulation produced higher muscle contractility compared to treatment of glutamic acid via MN activity. n=2. Error bars±SD.

Excess glutamic acid treatment up to day 14 mainly caused a neurotoxic effect but no observable myotoxicity; note that while no significant difference was observed with electrical stimulation at day 14, a significant loss of function can be seen with chemical stimulation (FIG. 4E). Prolonged treatment with excess glutamic acid (up to 21 days) led to neurite regression and muscle atrophy, judging from the morphology. As a result, no muscle contraction was observed at 21 days by either mode of activation. This might have been caused by excessive muscle activation and overtraining of the stimulated MNs, as well as rapid depletion of nutrients in the culture medium during days 14 to 21. These results indicate that long-term excess glutamic acid causes MN dysfunction and neuronal cell death along with thick neurite regression and decreased muscle contraction force in the 3D microfluidic devices. In addition, the 3D motor unit model was treated with tetrodotoxin (TTX), which completely prevented muscle contraction. After rinsing away the TTX, muscle contraction partially recovered. This demonstrates that the 3D motor unit model can be used not only for investigating excitotoxicity (such as that associated with ALS and other MN diseases) but also for carrying out exogenous neurotoxicity studies using various chemical compounds.

Example 4: 3D ALS Motor Unit Model in a Microfluidic Device

Materials and Methods
Transfection of the Channelrhodopsin-2 Gene into hESC— and iPSC-Derived NSCs from a Patient with ALS hESC-derived NSCs and iPSC-derived NSCs from a patient with sporadic ALS were infected with an AAV-CAG-ChR2H134R-tdTomato-WPRE plasmid to express a mutated variant of the light-sensitive ion channel, channelrhodopsin-2H134R. AAV-CAG-hChR2H134R-tdTomato was a gift from K. Svoboda (Addgene plasmid no. 28017) (Mao et al., *Neuron* 72, 111-123 (2011)). Adeno-associated virus (AAV) particles were also provided by Addgene. Both types of NSCs were plated in laminin-coated six-well plates at a density of $5.0 \times 10^5$ cells per well and cultured for 2 days. The cells were then incubated for 24 hours with AAV particles containing the plasmid and maintenance culture medium. The cells were cultured for 4 days, expanded for another 3 days, and sorted by fluorescence-activated cell sorting (BD Biosciences, FACSAria II) with strong expression of tdTomato. The transfection efficiency of hESC-derived NSCs and ALS-iPSC-derived NSCs was 77 and 68%, respectively. The channelrhodopsin-2 (ChR2)-NSCs were then replated in laminin-coated six-well plates. To create neurospheres, both ChR2-NSCs were dissolved using Accutase to obtain single cells.

Snp Genotyping

Genomic DNA from iPSC-derived NSCs from the patient with ALS and the control (hESC-derived NSCs) was extracted using a PureLink Genomic DNA Mini Kit (Thermo Fisher Scientific). PCR-based genotyping was performed with rhAmp SNP Genotyping Master Mix and rhAmp Reporter Mix (Integrated DNA Technologies, Coralville, IA, USA) using a 7900HT Fast Real-Time PCR System (Applied Biosystems). Three types of TDP-43 mutation were analyzed [M337V (dbSNP: rs80356730), Q343R (dbSNP: rs80356731), and G298S (dbSNP: rs4884357)]. Two SOD1 mutations were analyzed [A4V (dbSNP: rs121912442) and G93A (dbSNP: rs121912438)]. Five samples (experimental replicates) were used for PCR measurement.

Whole-Exome Sequencing

Genomic DNA from iPSC-derived NSCs from the patient with ALS and the control (hESC-derived NSCs) was extracted using a PureLink Genomic DNA Mini Kit (Thermo Fisher Scientific). Whole-exome sequencing was done in the Broad Genomics Platform at the Broad Institute using Standard Exome v5 Sequencing Methods, and whole-exome libraries were constructed and sequenced on an Illumina HiSeq 4000 sequencer with the use of 151-bp (base pair) paired-end reads. Library construction was performed as described by Fisher et al., *Genome Biol.* 12, R1 (2011)) with some slight modifications. Cluster amplification of the templates was performed according to the manufacturer's protocol (Illumina) using the Illumina cBot. Flowcells were sequenced on HiSeq 4000 Sequencing-by-Synthesis Kits and then analyzed using RTA2.7.3. Bam file was sorted and exome variants were extracted using a SeqMule automated pipeline (Guo et al., *Sci. Rep.* 5, 14283 (2015)), (Bowtie, GATK, SAMtools, SOAPsnp, and Freebayes). Variant data were visualized using Integrative Genomic Viewer.

Results

Figure 5A:
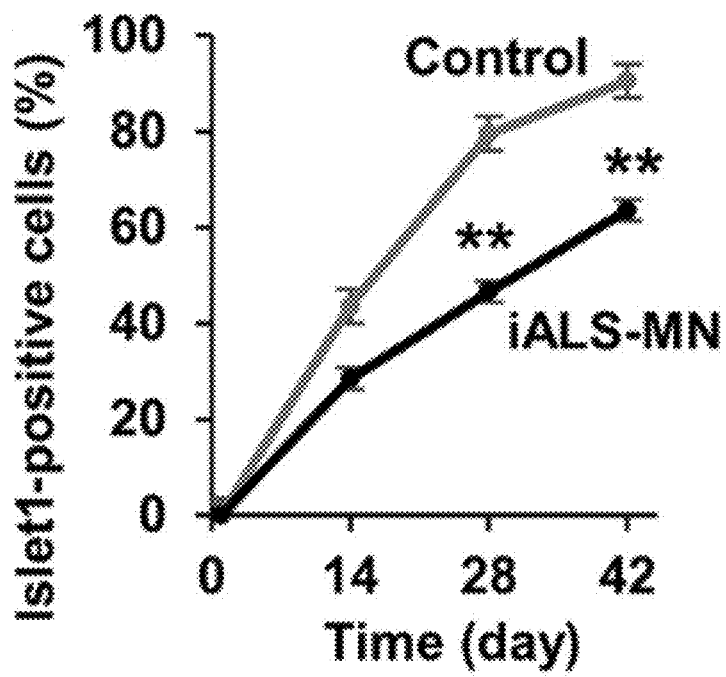
FIG. 5A is a line graph showing the percentage of islet1-positive cells of iALS-MN compared to control (ESC-derived MNs) (counting 100 cells, n=5).

To create an ALS patient-specific motor unit model, iPSC-derived NSCs from a patient with sporadic ALS were used (iALS-MN). After differentiation into MNs, there was a significant decrease in the percentage of islet1-positive cells compared with hESC-derived MNs (FIG. 5A). In addition, mRNA expression of TDP-43 was higher than that in the hESC-derived MNs (FIG. 5B), whereas the mRNA expression of neurofilament light (NEFL) chain and neurofilament medium (NEFM) chain significantly decreased. There were marked differences in neurite length after the differentiation to MNs in 2D culture. In addition, TDP-43, which is normally only found in the nucleus, aggregated in both the cytoplasm and nucleus in the iALS-MNs.

On the basis of single-nucleotide polymorphism (SNP) genotyping and whole-exome sequencing, the iPSC-MNs from the patient with ALS in this study had a heterozygous G298S TDP43 mutation and no M337V or Q343R TDP43 mutations, or A4V or G93A SOD1 mutations. This result (regarding the heterozygous G298S mutation) is consistent with typical genetic features of MNs from patients with ALS carrying TDP-43 in previous studies (Egawa et al., *Sci. Transl. Med.* 4, 145ra104 (2012), Kiskinis et al., *Cell Stem Cell* 14, 781-795 (2014)). In addition, whole-genome sequencing found various SNP mutations such as C9orf72, TBK1, OPTIN, FUS, ALS2, ATG family, BECN1, ULK1, and ULK2, which are associated with ALS pathogenesis and autophagy (Tables 1 and 3).

Since the iPSC-MNs and control cells were transfected with the channelrhodopsin-2[H134R] gene, neural activity and muscle contraction could individually be stimulated in the absence of glutamic acid. Using the optogenetically induced iALS-NSCs, iALS-MN spheroids were created, with hESC-derived MN spheroids as the control. Quantitative PCR analysis showed no significant differences in the expression of Olig2, HB9, or GFAP, although the expression of islet1, ChAT, SMI-32, and Synapsin I decreased after 45 days of differentiation (FIG. 5A). These results indicate that differentiation efficiency does not differ significantly between iALS-MNs and hESC-MNs but iALS-MNs lack gene profiles related to neurofilament formation, acetylcholine synthesis, and synapse formation. In particular, the low expression of ChAT severely impairs motor unit function because ChAT regulates the interaction between MNs and muscle cells via NMJs (Misgeld et al., Neuron 36, 635-648 (2002)). In addition, immunostaining showed that GFAP-positive cells (astrocytes) were found in the iALS-MN spheroids at the same level as in the hESC-MN spheroids. The percentage of HB9-positive cells was the same between the hESC-MN spheroids and the iALS-MN spheroids, but the proliferation rates and spheroid diameters were different.

Figure 5B:
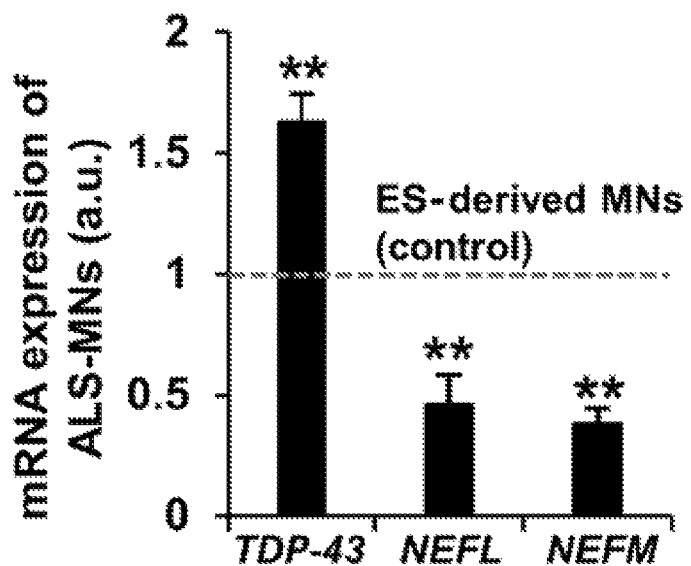
FIG. 5B is a bar graphs showing TDP-43 expression is higher than that of control, whereas expression of NEFL and NEFM is lower than that of control. n=3. Scale bars, 20 μm. a.u., arbitrary units.
Figure 5C:
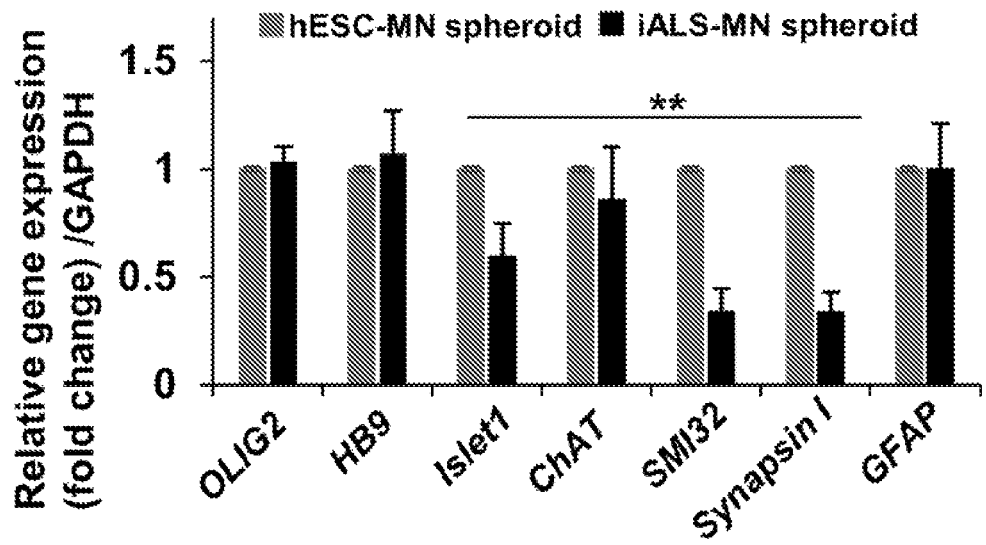
FIG. 5C is a bar graphs showing a comparison of mRNA expression on D45 related to MN differentiation between iALS-MN spheroids and ESC-derived MN spheroids in OLIG2, HB9, GFAP, islet1, ChAT, SMI-32, and Synapsin I. n=8.
Figure 5D:
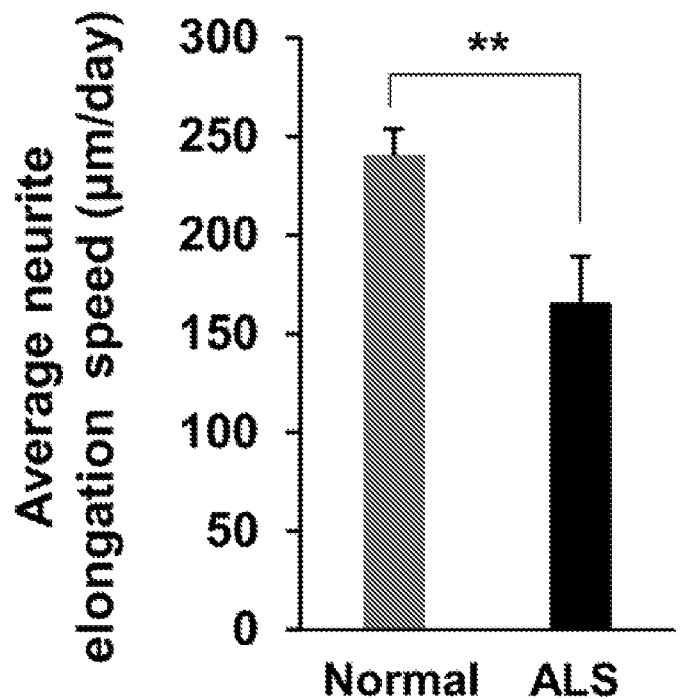
FIG. 5D is a bar graphs showing the average neurite elongation speed in the ALS motor unit compared to control.
Figure 5E:
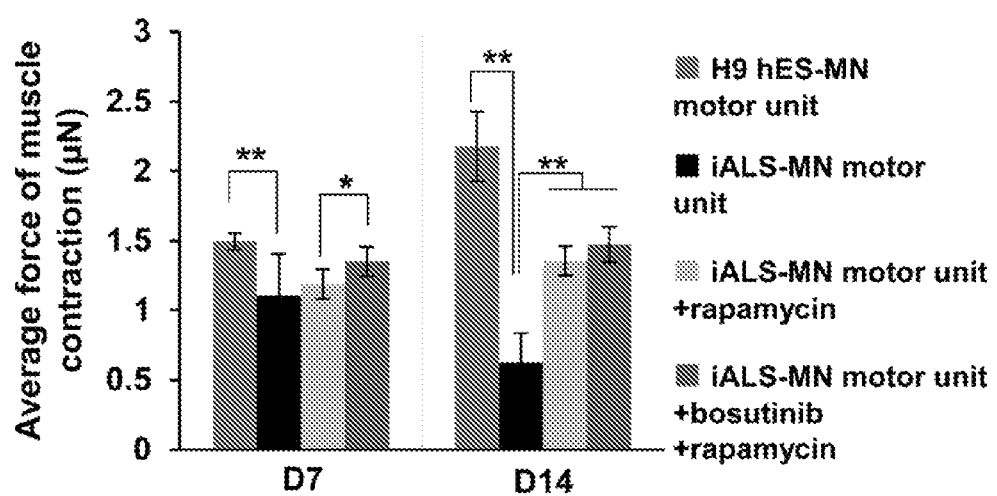
FIG. 5E is a bar graphs showing treatment of potential drugs (bosutinib and rapamycin) to the ALS motor unit model. n=4. Muscle contraction of the ALS motor unit was weaker than that of the ES-derived motor unit without drug treatment on D7 and D14. No significant effect of the drug treatments on D7. However, significant neuroprotection by treatments can be seen on D14.
Figure 5F:
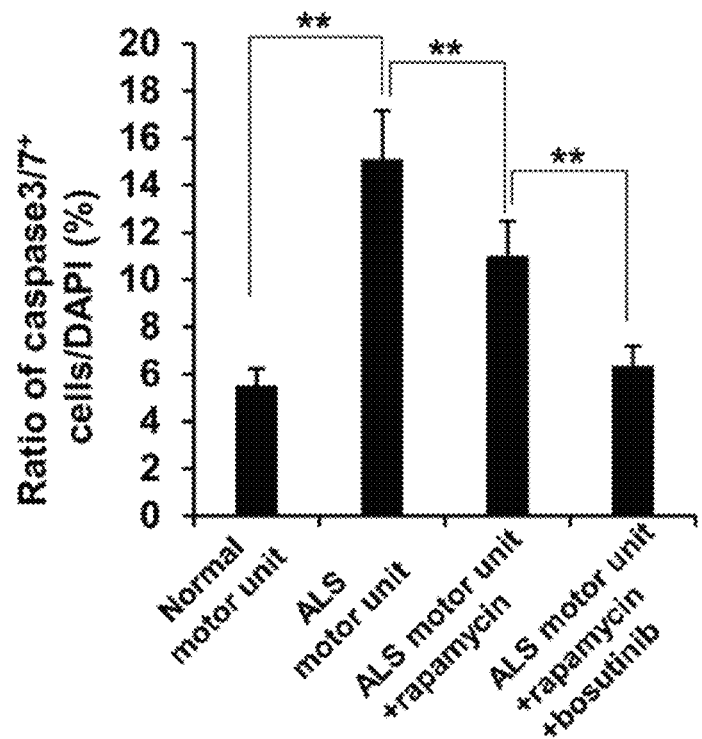
FIG. 5F is a bar graph of caspase3/7-positive cells/DAPI (%) with or without treatment with rapamycin and rapamycin/bosutinib. After D14 of culture in the microfluidic system with the MN spheroid, muscle fiber was live stained for caspase3/7 and then stained for α-actinin and DAPI. n=2. Scale bars, 100 μm. *$P<0.05$; $P<0.01$, Student's t test and two-way ANOVA. Error bars±SD. Characterization of iPS-derived MN from a sporadic ALS donor.

To establish the ALS motor unit, heterogeneous iALS-MN spheroids were injected into the microfluidic devices with 3D muscle fiber bundles. Although neurite elongation in the iALS-MNs was slightly slower compared with the control (FIG. 5D), ALS motor units with NMJs were obtained in at least 7 days. After 14 days of coculture (42 days after differentiation), thick nerve fibers were observed in the collagen gel. However, fewer thick fibers were observed compared with the hESC-derived motor unit (FIG. 5H). This morphological difference was reflected in the phenotype (FIG. 5L), neurite length (FIG. 5G), and elongation speed of the iALS-MNs (FIG. 5D).

To study MN neuroprotection, the ALS and control models were treated with bosutinib (an ALS drug candidate that inhibits the Src/c-Abl pathway) and rapamycin [an ALS drug candidate that inhibits the mechanistic target of rapamycin (mTOR) pathway and induces autophagy activation by targeting proteins such as TDP-43 (Imamura et al., *Sci. Transl. Med.* 9, eaaf3962 (2017))]. On day 7, there was little difference in the optical stimulation-induced muscle contraction force between the ALS and control models with [~1.1 µN (0.13 mN/mm2)] or without treatment [~1.2 to 1.3 N (0.15 to 0.17 mN/mm2); FIG. 5E]. However, treatment with rapamycin or cotreatment with bosutinib and rapamycin significantly prevented the reduced muscle contraction force by day 14, along with neuroprotection (FIG. 5E). In the presence of these drugs, the number of caspase3/7-positive cells [associated with muscle atrophy (Dupont-Versteegden, *World J. Gastroenterol.* 12, 7463-7466 (2006))] in the muscle fiber bundle decreased compared with the condition without drugs (FIG. 5F). This muscle atrophy could be due to a decrease in the secretion of ciliary neurotrophic factor (CNTF) (FIG. 5J) or increased inflammatory cytokine concentrations via up-regulation of nuclear factor κB (NF-κB) signaling (FIG. 5K). These results indicate that, with the tested drugs, the ALS patient-derived motor unit model exhibits less reduction in muscle force and less MN neurotoxicity.

Figure 6A:
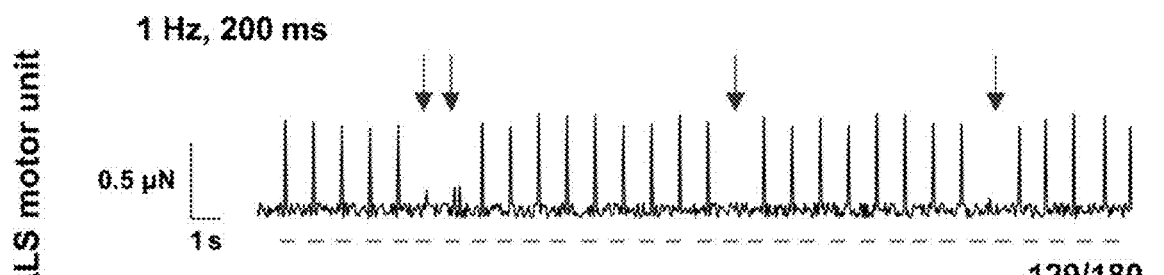
FIGS. 6A-6C are plots showing muscle contraction force by optical stimulation without drugs and with rapamycin and cotreatment of rapamycin and bosutinib. Arrows indicate the absence of muscle contraction with light stimulation. Dashed lines indicate times of light stimulation.
Figure 6B:
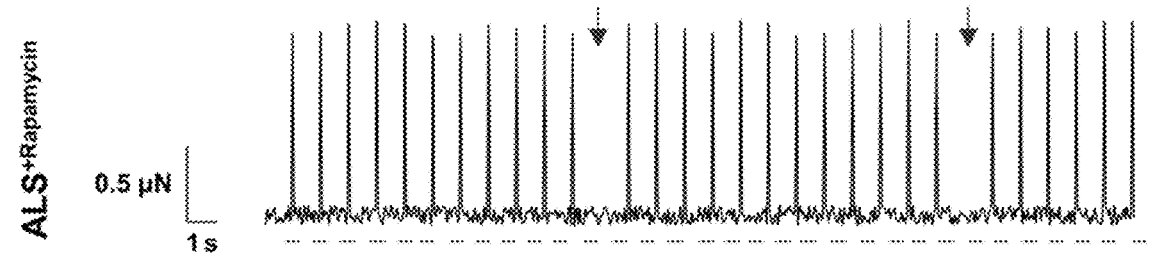
Figure 6C:
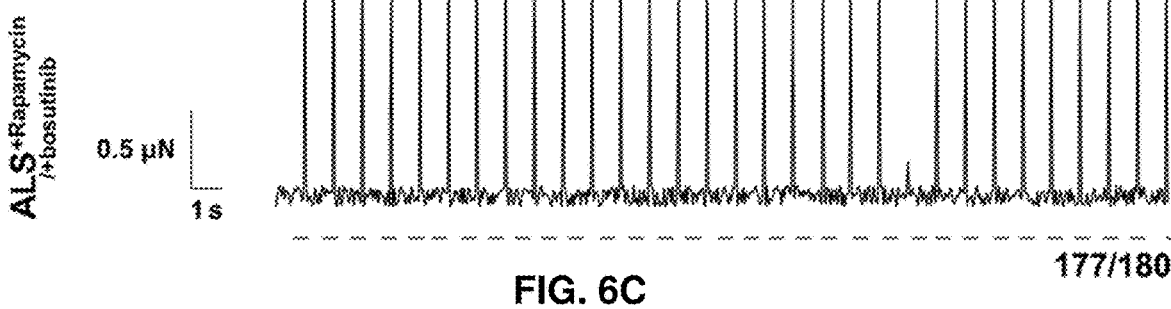
Figure 6D:
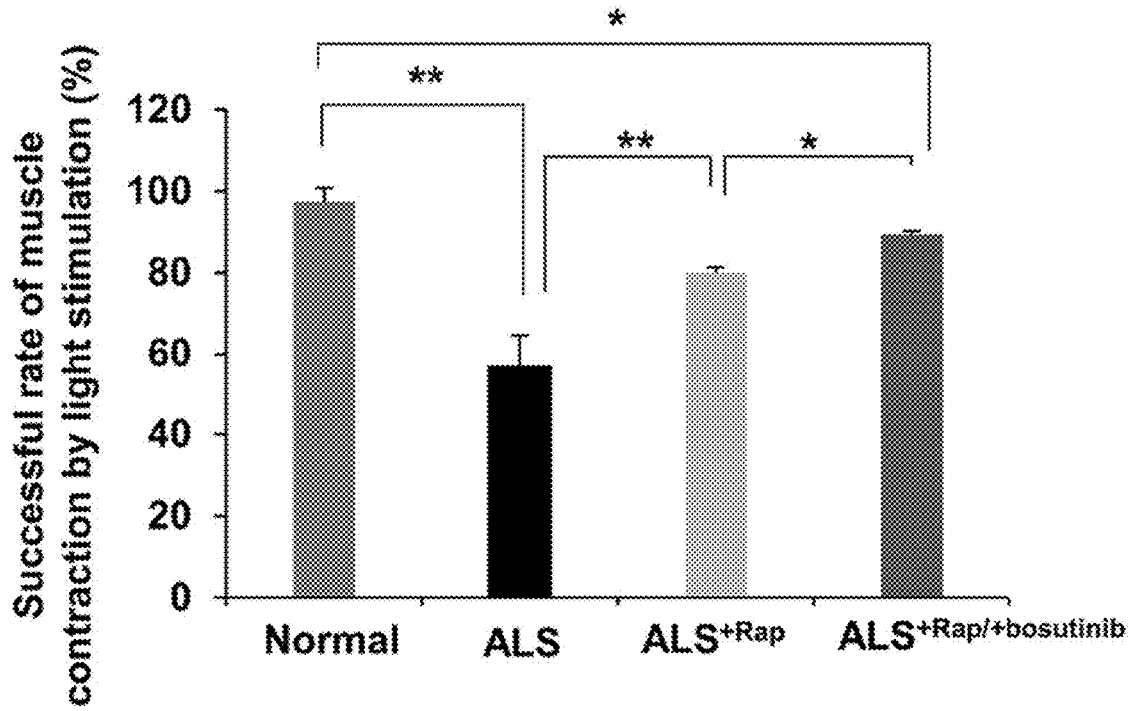
FIG. 6D is a bar graphs showing the rate of muscle contraction by light stimulation in three cases. The ALS motor unit often misses muscle contraction (~56%), whereas drug treatments returned the success rate of muscle to nearly normal; n=6. ALS, ALS+Rap, ALS+Rap/+bosutinib; n=4.
Figure 6E:
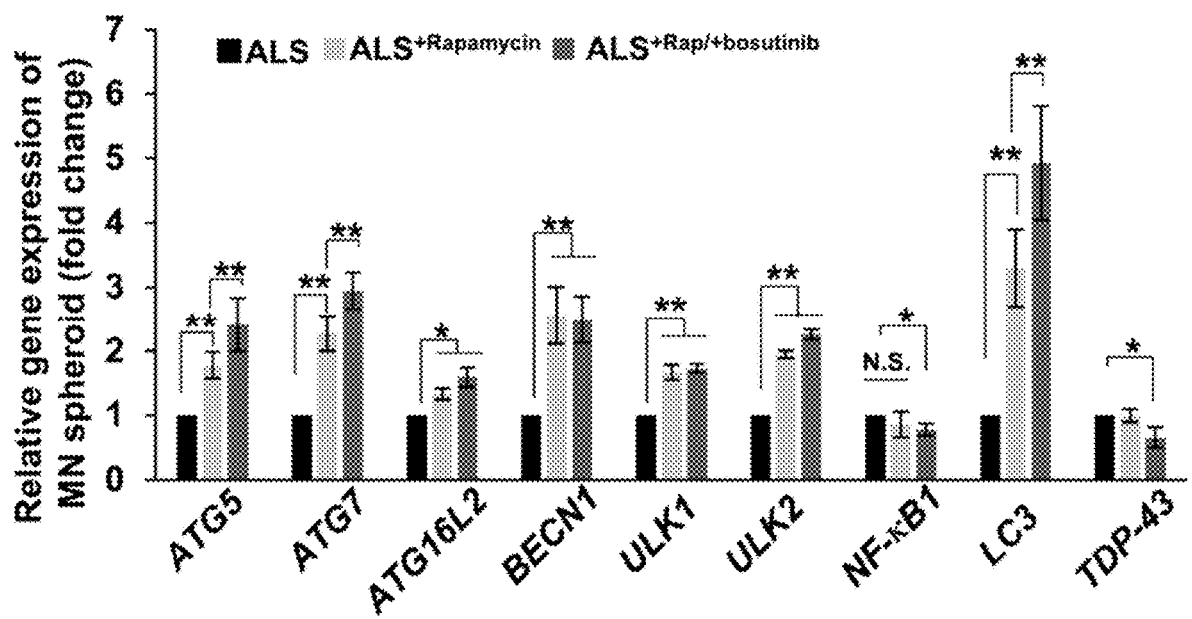
FIG. 6E is a bar graph showing gene expression change (ATG5, ATG7, ATG16L2, BECN1, ULK1, ULK2, and LC3) of the MN spheroid after D14 of culture (ALS, ALS+Rap, ALS+Rap/+bosutinib) n=4.
Figure 6F:
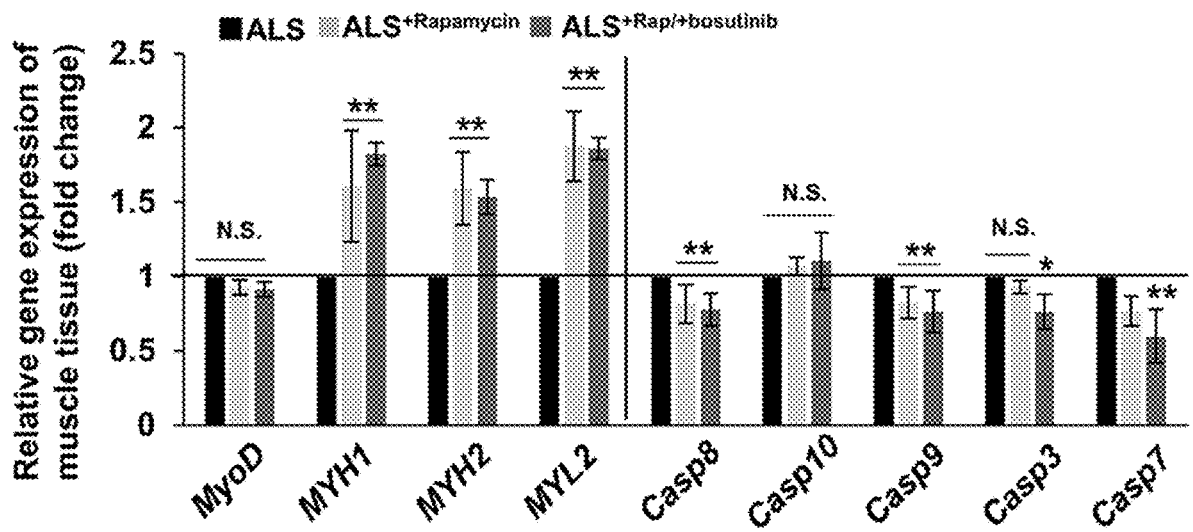
FIG. 6F is a bar graph showing changes in expression of genes related to the myogenesis and apoptosis of muscle tissue after D14 of culture with drug treatment (ALS, ALS+Rap, ALS+Rap/+bosutinib). n=4. *$P<0.05$; **$P<0.01$, two-way ANOVA. Error bars±SD.

Furthermore, these drugs also affected the response of muscle contraction induced by 1-Hz optical stimulation. In the ALS motor unit model, muscle contraction sometimes failed to occur after light stimulation (~32.3%, n=180) (FIGS. 6A, 6D). After treatment with rapamycin or cotreatment with rapamycin and bosutinib, these missed contractions were suppressed down to ~16.1 and ~9.6% (n=180; FIGS. 6B-6D). Consistently, the expression of ATG5, ATG7, ATG16L2, BECN1, ULK1, ULK2, and LC3 genes was significantly increased in the presence of rapamycin and bosutinib (FIG. 6E). This activation of autophagy helped the degradation of TDP-43 and its segments (e.g., TDP-25 and TDP-35) to induce neuroprotection. Furthermore, the expression of MYHI, MYHII, and MYLII genes (myogenesis markers) was also increased, and the expression of caspase genes tended to decrease. In contrast, no significant difference in MyoD expression was observed, although it is known that rapamycin (an mTOR inhibitor) down-regulates myogenesis (FIG. 6F).

Example 5: Drug Treatment Via an EC Barrier

Materials and Methods
iPSC-Derived ECs

Figure 7A:
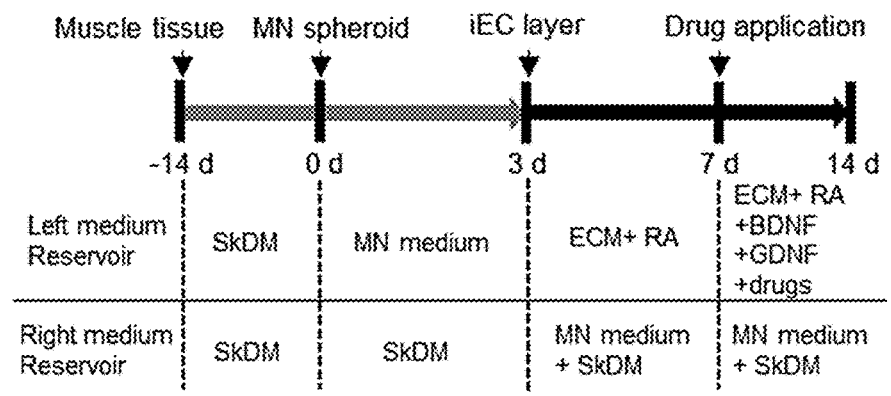
FIG. 7A is a culture scheme.
Figure 7B:
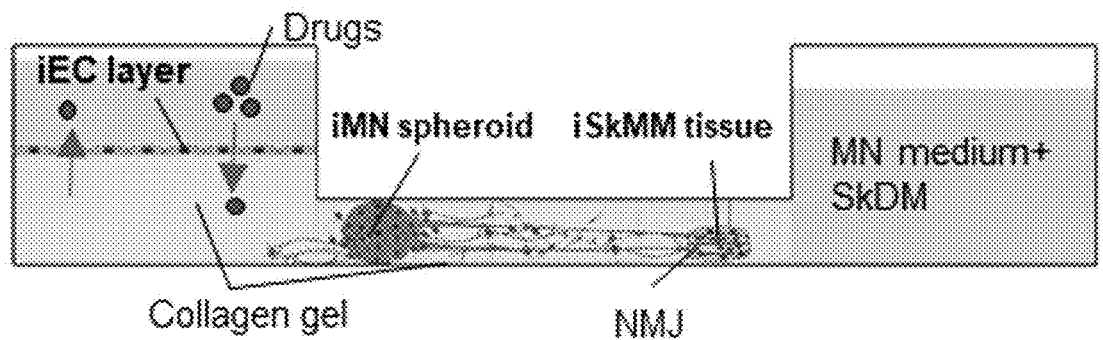
FIG. 7B is an illustration of a culture system, of iEC layer, iALS-MN spheroid, and iPSC-derived skeletal muscle fiber bundle.

Human iECs (iCell ECs, Cellular Dynamics Technology) were maintained on fibronectin coating (50 µg/ml) with a VascuLife VEGF Endothelial Cells Medium Complete Kit (Lifeline Cell Technology) and iCell growth supplement.
Formation of iEC Layer and Drug Exposure To test drug application via an EC layer, type I collagen gel was poured into the left medium reservoir after injection of iALS-derived MN spheroids. The iECs (iCell ECs) were then seeded into the left well on the collagen gel ($5.0 \times 10^5$ cells/ml). To accelerate differentiation into brain-specific ECs, RA (20 µM) was added (FIG. S10A). After 7 days of coculture, drugs were applied to the left medium reservoir.
Results To use this model for translational medicine research, pharmacological drug efficiency is important. In particular, drug penetration via EC barriers (such as the blood-brain barrier and blood-spinal cord barrier) should be considered when investigating drugs to treat central nervous system (CNS) diseases. To mimic this process, iPSC-derived ECs (iECs) were seeded in the left medium reservoir on a collagen gel layer to create an EC layer (FIG. 7A-7B). The iECs differentiated toward a brain-specific EC phenotype after retinoic acid (RA) was added (Lippmann et al., *Sci. Rep.* 4, 4160 (2014)); they were then cocultured with iALS-MN spheroids in the microfluidic device, resulting in the formation of a tight iEC monolayer expressing ZO-1, occludin, and P-glycoprotein (P-gp). The low permeability was confirmed by adding 40-kDa dextran into the left medium reservoir with and without an iEC layer. To culture three types of cells simultaneously, the culture medium composition was modified (FIGS. 7A-7B). By coculturing with ECs and adding endothelial medium, muscle contraction force slightly decreased (FIGS. 7D-7G, no drug condition, with EC), but no changes were observed in MN or muscle viability compared to the nonendothelial barrier protocol. However, in terms of MN phenotypes, slightly thinner neural fibers were observed at day 14.

Rapamycin or bosutinib treatment via the iEC layer decreased muscle contraction force [~1.5 µN (0.2 mN/mm2)] compared with configurations without the iEC layer [~0.5 µN (0.06 mN/mm2); FIGS. 7D-7H]. Cotreatment with rapamycin and bosutinib significantly increased muscle contraction force and synchronicity compared with either single agent treatment, though the force decreased slightly in the cotreatment plus iEC layer condition in comparison with the cotreatment without an iEC monolayer. The bosutinib concentration can be regulated by the P-gp efflux transporter in vivo (Redaelli et al., *J. Hematol. Oncol.* 8, 81 (2015)). In this model, P-gp expression in the iEC monolayer was decreased by treatment with rapamycin and cotreatment with rapamycin and bosutinib, inhibiting the transport of bosutinib from the basal to the apical side of the iEC layer in the cotreatment condition. These results indicate the usefulness of an EC barrier as a means of investigating the role of vascular permeability in neuroprotection efficacy and muscle contraction (FIGS. 7D-7H).

The Examples illustrate a 3D human motor unit model in a microfluidic device formed by coculturing MN spheroids and 3D muscle fiber bundles. Muscle contraction could be induced by MN activity (after NMJ formation) and chemical and optical stimulation (FIGS. 3E-3G and 5A-5F). Previous results indicate that a mouse motor unit model could be created using mouse ESC-derived MNs and C2C12 cells in different microfluidic systems (Uzel et al., *Sci. Adv.* 2, e1501429 (2016)). However, important species differences between mice and humans likely contribute to the failure in clinical trials of drug candidates that have been identified via screening using an ALS mouse model (Inoue and Yamanaka, *Ther.* 89, 655-661 (2011)). This highlights the importance of using cells that are derived from a human source. In addition, the microfluidic device architecture was improved to allow higher-throughput screening of single or combination therapies.

Therefore, the model represents an important advance in the simulation of human physiological and pathological conditions associated with motor units and NMJs, which is useful for investigating the mechanisms underlying ALS and for drug screening.

Motor unit dysfunction is involved in many diseases besides ALS, such as myasthenia gravis, muscular dystrophy, spinal and bulbar muscular atrophy, and spinal muscular atrophy (Nageshwaran et al., *BMJ* 349, g4052 (2014)). Heterogeneous MN spheroids were generated with MNs and astrocytes. This heterogeneity was considered to be important in the study of ALS pathogenesis because recent findings have implicated reactive astrocytes in ALS pathogenesis and MN degeneration (Tripathi et al., *Stem Cell Rep.* 9, 667-680 (2017)). An MN organoid that includes MNs and astrocytes (rather than pure MNs) is believed to be suitable to act as a model for investigating ALS.

To mimic the pathological conditions of motor units of patients with ALS, the 3D human motor unit were treated with excess glutamic acid. The treatment caused MN excitotoxicity along with the regression of thick neurite fibers, resulting in a weak muscle contraction force (FIG. 4C). Furthermore, long-term MN excitotoxicity (after exposure to glutamic acid for 14 days) also causes muscle atrophy due to continuous muscle contraction and muscle fatigue. In patients with ALS, astrocytes play an important role in glutamic acid uptake to maintain the inappropriate concentration of glutamic acid between the presynaptic and postsynaptic neurons, and decreased expression of the excitatory amino acid transporter 2 (EAAT2) might be associated with ALS (Yamanaka et al., *Nat. Neurosci.* 11, 251-253 (2008)).

Although MN excitotoxicity was observed in this motor unit model, when astrocytes were cocultured with MNs and skeletal muscle cells, the glutamate concentration threshold increased (Hounoum et al., *Front. Cell. Neurosci.* 10, 118 (2016)). This indicates that glial cells might be needed in the culture model. In addition, TTX treatment led to temporal inhibition of neural activity and muscle contraction as previously demonstrated in an in vitro 3D NMJ model (Kato-Negishi et al., *Adv. Healthc. Mater.* 6, 1700143 (2017)), using other neurotoxins such as curare [another nAChR inhibitor (Morimoto et al., *Biomaterials* 34, 9413-9419 (2013))]. This chemically induced model can be used for testing motor unit neurotoxins and induced disease models such as acquired neuromyotonia.

Figure 5G:
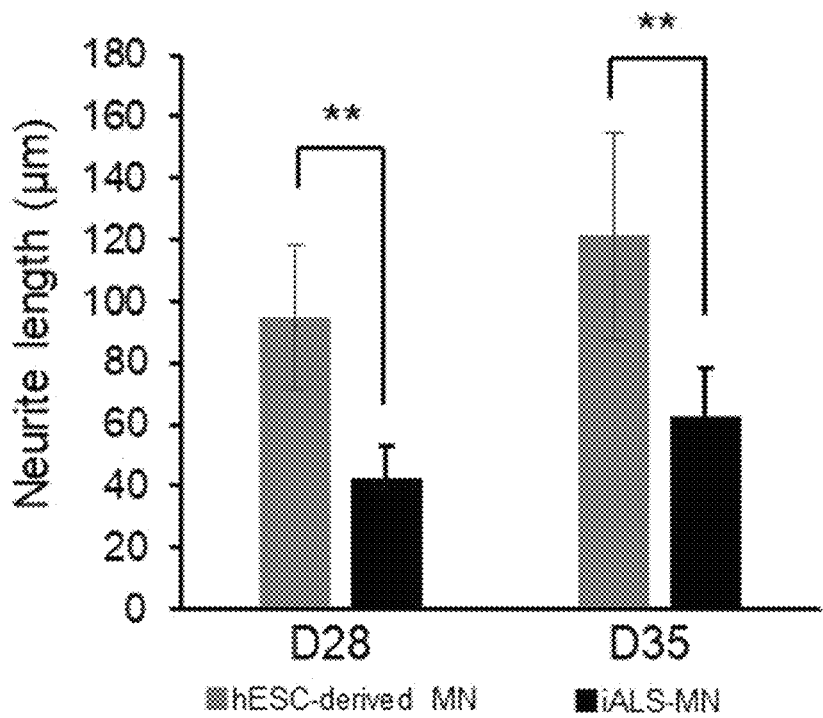
FIG. 5G is a bar graph showing neurite length (μm) neural stem cells differentiating into MN from ALS-derived NSC and ES-derived NSC.
Figure 5H:
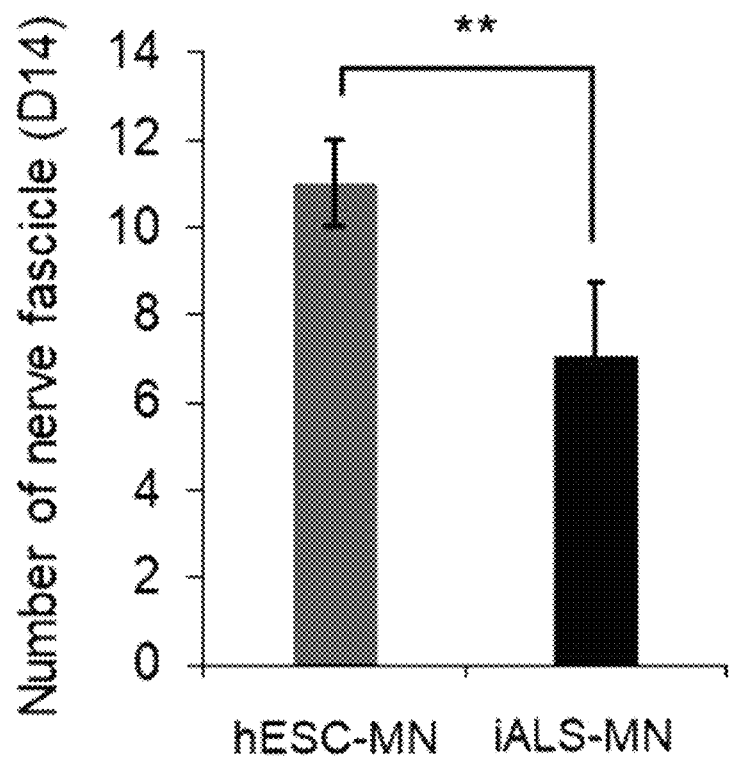
FIG. 5H is a bar graph showing comparing the number of nerve fascicles of ALS-iPS MN to ES-derived MN.
Figure 5I:
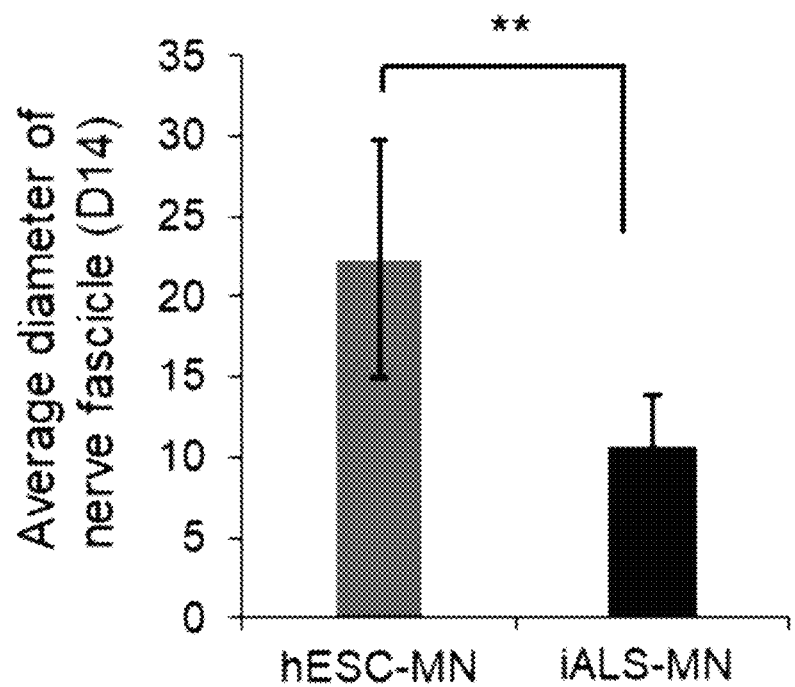
FIG. 5I is a bar graph showing the average diameter of nerve fascicles at D14. (n=4) , $P<0.01$. Student t-test. Scale bars are 50 μm (C, E) and 100 μm (A, F, n).
Figure 5J:
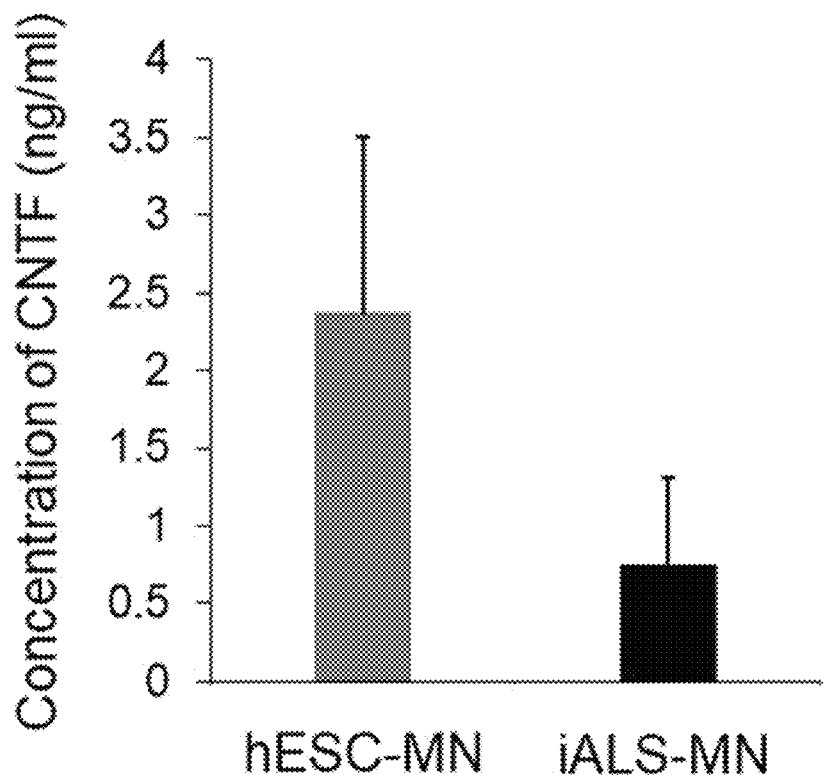
FIG. 5J is a bar graph showing the concentration of CNTF in iALS-MN compared to hESC-MN after co-culture with muscle cells in a microfluidic device. (n=3).
Figure 5K:
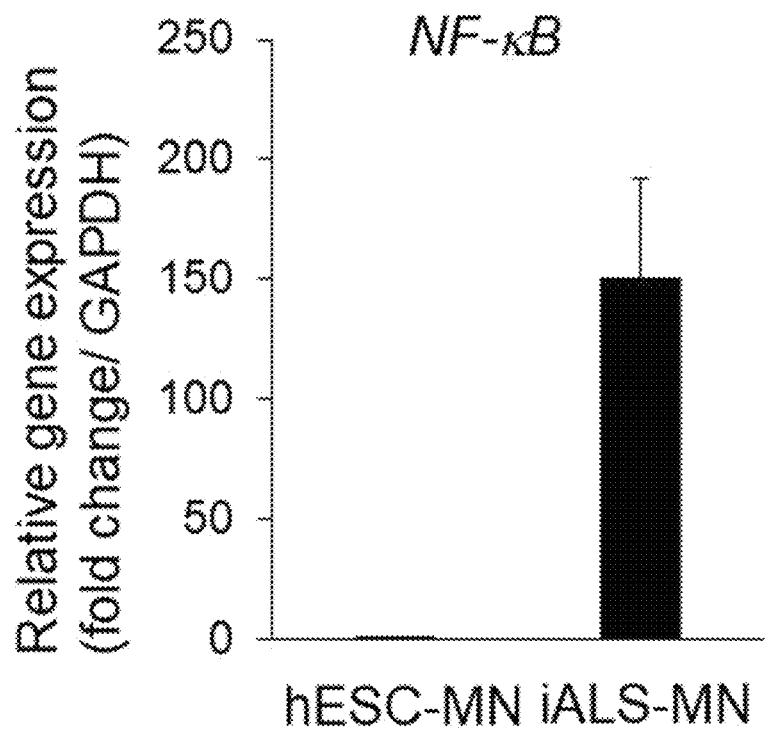
FIG. 5K is a bar graph showing relative expression of NF-kB in MN after co-culture with muscle tissues in microfluidic devices. The expression in iALS-MN significantly increased due to the OPTN mutation via dysfunction of NF-kB suppressive activity. (n=5).
Figure 5L:
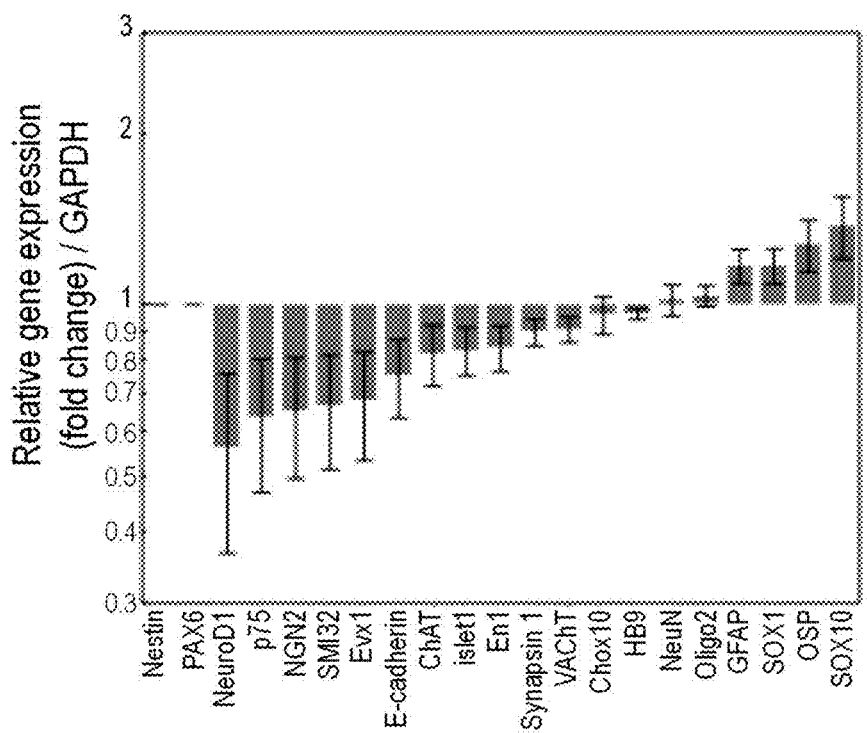
FIG. 5L is a histogram illustrating the phenotypic difference of iALS-MN spheroids compared to ESC-MN spheroids after co-culture with muscle tissues in microfluidic devices. Scale bar is 100 μm.

The formation of an ALS motor unit model was demonstrated using iPSC-derived MNs from a patient with sporadic ALS carrying the TDP-43 gene mutation with an abnormal inclusion of TDP-43 and short neurite elongation (FIG. 5G). TDP-43 is a nuclear protein that regulates transcription and mRNA splicing (Chen et al., *Brain Pathol.* 22, 110-116 (2012)), and it is a major component of ubiquitinated protein aggregations found in patients with sporadic ALS and patients with SOD1-negative familial ALS (Arai et al., *Biochem. Biophys. Res. Commun.* 351, 602-611 (2006)). Therefore, many researchers have focused on TDP-43 degradation in patients with ALS and MNs in vitro. The PCR results also indicated lower expression of NEFL and NEFM in the iALS-MNs (FIG. 5B). Although the iALS-MN spheroids had similar morphology to the hESC-derived MN spheroids (in terms of formation and growth), lower expression of islet1, ChAT, SMI-32, and Synapsin I was found. Accumulating results have implicated specific phenotypes in iALS-MNs, involving reduced neuronal soma size, increased apoptosis, and progressive loss of synaptic activity (Devlin et al., *Nat. Commun.* 6, 5999 (2015)). GFAP expression was the same as that in the control MNs, as measured by PCR (FIG. 5C) and immunostaining. In the process of motor unit and NMJ formation, the iALS-MN neurite elongation speed in collagen gel was slow compared with the normal motor unit model in the microfluidic devices (FIG. 5D). This can be explained by low expression of factors related to neurofilament growth and significant loss of islet1-positive cells involving the mutation of NEFH(SMI-32), as demonstrated by previous findings (Kiskinis et al., *Cell Stem Cell* 14, 781-795 (2014), Devlin et al., *Nat. Commun.* 6, 5999 (2015)).

A remarkable finding was that the muscle contraction force in the ALS motor unit was reduced relative to the normal motor unit, and there was an increase in the number of caspase3/7-positive cells, indicative of apoptosis and muscle atrophy (FIG. 5F). These results indicate that coculturing ALS patient-derived MNs with a normal (non-ALS) skeletal muscle fiber leads to myotoxicity. This is likely caused by neurotoxins and excitotoxicity during long-term culture. Another factor could be the significant loss of secretion of CNTF from MNs that down-regulates muscle protection (FIG. 5J) because CNTF receptor is also expressed in skeletal muscle cells (Hiatt et al., *J. Tissue Eng. Regen. Med.* 8, 963-968 (2014)).

A heterozygous E478G missense mutation associated with OPTN (Table 1) is known to activate the NF-κB pathway (Maruyama et al., *Nature* 465, 223-226 (2010), Nakazawa et al., *Nat. Commun.* 7, 12547 (2016)) because OPTN plays an important role for NF-κB suppressive activity, resulting in neurotoxicity with inflammation. In this model, the expression of NF-κB in iALS-MNs after coculture with muscle tissues was significantly up-regulated compared with ES-MNs (FIG. 5K). This activates downstream pathways and up-regulates secretion of cytokines such as the tumor necrosis factor-α (TNF-α), interleukin family proteins, and cyclooxygenase-2. In this model, TNF-α upregulation might also contribute to muscle weakness along with apoptosis and protein degradation in skeletal muscle cells as drug application down-regulated the NF-κB expression (FIG. 6E). All of the foregoing supports the conclusion that a pathological ALS motor unit model was established in a high-throughput microfluidic device.

Inhibition of the Src/c-Abl pathway has been found to improve neuroprotection, for example, bosutinib and masitinib (Imamura et al., *Sci. Transl. Med.* 9, eaaf3962 (2017)). Bosutinib (which is approved for chronic myelogenous leukemia) showed representative neuroprotection along with the activation of autophagy. It is being tested in a phase 1 clinical trial (NCT02921477). Rapamycin is being tested in a phase 2 clinical trial (NCT03359538). To test these drug candidates in vitro using the model, the ALS motor unit was treated with bosutinib and rapamycin to observe the neuroprotection effect. Both treatments improved neuronal survival and increased muscle contraction force (induced by MN activity), which might have been due to a reduction in cytoplasmic TDP-43 aggregation, NF-κB expression, or skeletal muscle cell apoptosis in muscle fiber bundles (Son et al., *Cell Stem Cell* 9, 205-218 (2011)). Treatment with rapamycin, an mTOR inhibitor, not only improved MN neuroprotection but also indirectly up-regulated muscle contraction and suppressed miscommunication between MNs and muscle tissue, although it is known that inhibition of the Akt/mTOR pathway can enhance muscle atrophy (Bodine et al., *Nat. Cell Biol.* 3, 1014-1019 (2001)). These results provide support for this potential strategy of treating ALS with bosutinib combined with rapamycin, which induces autophagy, to avoid abnormal aggregation of proteins such as TDP-43.

Any drug proposed to treat ALS would need to penetrate the blood-brain barrier and blood-spinal cord barrier. In general, rapamycin (~914 Da) is limited in its ability to penetrate the blood-brain barrier in vivo. Rapamycin treatment across an iEC layer did not improve muscle contraction in this model. A single treatment of bosutinib (~530 Da) via an iEC layer decreased the efficiency of bosutinib compared with administering bosutinib without an iEC layer. It was believed that bosutinib partially leaked through the iEC barrier via the paracellular pathway, but a low concentration of bosutinib was maintained in the basal niche because of the function of the EC efflux pump (an adenosine triphosphate-binding cassette transporter) in the system. However, cotreatment with rapamycin and bosutinib via the EC barrier improved the efficacy of the treatment (FIGS. 7D-H), possibly because rapamycin decreases the expression of the P-gp transporter, the efflux pump that transports bosutinib out of the CNS (FIG. 7C). It has also been shown that a P-gp inhibitor can increase the concentration of a P-gp substrate (such as paclitaxel) in the brain in vivo (Novak, *Nat. Rev. Cancer* 2, 890 (2002)). These results indicate the potential of cotreatment with an mTOR inhibitor, a P-gp inhibitor, and an Src/c-Abl pathway inhibitor for ALS. Therefore, the 3D ALS motor unit model with drug delivery across an EC barrier can be especially useful when evaluating neuroprotection and screening drug candidates, and indicates that the in vitro model can be a robust ALS-on-α-chip technology with MN networks and muscle tissues as well as an EC barrier.

Several modifications are available in terms of MN enhancement and the addition of other cell types. ALS is an age-dependent disease, and MNs require considerable differentiation time for neurogenesis, maturation, and clinical onset of ALS in an in vitro culture. A recent study proposed an artificial acceleration method, in which MNs are genetically manipulated to express progerin to simulate premature aging (Miller et al., *Cell Stem Cell* 13, 691-705 (2013)). Alternatively, direct differentiation into MNs from patient-derived somatic cells is possible by ensuring transgenic expression of transcription factors that induce MN differentiation (Son et al., *Cell Stem Cell* 9, 205-218 (2011)) and by inducing microRNAs (Abernathy et al., *Cell Stem Cell* 21, 332-348.e9 (2017)). In addition, inhibition of the Notch pathway has been shown to accelerate MN differentiation by delaying the cell cycle transition from G1 to S phase (Maury et al., *Nat. Biotechnol.* 33, 89-96 (2015)). These technologies may generate a more mature 3D ALS model.

In addition to the improvement of MN characterization and differentiation, the inclusion of other types of cells such as Schwann cells and microvascular networks can be used to obtain a more robust motor unit. During the developmental process and to maintain homeostasis, Schwann cells regulate MN nerve fiber myelination, improve axonal outgrowth, and have therapeutic potential for spinal cord injury in vivo (Pearse et al., *Glia* 55, 976-1000 (2007)) and even in vitro (Pearse et al., *Nat. Med.* 10, 610-616 (2004)). Moreover, perfusable microvascular networks involving ECs in the microfluidic device would be preferred for long-term maintenance of this ALS motor unit model. They would improve the supply of oxygen and nutrients to the tissues and better mimic the delivery of drug to the CNS. A previously described coculture model with MN spheroids and perfusable vascular networks in microfluidic devices that resulted in improved neural networks and culture medium perfusion improved MN activity (Osaki et al., *Sci. Rep.* 8, 5168 (2018)). Furthermore, vascular networks not only are physiologically relevant but also play an important role in the pathogenesis of ALS, which is accompanied by vascular dysfunction and impaired blood-tissue barrier function (Garbuzova-Davis et al., *Brain Res.* 1469, 114-128 (2012), Winkler et al., *Proc. Natl. Acad. Sci. U.S.A.* 111, E1035-E1042 (2014)).

Furthermore, in these experiments normal human-derived skeletal muscle tissues was used. If patient-derived skeletal muscle cells (Darabi et al., *Cell Stem Cell* 10, 610-619 (2012)) and/or ECs, are used, it is believed that the model can be applied not only to neuropathy (such as that associated with ALS and spinal muscular atrophy) but also to myopathy (such as that associated with Duchenne muscular dystrophy and myasthenia gravis) by forming patient-derived muscle fiber bundles to investigate interactions between muscle atrophy and MN activity and for the purpose of drug testing. Last, because Alzheimer's disease, Parkinson's disease, and epilepsy have been associated with muscle strength (Boyle et al., *Arch. Neurol.* 66, 1339-1344 (2009), Cano-de-la-Cuerda et al., *Am. J. Phys. Med. Rehabil.* 89, 70-76 (2010)), coculture with iPSC-derived cortical neurons from these patients would facilitate investigations of the relationship between these pathologies and muscle strength.

TABLE 1

SNP mutation (whole-exome sequencing), ALS pathogenesis related.

| Category | Gene | SNP mutation, insertion, and deletion |
|---|---|---|
| ALS pathogenesis associated | SOD1 | No variants found |
| | C9orf72 | Chr9: 27558547 C/T HET,<br>chr9: 27561466 —/TGT insertion HOM (rs3063748),<br>chr9: 27567145 C/T HET (rs10757668, UTR) |
| | TARDBP | Chr1: 11082538 A/G HET (rs4884357, G298S),<br>chr1:11082107 —/T insertion HET (rs202106921) |
| | TBK1 | Chr12: 64875787 A/T HET (rs7486100, intron) |
| | NEK1 | Chr4: 170315496 C/T HOM (rs4692721, UTR),<br>chr4: 170482883 A/G HOM (rs560644008, intron)<br>Chr4: 170506703 A/G HOM (rs55679731, intron) |
| | OPTIN | Chr10: 13150991 —/CACA insertion HET (rs111744244),<br>chr10: 13151224 G/A HET (rs2234968, T34T)<br>chr10: 13151245 G/A HET (rs11591687, L41L),<br>chr10: 13158262 C/T HOM (rs2244380),<br>chr10: 13166076 A/G HOM (rs523747, E322K),<br>chr10: 13174098 A/G HET (rs267606929, E478G) |
| | SPG11 | Chr15: 44918690 C/T HET (rs78183930, A695T),<br>chr15: 44943757 A/G HOM (rs3759871, F463S)<br>chr15: 44944037 C/T HET (rs77697105, E370K) |
| | VCP | Chr9: 35056961 C/A HET (rs1053318, UTR),<br>chr9: 35062973 C/T HOM (rs514492, intron) |
| | ATXN2 | Chr12: 1120336754-756 —/GCT deletion (rs10560189),<br>chr12: 112036797 C/T HOM (rs4098854, Q174Q) |
| | ANG | Chr14: 21162053 T/G HET (rs11701, G110G) |
| | CHCHD10 | Chr22: 24108412 G/A HOM (rs9153, Y104Y),<br>chr24: 109744 T/G HOM (rs179468, P16P) |
| | SIGMAR1 | Chr9: 34635598 T/C HOM (rs4879809, UTR) |
| | FIG1 | Chr6: 110106234 A/G HOM (rs10499054, intron),<br>chr6: 110146588 C/T HOM (rs1127775, UTR) |
| | SS18L1 | No variants found |
| | GRN | No variants found |
| | SETX | Chr9: 135152544 A/— deletion HET (rs34769225),<br>chr9: 135202829 T/C HOM (rs543573, I1386V),<br>chr9: 135203231 C/T HOM (rs1183768, G1252R),<br>Chr9: 135203409 A/C HOM (rs1185193, D1192E)<br>chr9: 135206460 A/G HOM (rs9411449, Y359Y) |
| | SQSTM1 | No variants found |
| | TAF1 | No variants found |
| | FUS | Chr16: 31191482 A/G HOM (rs929867, UTR),<br>chr16: 31195279 C/T HOM (rs1052352, Y97Y)<br>chr16: 31203320 C/T HET (rs19270544),<br>chr16: 31204235 T/C HOM (rs11860134, UTR) |
| | ALS2 | Chr2: 202575821 G/A HET (rs3219168, L1339L),<br>chr2: 202580514 C/T HET (rs34946105, A1295A),<br>chr2: 202625615 C/T HET (rs3219156, V368M) |
| | VAPB | Chr20: 57020741-758 TGTGTGTGTGTGTGTG/—<br>deletion HET (rs138225455),<br>chr20: 57022713-720 TGTGTGCA deletion HOM<br>(rs112902943),<br>chr20: 57023343 C/T HET (rs76295834, UTR),<br>chr20: 57023737 G/A HET (rs79623348, UTR),<br>Chr20: 57024159 C/T HET (rs74748993, UTR),<br>chr20: 57024541 T/C HET (rs6015274, UTR),<br>Chr20: 57024589 C/T HET (rs6015275, UTR),<br>chr20: 57025379 C/T HET (rs147304840, UTR),<br>chr20: 57025404-410 TCTG/— deletion HET (rs143261907) |
| | NEFH | Chr22: 29885567 A/C HET (rs75808076, A646A),<br>chr22: 29885594 A/T HET (rs79235463)<br>chr22: 29885861 T/C HOM (rs165923, A744A)<br>chr22: 29886413 C/G HOM (rs165625, V928V),<br>chr22: 29886893 G/T HOM (rs1061373, UTR) |
| | MATR3 | Chr5: 138609609 C/G HOM (rs11242456, UTR),<br>chr5: 138643062 T/A HOM (rs12153162, intron)<br>chr5: 138665756 G/A HET (rs7305, UTR),<br>chr5: 138666372 T/G HOM (rs10515507, UTR)<br>chr5: 138667325 A/G HET (rs886060006, UTR) |
| | PFN1 | No variants found |
| | SPAST | Chr2: 32340779 G/A HET (rs145264166, P293P),<br>chr2: 32379449 A/C HET (rs144594804, N579H) |
| | TUBA4A | No variants found |
| | ELP3 | No variants found |
| | DAO | No variants found |
| ALS pathogenesis associated | ANO9 | Chr11: 428385 A/G HOM (rs10794323),<br>chr11: 428489 T/C HOM (rs10794324)<br>chr11: 433387 A/G HOM,<br>chr11: 433867 G/A HET (rs12575508) |

TABLE 1-continued

SNP mutation (whole-exome sequencing), ALS pathogenesis related.

| Category | Gene | SNP mutation, insertion, and deletion |
|---|---|---|
| | DCTN1 | No variants found |
| | UBQLN2 | No variants found |
| | GPR158 | Chr10: 25701341 C/G HOM (rs2480345) |
| | GREB1L | Chr18: 19079853 A/G HOM (rs4800747), |
| | | chr19: 19100759 —/TCT insertion HOM (rs34960489) |
| | IMPG2 | Chr3: 100949842 G/A HOM (rs348867, L1127L) |
| | ERBB4 | Chr2: 212251864 T/C HOM (rs3748962) |
| | APEX1 | Chr14: 20925154 T/G HET (rs1130409, D148E) |
| | CHMP2B | No variants found |
| | NEFL | Chr8: 24810088 T/A HOM (rs1059111, UTR), |
| | | chr8: 24811071 G/—deletion HOM (rs397788090, frameshift) |
| | NEFM | Chr8: 24774683 C/A HOM (rs196864, P439T) |
| | PON1 | Chr7: 94946084 A/T HET (rs854560, L55M) |
| | PON2 | No variants found |
| | PON3 | No variants found |
| | PRPH | No variants found |
| | SMN1 | No variants found |
| | SMN2 | No variants found |
| | VEGF | No variants found |

(Bold: missense, frameshift)

TABLE 2

SNP mutation (whole-exome sequencing), ATG family

| Category | Gene | SNP mutation, insertion, and deletion |
|---|---|---|
| ATG Family | ATG1 | No variants found |
| | ATG2A | Chr11: 64677293 G/C HOM (rs656195), |
| | | chr11: 64680819 G/A HET |
| | ATG2B | Chr14: 96771959 A/G HOM (rs2289622), |
| | | chr14: 96781912 T/C HOM (rs923945) |
| | | chr14: 96797724 G/A HOM (rs1822372) |
| | ATG3 | Chr3: 112253059 —/A insertion HOM (rs35560667), |
| | | chr3: 112280706 C/G HOM (rs2399431) |
| | ATG4A | No variants found |
| | ATG4B | Chr2: 242610738 T/C HOM, |
| | | chr2: 242610773 T/A HOM |
| | | chr2: 242610264 —/G insertion HOM (rs34358233) |
| | ATG4C | No variants found |
| | ATG4D | Chr19: 10659659 C/T HET |
| | ATG5 | No variants found |
| | ATG7 | Chr3: 11596897 A/G HOM |
| | ATG9A | Chr2: 220084902 G/A HOM (rs3755048), |
| | | chr2: 220085845 A/G HOM (rs2276633) |
| | ATG9B | Chr7: 150713827 G/A HET (rs3800789), |
| | | chr7: 150713902 —/C insertion (rs11393607) |
| | ATG10 | No variants found |
| | ATG12 | Chr5: 115176589 A/G HOM (rs26536) |
| | ATG13 | Chr11: 46694133 T/C- deletion |
| | ATG14 | Chr14: 55864130 A/G HET (rs8003279) |
| | ATG16L2 | Chr11: 72532708 C/T HOM (rs11235603), |
| | | chr11: 72540633 —/TCTA insertion HET (rs144487404) |

TABLE 3

SNP mutation (whole-exome sequencing), autophagy related.

| Category | Gene | SNP mutation, insertion, and deletion |
|---|---|---|
| Autophagy Related | BCL2 | Chr18: 60795541 C/T HET, |
| | | Chr18: 60985879 T/C HET, |
| | | chr18: 60986549 C/G HOM (rs1473418) |
| | BCL2L1 | No variants found |
| | BECN1 | Chr17: 40963597 C/T HET (rs117018379) |
| | CASP3 | No variants found |

TABLE 3-continued

SNP mutation (whole-exome sequencing), autophagy related.

| Category | Gene | SNP mutation, insertion, and deletion |
|---|---|---|
| | CASP8 | Chr2: 202122995 A/G HOM, |
| | | chr2: 2021151439 G/C HOM |
| | CLN3 | No variants found |
| | CXCR4 | Chr2: 136873549 A/T HET (rs2680880) |
| | FADD | Chr11: 70049523 A/G HOM (rs1131677) |
| | FAS | Chr10: 90771829 T/C HET (rs2234978), |
| | | chr10: 90775291 C/T HET |
| | HTT | Chr4: 3076603-06 CAGCAG/CAGCAGCAG (rs374076986), |
| | | chr4: 3219613 A/C HOM |
| | IFNG | No variants found |
| | IGF1 | No variants found |
| | TNF | No variants found |
| | TNFSF10 | No variants found |
| | TP53 | Chr17: 7578645 C/T HOM, |
| | | chr17: 7578712-8714 TTT/— deletion (rs141204613) |
| | ULK1 | Chr12: 133296603 C/T HOM (rs1166018), |
| | | chr12: 132401050 C/T HET (rs61731334) |
| | | chr12: 132402020 T/C HOM (rs4964918), |
| | | Chr12: 132403161 A/G HOM (rs11609348) |
| | | Chr12: 132406275 A/C HOM (rs7311029) |
| | ULK2 | Chr17: 19702892 —/AA insertion HET (rs34321770), |
| | | chr17: 19713740 C/T HOM (rs150122) |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A microfluidic device comprising
   a first culture compartment comprising one or more neuronal cells in a hydrogel and endothelial cells forming a tightly packed monolayer on top of the hydrogel, and one or more retaining features,
   a second culture compartment comprising one or more innervated muscle bundles and one or more compliant pillars, pressure, tension, strain or deflection sensors, devices or structures for measuring changes in the force generated by the muscle bundle, wherein the compliant pillars are deflectable to measure force generated by the muscle bundle,
   wherein the neuronal cells or axons formed by the neuronal cells in the first culture compartment are able to pass into the second culture compartment to innervate the one or more muscle bundles in the second culture compartment.

2. The microfluidic device of claim 1 wherein the neuronal cells and/or the muscle cells are diseased, dysfunctional, or defective.

3. The microfluidic device of claim 1 wherein the endothelial cells are brain specific endothelial cells.

4. The microfluidic device of claim 1 comprising one or more compounds to determine if the compounds cross an endothelial barrier to the neurons or innervated muscle bundles.

5. The microfluidic device of claim 4 wherein the compounds are to be tested for treating motor neuron and/or muscle dysfunction in the second compartment.

6. The microfluidic device of claim 4 comprising a concentration gradient driving the compounds to be tested to the neurons, innervated muscle bundles, or both, the culture compartments allowing for the generation of concentration gradients capable of emulating a distribution of factors as found in the body.

7. The microfluidic device of claim 4 comprising a third compartment fluidically connecting the first and second culture compartment.

8. The microfluidic device of claim 1, wherein the geometrical configuration of the first or second coculture chambers matches the dimensions of multichannel pipettors for seeding, administration of agent to, and administration of culture medium into multiple parallel cultures.

9. The microfluidic device of claim 8 allowing for the generation of concentration gradients in the coculture chambers, capable of emulating a distribution of compound to be tested or factors found in the body around neuronal cells and muscle bundles.

10. The microfluidic device of claim 1, wherein the muscle bundle is innervated by the neuronal cell and forms a three dimensional motor unit and a neuromuscular junction in vitro.

11. The microfluidic device of claim 10, wherein innervation comprises one or more of
   (a) growth of neurites into contact with the external surface of the muscle bundle,
   (b) growth of neurites past the external surface and into the muscle bundle, and
   (c) formation of a neuromuscular junction between an axon and a muscle cell of the muscle bundle.

12. The microfluidic device of claim 1, wherein the first culture compartment, the second culture compartment, and/or optional buffer compartment between the first and second culture compartment contain a hydrogel.

13. The microfluidic device of claim 1,
   wherein an axon extends from a neural cell in the first culture compartment through to the second culture compartment and forms a three-dimensional neuromuscular junction with the muscle bundle.

14. The microfluidic device of claim 1, further comprising one or more neuronal inlet injection ports for seeding the first culture compartment with neuronal cells, one or more muscle inlet injection ports for seeding the second culture compartment with muscle cells, a first medium reservoir adjacent the first culture compartment, and a second medium reservoir adjacent the second culture compartment, the first and second medium reservoirs enabling generation of gradients of growth factors and/or other additives to the medium.

15. The microfluidic device of claim 1, wherein the first culture compartment, the second culture compartment, and/or an optional buffer compartment contains one or more additional cell types other than the neuronal cell or the muscle cell.

16. The microfluidic device of claim 15, wherein the additional cell type(s) are selected from the group consisting of astrocytes, Schwann cells, endothelial cells, satellite cells, and glial cells, optionally derived from an individual with the same disease, dysfunction, or defect.

17. The microfluidic device of claim 1, wherein the endothelial cells are brain-specific.

18. The microfluidic device of claim 1, wherein additional cells are derived from an individual with the same disease, dysfunction, or defect.

19. The microfluidic device of claim 1, wherein the disease or disorder is selected from the group consisting of amyotrophic lateral sclerosis (ALS), Huntington's disease (HD), a muscular dystrophy, spina bifida, Parkinson's disease (PD) or a PD-related disorders, Alzheimer's disease (AD) or another dementias, a disease of the blood vessels that supply the brain, a seizure disorder, cancer, infection, a prion disease, corticobasal degeneration, frontotemporal dementia, cognitive impairment, a motor neuron disease (MND), spinocerebellar ataxia (SCA), spinal muscular atrophy (SMA), Friedreich's Ataxia, Lewy Body Disease, Alpers' Disease, Batten Disease, Cerebro-Oculo-Facio-Skeletal Syndrome, corticobasal degeneration, Gerstmann-Straussler-Scheinker Disease, Kuru, Leigh's Disease, monomelic amyotrophy, multiple system atrophy, multiple system atrophy with orthostatic hypotension (Shy-Drager Syndrome), Multiple Sclerosis (MS), neurodegeneration with brain iron accumulation, opsoclonus myoclonus, posterior cortical atrophy, primary progressive aphasia, progressive supranuclear palsy, vascular dementia, progressive multifocal leukoencephalopathy, dementia with Lewy Bodies, lacunar syndromes, hydrocephalus, Wernicke-Korsakoff's syndrome, post-encephalitic dementia, cancer and chemotherapy-associated cognitive impairment and dementia, depression-induced dementia, Guillain-Barré syndrome and pseudodementia.

20. The microfluidic device of claim 18, wherein any one or more of the cells is derived from an embryonic stem cell, an induced pluripotent stem cell, or a combination thereof.

21. The microfluidic device of claim 1, wherein
the first culture compartment has a width of at least 100 µm,
the second culture compartment has a width of at least 100 µm,
the first and second culture compartments are separated by a distance of at least about 200 µm, and
the one or more pressure, tension, strain or deflection sensors, devices or structures for measuring changes in the force incorporated into or abutting pillars or support structure that are activated by movement of the pillars, support structure or sides of the device, as a result of movement of the muscle bundles, have a height of at least 50 µm.

22. A method of identifying a compound, a dosage of a compound, a dosing regime, or combination thereof, that effects the activity of innervated muscle bundles comprising
(i) making a first measurement of a biochemical, cellular, molecular, or morphological characteristic of the neuronal cell, muscle cells, or innervated muscle bundle, or combination thereof, of the microfluidic device of claim 1,
(ii) contacting the neuronal cell, muscle cells, or innervated muscle bundle, or combination thereof, with one or more amounts, for one or more dosing regimes, of a test compound, or a combination thereof,
(iii) making a second measurement of the biochemical, cellular, molecular, or morphological characteristic of the neuronal cell, muscle cells, or innervated muscle bundle, or combination thereof, and
(iv) selecting the compound, dosage and/or dosing regimes, or combination thereof, that effects neuronal activity, muscular activity, or a combination thereof if the compound improves or worsens the biochemical, cellular, molecular, or morphological characteristic of the neuronal cell, muscle cells, or innervated muscle bundle, or combination thereof.

23. The method of claim 22, wherein the compound, dosage or dosing regime, or combination thereof, of treatment improves a biochemical, cellular, molecular, or morphological characteristic of the neuronal cell, muscle cells, innervated muscle bundle, or combination thereof.

24. The method of claim 23, wherein improving the characteristic in a subject in need thereof is effective for the treatment of one or more symptoms of a neuro-, muscular, or neuromuscular disease or symptom thereof.

25. The method of claim 24, wherein the compound, dosage, or dosing regime of treatment worsens a biochemical, cellular, molecular, or morphological characteristic of the neuronal cell, muscle cells, or innervated muscle bundle, or combination thereof.

26. The method of claim 25, wherein worsening the characteristic in a subject would cause or aggravate a neuro-, muscular, or neuromuscular disease or disorder in the subject.

27. The method of claim 22, wherein the characteristic is selected from the group consisting of growth of the cell(s), morphology of the cell(s), expression of one or more marker proteins, Ca+ imaging, contractile force, neuronal soma size, apoptosis, autophagy, neurite elongation speed, neurite elongation distance, motor unit formation, neuromuscular junction formation, synaptic activity, secretion of ciliary neurotrophic factor (CNTF), and inflammation.

28. The method of claim 27, wherein the marker protein is islet1, ChAT, SMI-32, Synapsin I, ATG5, ATG7, ATG16L2, BECN1, ULK1, ULK2, LC3, MYHI, MYHII, MYLII, or a combination thereof.

29. The method of claim 27, wherein inflammation is measured by determining the expression level of NF-κB, tumor necrosis factor-α (TNF-α), interleukin family proteins, cyclooxygenase-2, or a combination thereof.

* * * * *